United States Patent
McDaniel

(10) Patent No.: US 9,144,690 B2
(45) Date of Patent: Sep. 29, 2015

(54) SYSTEM AND METHOD FOR THE PHOTODYNAMIC TREATMENT OF BURNS, WOUNDS, AND RELATED SKIN DISORDERS

(75) Inventor: David H. McDaniel, Virginia Beach, VA (US)

(73) Assignee: L'OREAL, Paris (FR)

( * ) Notice: Subject to any disclaimer, the term of this patent is extended or adjusted under 35 U.S.C. 154(b) by 158 days.

(21) Appl. No.: 12/550,464

(22) Filed: Aug. 31, 2009

(65) Prior Publication Data

US 2010/0137950 A1     Jun. 3, 2010

Related U.S. Application Data

(63) Continuation of application No. 10/903,483, filed on Aug. 2, 2004, now abandoned.

(60) Provisional application No. 60/491,277, filed on Jul. 31, 2003.

(51) Int. Cl.
    *A61N 5/06*      (2006.01)

(52) U.S. Cl.
CPC ....... *A61N 5/0616* (2013.01); *A61N 2005/0652* (2013.01); *A61N 2005/0659* (2013.01); *A61N 2005/0662* (2013.01)

(58) Field of Classification Search
CPC .................. A61B 18/203; A61B 2018/00452; A61B 2018/207; A61B 2017/00057; A61B 2017/00061; A61B 2017/00066; A61N 2005/0652; A61N 5/0616
USPC ....... 606/2–10; 607/88–91; 128/898
See application file for complete search history.

(56) References Cited

U.S. PATENT DOCUMENTS

| | | | |
|---|---|---|---|
| 3,499,437 A | 3/1970 | Balamuth |
| 3,876,907 A | 4/1975 | Widmayer |
| 3,930,335 A | 1/1976 | Widmayer |
| 4,069,823 A | 1/1978 | Isakov et al. |
| 4,309,989 A | 1/1982 | Fahim |
| 4,458,678 A | 7/1984 | Yannas et al. |
| 4,558,700 A | 12/1985 | Mutzhas |
| 4,603,496 A | 8/1986 | Latz et al. |
| 4,621,287 A | 11/1986 | Reitmeier et al. |
| 4,628,422 A | 12/1986 | Ewald |
| 4,629,363 A | 12/1986 | Dearden et al. |

(Continued)

FOREIGN PATENT DOCUMENTS

| | | |
|---|---|---|
| EP | 0159446 | 10/1985 |
| EP | 0298661 | 1/1989 |

(Continued)

OTHER PUBLICATIONS

Response to Office Action dated Jun. 2, 2006 for Canadian Patent Application No. 2452408.

(Continued)

*Primary Examiner* — Aaron Roane
(74) *Attorney, Agent, or Firm* — Oblon, McClelland, Maier & Neustadt, L.L.P.

(57) ABSTRACT

A method including photomodulating mammalian tissue with more than one light source of narrowband, multi chromatic electromagnetic radiation, wherein at least one light source emits radiation at a wavelength corresponding to yellow light and at least one light source emits radiation corresponding to infra-red light, wherein the ratio of the intensity of yellow light to infra-red light is about 4:1.

6 Claims, 30 Drawing Sheets

(56) References Cited

U.S. PATENT DOCUMENTS

| | | |
|---|---|---|
| 4,646,743 A | 3/1987 | Parris |
| 4,753,958 A | 6/1988 | Weinstein et al. |
| 4,764,379 A | 8/1988 | Sanders et al. |
| 4,767,402 A | 8/1988 | Kost et al. |
| 4,781,924 A | 11/1988 | Lee et al. |
| 4,822,335 A | 4/1989 | Kawai et al. |
| 4,836,203 A | 6/1989 | Muller et al. |
| 4,837,027 A | 6/1989 | Lee et al. |
| 4,880,001 A | 11/1989 | Weinberg |
| 4,888,354 A | 12/1989 | Chang et al. |
| 4,907,132 A | 3/1990 | Parker |
| 4,930,504 A | 6/1990 | Diamantopoulos et al. |
| 4,932,934 A | 6/1990 | Dougherty et al. |
| 4,935,665 A | 6/1990 | Murata |
| 4,969,912 A | 11/1990 | Kelman et al. |
| 5,001,556 A | 3/1991 | Nakamura et al. |
| 5,012,609 A | 5/1991 | Ignatius et al. |
| 5,016,615 A | 5/1991 | Driller et al. |
| 5,021,452 A | 6/1991 | Labbe et al. |
| 5,034,613 A | 7/1991 | Denk et al. |
| 5,037,432 A | 8/1991 | Molinari |
| 5,071,416 A | 12/1991 | Heller et al. |
| 5,147,349 A | 9/1992 | Johnson et al. |
| 5,150,704 A | 9/1992 | Tatebayashi et al. |
| 5,171,215 A | 12/1992 | Flanagan |
| 5,198,465 A | 3/1993 | Dioguardi |
| 5,226,907 A | 7/1993 | Tankovich |
| 5,231,975 A | 8/1993 | Bommannan et al. |
| 5,257,173 A | 10/1993 | Ohmamyuda et al. |
| 5,259,380 A | 11/1993 | Mendes et al. |
| 5,262,401 A | 11/1993 | Vogel et al. |
| 5,266,480 A | 11/1993 | Naughton et al. |
| 5,278,432 A | 1/1994 | Ignatius et al. |
| 5,332,802 A | 7/1994 | Kelman et al. |
| 5,344,434 A | 9/1994 | Talmore |
| 5,358,503 A | 10/1994 | Bertwell et al. |
| 5,360,824 A | 11/1994 | Barker |
| 5,366,498 A | 11/1994 | Brannan et al. |
| 5,397,352 A | 3/1995 | Burres |
| 5,399,583 A | 3/1995 | Levy et al. |
| 5,421,816 A | 6/1995 | Lipkovker |
| 5,423,803 A | 6/1995 | Tankovich et al. |
| 5,425,728 A | 6/1995 | Tankovich |
| 5,445,146 A | 8/1995 | Bellinger |
| 5,445,608 A | 8/1995 | Chen et al. |
| 5,445,611 A | 8/1995 | Eppstein et al. |
| 5,445,634 A | 8/1995 | Keller |
| 5,460,939 A | 10/1995 | Hansbrough et al. |
| 5,474,528 A | 12/1995 | Meserol |
| 5,492,135 A | 2/1996 | Devore |
| 5,500,009 A | 3/1996 | Mendes et al. |
| 5,549,660 A | 8/1996 | Mendes et al. |
| 5,591,444 A | 1/1997 | Boss, Jr. |
| 5,616,140 A | 4/1997 | Prescott |
| 5,618,275 A | 4/1997 | Bock |
| 5,620,478 A | 4/1997 | Eckhouse |
| 5,634,711 A | 6/1997 | Kennedy et al. |
| 5,636,632 A | 6/1997 | Bommannan et al. |
| 5,643,334 A | 7/1997 | Eckhouse et al. |
| 5,647,866 A | 7/1997 | Zaias et al. |
| 5,658,323 A | 8/1997 | Miller |
| 5,660,461 A | 8/1997 | Ignatius et al. |
| 5,660,836 A | 8/1997 | Knowlton |
| 5,660,850 A | 8/1997 | Boss, Jr. |
| 5,662,644 A | 9/1997 | Swor |
| 5,665,053 A | 9/1997 | Jacobs |
| 5,665,372 A | 9/1997 | Boss, Jr. |
| 5,669,916 A | 9/1997 | Andersen |
| 5,683,380 A | 11/1997 | Eckhouse et al. |
| 5,686,112 A | 11/1997 | Liedtke |
| 5,698,866 A | 12/1997 | Doiron et al. |
| 5,707,401 A | 1/1998 | Talmore |
| 5,728,090 A | 3/1998 | Martin et al. |
| 5,752,948 A | 5/1998 | Tankovich et al. |
| 5,752,949 A | 5/1998 | Tankovich et al. |
| 5,755,752 A | 5/1998 | Segal |
| 5,766,214 A | 6/1998 | Mehl, Sr. et al. |
| 5,766,233 A | 6/1998 | Thiberg |
| 5,766,234 A | 6/1998 | Chen et al. |
| 5,773,609 A | 6/1998 | Robinson et al. |
| 5,800,478 A | 9/1998 | Chen et al. |
| 5,800,479 A | 9/1998 | Thiberg |
| 5,810,801 A | 9/1998 | Anderson et al. |
| 5,814,599 A | 9/1998 | Mitragotri et al. |
| 5,817,089 A | 10/1998 | Tankovich et al. |
| 5,829,448 A | 11/1998 | Fisher et al. |
| 5,836,999 A | 11/1998 | Eckhouse et al. |
| 5,837,224 A | 11/1998 | Voorhees et al. |
| 5,843,072 A | 12/1998 | Furumoto et al. |
| 5,849,029 A | 12/1998 | Eckhouse et al. |
| 5,871,480 A | 2/1999 | Tankovich |
| 5,904,659 A | 5/1999 | Duarte et al. |
| 5,913,883 A | 6/1999 | Alexander et al. |
| 5,932,240 A | 8/1999 | D'Angelo et al. |
| 5,947,921 A | 9/1999 | Johnson et al. |
| 5,951,596 A | 9/1999 | Bellinger |
| 5,954,675 A | 9/1999 | Dellagatta |
| 5,968,034 A | 10/1999 | Fullmer et al. |
| 5,997,569 A | 12/1999 | Chen et al. |
| 6,024,717 A | 2/2000 | Ball et al. |
| 6,030,374 A | 2/2000 | McDaniel |
| 6,048,301 A | 4/2000 | Sabuda |
| 6,050,990 A | 4/2000 | Tankovich et al. |
| 6,063,108 A | 5/2000 | Salansky |
| 6,074,382 A | 6/2000 | Asah et al. |
| 6,096,066 A | 8/2000 | Chen |
| 6,099,522 A | 8/2000 | Knopp |
| 6,110,106 A | 8/2000 | MacKinnon et al. |
| 6,113,559 A | 9/2000 | Klopotek |
| 6,120,497 A | 9/2000 | Anderson et al. |
| 6,130,254 A | 10/2000 | Fisher et al. |
| 6,143,287 A | 11/2000 | Ben-Hur et al. |
| 6,162,211 A | 12/2000 | Tankovich et al. |
| 6,171,331 B1 | 1/2001 | Bagraev et al. |
| 6,171,332 B1 | 1/2001 | Whitehurst |
| 6,174,325 B1 | 1/2001 | Eckhouse |
| 6,183,773 B1 | 2/2001 | Anderson |
| 6,187,029 B1 | 2/2001 | Shapiro et al. |
| 6,190,315 B1 | 2/2001 | Kost et al. |
| 6,190,376 B1 | 2/2001 | Asah |
| 6,214,034 B1 | 4/2001 | Azar |
| 6,221,095 B1 | 4/2001 | Van Zuylen et al. |
| 6,223,071 B1 | 4/2001 | Lundahl et al. |
| 6,231,528 B1 | 5/2001 | Kaufman et al. |
| 6,238,424 B1 | 5/2001 | Thiberg |
| 6,251,127 B1 | 6/2001 | Biel |
| 6,267,779 B1 | 7/2001 | Gerdes |
| 6,273,884 B1 | 8/2001 | Altshuler |
| 6,283,956 B1 | 9/2001 | McDaniel |
| 6,290,713 B1 | 9/2001 | Russell |
| 6,302,874 B1 | 10/2001 | Zhang et al. |
| 6,312,450 B1 | 11/2001 | Yavitz et al. |
| 6,387,089 B1 | 5/2002 | Kreindel et al. |
| 6,398,753 B2 | 6/2002 | McDaniel |
| 6,413,268 B1 | 7/2002 | Hartman |
| 6,436,127 B1 | 8/2002 | Anderson et al. |
| 6,443,946 B2 | 9/2002 | Clement et al. |
| 6,443,978 B1 * | 9/2002 | Zharov ........................... 607/91 |
| 6,459,087 B1 | 10/2002 | Kaas |
| 6,471,716 B1 | 10/2002 | Pecukonis |
| 6,497,719 B2 | 12/2002 | Pearl et al. |
| 6,524,330 B1 | 2/2003 | Khoobehi et al. |
| 6,602,275 B1 | 8/2003 | Sullivan |
| 6,629,971 B2 | 10/2003 | McDaniel |
| 6,630,516 B2 | 10/2003 | Varani et al. |
| 6,645,230 B2 | 11/2003 | Whitehurst |
| 6,663,659 B2 | 12/2003 | McDaniel |
| 6,664,217 B1 | 12/2003 | Puvvada et al. |
| 6,676,655 B2 | 1/2004 | McDaniel |
| 6,709,866 B2 | 3/2004 | Robertson et al. |
| 6,723,698 B2 | 4/2004 | Rueger et al. |
| 6,723,798 B1 | 4/2004 | Yoo |
| 6,746,444 B2 * | 6/2004 | Key ................................ 606/9 |
| 6,835,306 B2 | 12/2004 | Caldwell |

(56) References Cited

U.S. PATENT DOCUMENTS

| | | |
|---|---|---|
| 6,866,678 B2 | 3/2005 | Shenderova |
| 6,881,211 B2 | 4/2005 | Schweikert et al. |
| 6,887,260 B1 | 5/2005 | McDaniel |
| 6,936,044 B2 | 8/2005 | McDaniel |
| 7,004,933 B2 | 2/2006 | McDaniel |
| 7,033,381 B1 | 4/2006 | Larsen |
| 7,081,128 B2 | 7/2006 | Hart et al. |
| 7,115,120 B2 | 10/2006 | Lin |
| 7,147,863 B2 | 12/2006 | Fisher |
| 7,195,755 B2 | 3/2007 | Nguyen et al. |
| 7,201,765 B2 | 4/2007 | McDaniel |
| 7,204,832 B2 | 4/2007 | Altshuler et al. |
| 7,258,695 B2 | 8/2007 | Carullo, Jr. et al. |
| 7,264,629 B2 | 9/2007 | Simkin et al. |
| 7,267,673 B2 | 9/2007 | Pilcher et al. |
| 7,309,335 B2 | 12/2007 | Altshuler et al. |
| 7,331,952 B2 | 2/2008 | Walneck et al. |
| 7,354,432 B2 | 4/2008 | Eells et al. |
| 7,438,719 B2 | 10/2008 | Chung et al. |
| 7,470,270 B2 | 12/2008 | Azar et al. |
| 7,494,503 B2 | 2/2009 | McDaniel |
| 7,511,031 B2 | 3/2009 | Chen |
| 7,559,944 B2 | 7/2009 | Whang |
| 7,597,708 B2 | 10/2009 | Carullo, Jr. et al. |
| 7,618,414 B2 | 11/2009 | Connors et al. |
| 8,188,074 B2 | 5/2012 | Brown et al. |
| 8,328,794 B2 | 12/2012 | Altshuler et al. |
| 8,372,433 B2 | 2/2013 | Shinoka et al. |
| 2001/0013349 A1 | 8/2001 | Clement et al. |
| 2001/0023363 A1 | 9/2001 | Harth et al. |
| 2001/0053347 A1 | 12/2001 | Varani et al. |
| 2002/0028185 A1 | 3/2002 | Fisher et al. |
| 2002/0029071 A1 | 3/2002 | Whitehurst |
| 2002/0123746 A1 | 9/2002 | McDaniel |
| 2002/0161357 A1 | 10/2002 | Anderson et al. |
| 2002/0173833 A1 | 11/2002 | Korman et al. |
| 2002/0183724 A1 | 12/2002 | Neev |
| 2002/0198575 A1 | 12/2002 | Sullivan |
| 2003/0004499 A1 | 1/2003 | McDaniel |
| 2003/0004556 A1 | 1/2003 | McDaniel |
| 2003/0060811 A1 | 3/2003 | McDaniel |
| 2003/0129154 A1 | 7/2003 | McDaniel |
| 2004/0039378 A1 | 2/2004 | Lin |
| 2004/0215293 A1 | 10/2004 | Eells et al. |
| 2005/0090877 A1 | 4/2005 | Harth et al. |
| 2006/0129209 A1 | 6/2006 | McDaniel |
| 2006/0184214 A1 | 8/2006 | McDaniel |
| 2006/0200213 A1 | 9/2006 | McDaniel |
| 2006/0212025 A1 | 9/2006 | McDaniel |
| 2006/0265030 A1 | 11/2006 | McDaniel |
| 2007/0073276 A1 | 3/2007 | Wilkens et al. |
| 2007/0128576 A1 | 6/2007 | Boutoussov |
| 2007/0129613 A1 | 6/2007 | Rochester et al. |
| 2007/0129711 A1 | 6/2007 | Altshuler |
| 2007/0129776 A1 | 6/2007 | Robins et al. |
| 2007/0129778 A1 | 6/2007 | Dougal |
| 2007/0149900 A1 | 6/2007 | Lin |
| 2007/0149901 A1 | 6/2007 | Gordon et al. |
| 2007/0150030 A1 | 6/2007 | Pearl |
| 2007/0156208 A1 | 7/2007 | Havell |
| 2007/0167999 A1 | 7/2007 | Breden et al. |
| 2007/0168000 A1 | 7/2007 | Happawana |
| 2007/0173912 A1 | 7/2007 | Amornsiripanitch |
| 2007/0173913 A1 | 7/2007 | Anderson et al. |
| 2007/0179482 A1 | 8/2007 | Anderson |
| 2007/0179574 A1 | 8/2007 | Elliott |
| 2007/0198004 A1 | 8/2007 | Altshuler et al. |
| 2007/0208326 A1 | 9/2007 | Connors |
| 2007/0208328 A1 | 9/2007 | Boutoussov |
| 2007/0208395 A1 | 9/2007 | Leclerc |
| 2007/0208396 A1 | 9/2007 | Whatcott |
| 2007/0208400 A1 | 9/2007 | Nadkarni |
| 2007/0213696 A1 | 9/2007 | Altshuler et al. |
| 2007/0219604 A1 | 9/2007 | Yaroslavsky et al. |
| 2007/0219605 A1 | 9/2007 | Yaroslavsky et al. |
| 2007/0231255 A1 | 10/2007 | Barolet et al. |
| 2007/0239142 A1 | 10/2007 | Altshuler et al. |
| 2007/0239147 A1 | 10/2007 | Manstein et al. |
| 2007/0299486 A1 | 12/2007 | Hoenig et al. |
| 2008/0009923 A1 | 1/2008 | Paithankar |
| 2008/0015555 A1 | 1/2008 | Manstein et al. |
| 2008/0021528 A1 | 1/2008 | Carullo |
| 2008/0031833 A1 | 2/2008 | Oblong |
| 2008/0031924 A1 | 2/2008 | Gilson |
| 2008/0033516 A1 | 2/2008 | Altshuler et al. |
| 2008/0035864 A1 | 2/2008 | Fiset |
| 2008/0039906 A1 | 2/2008 | Huang et al. |
| 2008/0045933 A1 | 2/2008 | Perl |
| 2008/0051856 A1 | 2/2008 | Vizethum |
| 2008/0058783 A1 | 3/2008 | Altshuler et al. |
| 2008/0058784 A1 | 3/2008 | Manstein et al. |
| 2008/0058905 A1 | 3/2008 | Wagner |
| 2008/0065056 A1 | 3/2008 | Powell et al. |
| 2008/0065175 A1 | 3/2008 | Redmond |
| 2008/0077199 A1 | 3/2008 | Shefl |
| 2008/0082148 A1 | 4/2008 | Bernstein |
| 2008/0082149 A1 | 4/2008 | Bernstein |
| 2008/0091179 A1 | 4/2008 | Durkin et al. |
| 2008/0097278 A1 | 4/2008 | Cole |
| 2008/0097419 A1 | 4/2008 | MacFarland |
| 2008/0103560 A1 | 5/2008 | Powell et al. |
| 2008/0106896 A1 | 5/2008 | Liu et al. |
| 2008/0139901 A1 | 6/2008 | Altshuler et al. |
| 2008/0147054 A1 | 6/2008 | Altshuler et al. |
| 2008/0147148 A1 | 6/2008 | Baldacchini |
| 2008/0172112 A1 | 7/2008 | Gourgouliatos et al. |
| 2008/0172114 A1 | 7/2008 | Gourgouliatos et al. |
| 2008/0177255 A1 | 7/2008 | Bernardini |
| 2008/0183161 A1 | 7/2008 | Walneck et al. |
| 2008/0200908 A1 | 8/2008 | Domankevitz |
| 2008/0203280 A1 | 8/2008 | Rizoiu |
| 2008/0208294 A1 | 8/2008 | Pierce |
| 2008/0208295 A1 | 8/2008 | Cumbie |
| 2008/0234669 A1 | 9/2008 | Kauvar |
| 2008/0234786 A1 | 9/2008 | Cumbie |
| 2008/0255640 A1 | 10/2008 | Kipp |
| 2008/0262394 A1 | 10/2008 | Pryor |
| 2008/0262482 A1 | 10/2008 | Hantash et al. |
| 2008/0262576 A1 | 10/2008 | Creamer |
| 2008/0267814 A1 | 10/2008 | Bornstein |
| 2008/0269732 A1 | 10/2008 | Pyun |
| 2008/0269733 A1 | 10/2008 | Anderson |
| 2008/0269844 A1 | 10/2008 | Logslett |
| 2008/0269848 A1 | 10/2008 | Birmingham et al. |
| 2008/0269849 A1 | 10/2008 | Lewis |
| 2008/0275532 A1 | 11/2008 | Yamazaki |
| 2008/0281307 A1 | 11/2008 | Donahue |
| 2008/0294151 A1 | 11/2008 | Whitaker et al. |
| 2008/0294152 A1 | 11/2008 | Altshuler et al. |
| 2009/0012508 A1 | 1/2009 | Dougal |
| 2009/0018621 A1 | 1/2009 | Vogler et al. |
| 2009/0018622 A1 | 1/2009 | Asvadi et al. |
| 2009/0024116 A1 | 1/2009 | Mulhauser et al. |
| 2009/0043293 A1 | 2/2009 | Pankratov et al. |
| 2009/0062889 A1 | 3/2009 | Kiessl |
| 2009/0082836 A1 | 3/2009 | Schell |
| 2009/0088824 A1 | 4/2009 | Baird et al. |
| 2009/0105791 A1 | 4/2009 | McGinnis |
| 2009/0112192 A1 | 4/2009 | Barolet |
| 2009/0112294 A1 | 4/2009 | Huang |
| 2009/0149843 A1 | 6/2009 | Smits et al. |
| 2009/0177190 A1 | 7/2009 | Lee |
| 2009/0177253 A1 | 7/2009 | Darm et al. |
| 2009/0177256 A1 | 7/2009 | Ripper et al. |
| 2009/0187169 A1 | 7/2009 | Durkin et al. |
| 2009/0198173 A1 | 8/2009 | Samuel et al. |
| 2009/0227996 A1 | 9/2009 | Powell et al. |
| 2009/0234253 A1 | 9/2009 | Vandenbelt |
| 2009/0234337 A1 | 9/2009 | Ely et al. |
| 2009/0234341 A1 | 9/2009 | Roth |
| 2009/0234342 A1 | 9/2009 | Ely et al. |
| 2009/0247932 A1 | 10/2009 | Barolet |
| 2009/0251057 A1 | 10/2009 | Son et al. |
| 2009/0254154 A1 | 10/2009 | De Taboada |

(56) References Cited

U.S. PATENT DOCUMENTS

| | | |
|---|---|---|
| 2009/0254156 A1 | 10/2009 | Powell et al. |
| 2009/0270845 A1 | 10/2009 | Birmingham et al. |
| 2009/0270946 A1 | 10/2009 | Spivak |
| 2009/0270953 A1 | 10/2009 | Ecker |
| 2010/0121254 A1 | 5/2010 | McDaniel |
| 2010/0256550 A1 | 10/2010 | McDaniel |

FOREIGN PATENT DOCUMENTS

| | | |
|---|---|---|
| EP | 0320080 | 6/1989 |
| EP | 1839705 A1 | 3/2007 |
| EP | 1818077 A1 | 8/2007 |
| EP | 1837050 A1 | 9/2007 |
| EP | 1839704 | 10/2007 |
| EP | 1842571 A2 | 10/2007 |
| EP | 1857145 A1 | 11/2007 |
| EP | 1878466 A1 | 1/2008 |
| EP | 1916016 A1 | 4/2008 |
| EP | 1920798 A1 | 5/2008 |
| EP | 1935452 A1 | 6/2008 |
| EP | 1958662 A1 | 8/2008 |
| EP | 1964590 A1 | 9/2008 |
| EP | 2044901 | 4/2009 |
| EP | 2044973 | 4/2009 |
| EP | 2044974 | 4/2009 |
| EP | 2055349 | 5/2009 |
| EP | 2106198 | 9/2009 |
| EP | 2106780 | 10/2009 |
| EP | 2106824 | 10/2009 |
| EP | 2110159 | 10/2009 |
| GB | 2262043 | 6/1993 |
| GB | 2360461 | 9/2001 |
| GB | 2360641 | 9/2001 |
| JP | H01-136668 | 5/1989 |
| JP | 07-016304 | 1/1995 |
| JP | H07-100219 | 4/1995 |
| JP | H07505614 | 6/1995 |
| JP | H08308943 | 11/1996 |
| JP | H09-508031 | 8/1997 |
| JP | H10-503109 | 3/1998 |
| JP | 2000-202044 | 7/2000 |
| JP | 2002-522110 | 7/2002 |
| JP | 2002535101 | 10/2002 |
| JP | 2005503388 | 2/2005 |
| JP | 2010047590 | 3/2010 |
| RU | 1724269 | 4/1992 |
| WO | 93/09847 | 5/1993 |
| WO | 93/09874 | 5/1993 |
| WO | 93/21842 | 11/1993 |
| WO | 95/19809 | 7/1995 |
| WO | 96/11723 | 4/1996 |
| WO | 96/24406 | 8/1996 |
| WO | 97/46279 | 12/1997 |
| WO | 98/14453 | 4/1998 |
| WO | 98/50034 | 11/1998 |
| WO | 99/04628 | 2/1999 |
| WO | 99/19024 | 4/1999 |
| WO | 99/20336 | 4/1999 |
| WO | 99/39763 | 8/1999 |
| WO | 00/02491 | 1/2000 |
| WO | 00/02497 | 1/2000 |
| WO | 00/07514 | 2/2000 |
| WO | 00/32121 | 6/2000 |
| WO | 00/40266 | 7/2000 |
| WO | 00/44441 | 8/2000 |
| WO | 00/57804 | 10/2000 |
| WO | 00/74782 | 12/2000 |
| WO | 01/14012 | 3/2001 |
| WO | 01/40232 | 6/2001 |
| WO | 02/057811 | 7/2002 |
| WO | 03/001984 | 1/2003 |
| WO | 03/002187 | 1/2003 |
| WO | 03/005883 | 1/2003 |
| WO | 03/017824 | 3/2003 |
| WO | 03/086215 | 10/2003 |
| WO | 2004/075985 | 9/2004 |
| WO | 2004/092335 | 10/2004 |
| WO | 2005/011606 | 2/2005 |
| WO | 2005/077452 | 8/2005 |
| WO | 2005/089039 | 9/2005 |
| WO | 2005/096766 | 10/2005 |
| WO | 2005/115263 A1 | 12/2005 |
| WO | 2006/013390 | 2/2006 |
| WO | 2006/013390 A1 | 2/2006 |
| WO | 2006/099413 A2 | 9/2006 |
| WO | 2006/107387 A2 | 10/2006 |
| WO | 2006/116141 A1 | 11/2006 |
| WO | 2006/125231 A2 | 11/2006 |
| WO | 2007/013110 A1 | 2/2007 |
| WO | 2007/036002 A1 | 4/2007 |
| WO | 2007/044840 A2 | 4/2007 |
| WO | 2007/066657 A1 | 6/2007 |
| WO | 2007/087374 A2 | 8/2007 |
| WO | 2007/092349 | 8/2007 |
| WO | 2007/096344 A1 | 8/2007 |
| WO | 2007/103132 A2 | 9/2007 |
| WO | 2007/106339 A2 | 9/2007 |
| WO | 2007/106856 A2 | 9/2007 |
| WO | 2007/118303 A2 | 10/2007 |
| WO | 2007/125336 A1 | 11/2007 |
| WO | 2007/126339 A1 | 11/2007 |
| WO | 2007/146101 A2 | 12/2007 |
| WO | 2008/008971 A1 | 1/2008 |
| WO | 2008/012519 A1 | 1/2008 |
| WO | 2008/017975 A1 | 2/2008 |
| WO | 98/11723 | 3/2008 |
| WO | 2008/078750 A1 | 7/2008 |
| WO | 2008/084764 A1 | 7/2008 |
| WO | 2008/097062 A1 | 8/2008 |
| WO | 2008/128175 A1 | 10/2008 |
| WO | 2008/129740 A1 | 10/2008 |
| WO | 2008/129741 A1 | 10/2008 |
| WO | 2008/131079 A1 | 10/2008 |
| WO | 2008/131343 A1 | 10/2008 |
| WO | 2008/135548 A1 | 11/2008 |
| WO | 2008/135658 A2 | 11/2008 |
| WO | 2008/137489 A1 | 11/2008 |
| WO | 2008/146219 A1 | 12/2008 |
| WO | 2008/146220 A2 | 12/2008 |
| WO | 2008/146255 A2 | 12/2008 |
| WO | 2009/003295 A1 | 1/2009 |
| WO | 2009/008967 | 1/2009 |
| WO | 2009/014034 | 1/2009 |
| WO | 2009/016598 | 2/2009 |
| WO | 2009/016963 | 2/2009 |
| WO | 2009/023568 | 2/2009 |
| WO | 2009/023968 | 2/2009 |
| WO | 2009/038720 | 3/2009 |
| WO | 2009/056838 | 5/2009 |
| WO | 2009/059270 | 5/2009 |
| WO | 2009/064034 | 5/2009 |
| WO | 2009/089177 | 7/2009 |
| WO | 2009/107095 | 9/2009 |
| WO | 2009/117323 | 9/2009 |
| WO | 2009/118617 | 10/2009 |
| WO | 2009/121158 | 10/2009 |
| WO | 2009/123196 | 10/2009 |
| WO | 2009/125338 | 10/2009 |
| WO | 2009/132585 | 11/2009 |
| WO | 2009/137612 | 11/2009 |
| ZA | 9707751 | 3/1998 |

OTHER PUBLICATIONS

Office Action dated Mar. 2, 2007 for Canadian Patent Application No. 2452408.

Response to Office Action dated Mar. 2, 2007 for Canadian Patent Application No. 2452408.

Office Action dated Jan. 31, 2008 for Canadian Patent Application No. 2452408.

Response to Office Action dated Jan. 31, 2008 for Canadian Patent Application No. 2452408.

(56) References Cited

OTHER PUBLICATIONS

Office Action dated Nov. 10, 2008 for Korean Patent Application No. 7017182/2003.
Notices for Reasons of Rejection dated Mar. 26, 2008 for Japanese Patent Application 2003-508231.
Amendment to Notices for Reasons of Rejections dated Mar. 26, 2008 for Japanese Patent Application No. 2003-508231.
Decision of Rejection dated Feb. 2, 2009 for Japanese Patent Application No. 2003-508231.
Examination Report dated Feb. 22, 2008 for New Zealand Patent Application No. 530600.
Response to Examination Report dated Feb. 22, 2008 for New Zealand Patent Application No. 530600.
Examination Report dated Aug. 20, 2008 for New Zealand Patent Application No. 530600.
Official Letter dated Nov. 17, 2006 for Mexican Patent Application No. 2004/000187.
Reply to Official Letter dated Nov. 17, 2006 for Mexican Patent Application No. 2004/000187.
Second Official Letter dated Jul. 27, 2007 for Mexican Patent Application No. 2004/000187.
Response to Second Official Letter dated Jul. 27, 2007 for Mexican Patent Application No. 2004/000187.
Third Official Letter dated Jan. 3, 2008 for Mexican Patent Application No. 2004/000187.
Response to Third Official Letter dated Jan. 3, 2008 for Mexican Patent Application No. 2004/000187.
Office Action dated Mar. 21, 2008 for Chinese Patent Application No. 02816794.5.
Response to Office Action dated Mar. 21, 2008 for Chinese Patent Application No. 02816794.5.
Second Office Action dated Jul. 22, 2009 for Chinese Patent Application No. 02816794.5.
Response to Second Office Action dated Jul. 22, 2009 for Chinese Patent Application No. 02816794.5.
Third Office Action dated Jan. 5, 2010 for Chinese Patent Application No. 02816794.5.
Response to Third Office Action dated Jan. 5, 2010 for Chinese Patent Application 02816794.5.
First Examination Report dated Feb. 8, 2007 for European Patent Application No. 02749720.
First Statement of Proposed Amendments dated Feb. 17, 2006 for Australian Patent Application No. 2003220671.
Examiner's First Report dated Oct. 4, 2007 for Australian Patent Application No. 2003220671.
Voluntary Amendment dated Apr. 27, 2007 for Canadian Patent Application No. 2482934.
Office Action dated Jun. 15, 2007 for Canadian Patent Application No. 2482934.
Response to Office Action dated Jun. 15, 2007 for Canadian Patent Application No. 2482934.
Office Action dated Feb. 21, 2008 for Canadian Patent Application No. 2482934.
Response to Office Action dated Feb. 21, 2008 for Canadian Patent Application No. 2482934.
Office Action dated Oct. 17, 2008 for Canadian Patent Application No. 2482934.
Response to Office Action dated Oct. 17, 2008 for Canadian Patent Application No. 2482934.
Office Action dated Jun. 3, 2010 for Canadian Patent Application No. 2482934.
Response to Office Action dated Jun. 3, 2010 for Canadian Patent Application No. 2482934.
Office Action dated Feb. 1, 2011 for Canadian Patent Application No. 2482934.
First Office Action dated Mar. 10, 2006 for Chinese Patent Application No. 03813556.6.
Response to First Office Action dated Mar. 10, 2006 for Chinese Patent Application No. 03813556.6.
Second Office Action dated May 23, 2008 for Chinese Patent Application No. 03813556.6.
Response to Second Office Action dated May 23, 2008 for Chinese Patent Application No. 03813556.6.
Rejection Decision dated Oct. 30, 2009 for Chinese Patent Application No. 03813556.6.
Response to Rejection Decision dated Oct. 30, 2009 for Chinese Patent Application No. 03813556.6.
First Office Action dated Dec. 12, 2008 for Indian Patent Application No. 1590/KOLNP/2004.
Withdrawal Petition dated Nov. 20, 2009 for Indian Patent Application No. 1590/KOLNP/2004.
Written Opinion of the International Search Authority dated Apr. 12, 2005 for PCT Patent Application No. PCT/US04/10915.
European Search Report dated Oct. 6, 2010 for EP Application No. 04759316.5.
Office Action dated Feb. 2, 2011 for EP Application No. 04759316.5.
Official Action dated Oct. 25, 2006 for Canadian Patent Application No. 2531099.
First Office Action dated May 22, 2009 for Chinese Patent Application No. 200480021576.0.
Office Action dated Dec. 7, 2010 for Japanese Patent Application No. 2006-509834.
Response to Office Action dated Dec. 7, 2010 for Japanese Patent Application No. 2006-509834.
Office Action dated May 11, 2010 for Japanese Patent Application No. 2006-509834.
Response to Office Action dated May 11, 2010 for Japanese Patent Application No. 2006-509834.
Written Opinion of the International Search Authority dated Oct. 19, 2006 for PCT Patent Application No. PCT/US04/24879.
Office Action dated Feb. 28, 2012 for Canadian Patent Application No. 2533129.
Response to Office Action dated Feb. 28, 2012 for Canadian Patent Application No. 254412.
Office Action dated Jun. 17, 2011 for European Patent Application No. 4779826.9.
Response to Office Action dated Jun. 17, 2011 for European Patent Application No. 4779826.9.
First Office Action dated Jul. 15, 2009 for European Patent Application No. 04779826.9.
Response to First Office Action dated Jul. 15, 2009 for European Patent Application No. 04779826.9.
Office Action dated May 31, 2010 for Israeli Patent Application No. 173123.
Response to Office Action dated May 31, 2010 for Israeli Patent Application No. 173123.
Office Action dated Apr. 7, 2010 for Japanese Patent Application No. 2006-522123.
Response to Office Action dated Apr. 7, 2010 for Japanese Patent Application No. 2006-522123.
Office Action dated Apr. 28, 2011 directed towards Korean Patent Application 10-2006-7002207.
Response to Office Action dated Apr. 28, 2011 for Korean Patent Application 10-2006-7002207.
Office Action dated Aug. 12, 2011 for Korean Patent Application 10-2006-7002207.
Response to Office Action dated Aug. 12, 2011 for Korean Patent Application 10-2006-7002207.
"Apoptosis," dated Sep. 19, 2005, located at http:www.neuro.wustl.edu/NEUROMUSCULAR/mother/apoptosis.htm> retrieved on Oct. 24, 2007 (5 pages).
"Chlorophyll," from Wikipedia located at http://de.wikipedia.org/wiki/Chlorophyll, visited on Jul. 18, 2007 (5 pages).
"Phorphin," from Wikipedia located at <en.wikipedia.org/wiki/Porphine, visited on Jul. 18, 2007 (2 pages).
Doukas, A. et al. (1996) "Phiscail Characteristics and Biological Effects of Laser-Induced Stress Waves", Ultrasound in Med. & Biol. 22(2), pp. 151-164.
Abergel et al., (Feb. 1987) "Biostimulation of Wound Healing by Lasers: Experimental Approaches in Animal Models and in Fibroblast Cultures", J. Dermatol. Surg. Oncol. 13/(2) pp. 127-133.

(56) References Cited

OTHER PUBLICATIONS

Drastichova, V. et al., (1973), "Strengthening of Sutured Skin Wound with Ultrasound in Experiments on Animals", Acta Chirurgiae Plasticae 15, pp. 114-119.
Guffey, Stephen et al., "More Than a Thermal Modality: Ultrasound", Advance Rehabilitation, Jul./Aug. 1991.
Rolland, Alain et al. (1993) "Site-Specific Drug Delivery to Pilosebaceous Structures Using Polymeric Microspheres", Pharmaceutical Research 10(12), pp. 1738-1744.
Enwemeka, Chukuka S., "The Effects of Therapeutic Ultrasound on Tendon Healing", Am. J. Phys. Med. Rehabil., vol. 68 No. 6, pp. 283-287, Dec. 1989.
Tachibana, Katsuro et al., "Use of Ultrasound to Enhance the Local Anesthetic Effect of Topically Applied Aqueous Lidocaine", Anesthesiology, V. 78 No. 6, Jun. 1993.
Lyons, R.F. et al., "Biostimulation of Wound Healing in Vivo by a Helium-Neon Laser", Ann Plast Surg, Jan., 1987; 18(1):47-50, (Abstract).
Wester, Ronald et al. "Variations in Percutaneous Absorption of Testosterone in Rhesus Monkey Due to Anatomic Site of Application and Frequency of Application", Arch Dermatol Res., 267, 229-235 (1980).
Franz, Thomas, "Percutaneous Absorption of Minoxidil in Man", Arch Dermatol, vol. 121, Feb. 1985.
Menon, Gopinathan K. et al., "Ultrasound Localization of Calcium in Psoriatic and Normal Human Epidermis", Arch Dermatol, vol. 127, Jan. 1991.
Byl, Nancy N. et al., "Low Dose Ultrasound Effects of Wound Healing: A Controlled Study with Yucatan Pigs", Arch Phys Med Rehabil., vol. 73, Jul. 1992.
Phillips, Charlotte, et al., "Ascorbic Acid and Transforming Growth Factor-B1 Increase Collagen Biosynthesis via Different Mechanisms: Coordinate Regluation of Proal(I) and Proal(III) Collagens", Archives of Biochemistry and Biophysics, vol. 295, No. 2, 1992, pp. 397-403.
Darr, Douglas, et al., "Ascorbic Acid and Collagen Synthesis: Rethinking a Role for Lipid Peroxidation", Archives of Biochemistry and Biophysics, vol. 307, No. 2, 1993, pp. 331-335.
Menezes, Salatiel, et al., (1998) "Non-Coherent Near Infrared Radiation Protects Normal Human Dermal Fibroblasts from Solar Ultraviolet Toxicity".
Morrone, G., et al., "In Vitro Experimental Research of Rabbit Condrocytes Biostimulation with Diode Laser Ga-Al-As: a Preliminary Study", Artif Cells Blood Substit Immobil Biotechnol. Jul. 1998; 26(4):437-439 (Abstract).
Asawananda et al., "308-nm Excimer Laser for the Treatment of Psoriasis", Arch Dermatol, vol. 136, May 2000, pp. 619-624.
Krammer, B. et al. (Feb. 1993) "Photodynamic Effects on the Nuclear Envelope of Human Skin Fibroblasts", Journal of Photochem Photobiol. B: Biol. 17(2), pp. 109-114.
Bommannan et al. (1992) "Sonophoresis I. The Use of High Frequency Ultrasound to Enhance Transdermal Drug Delivery", Pharmaceutical Research 9(4), pp. 559-564.
Bommannan et al. (1992) "Sonophoresis II. Examination of the Mechanisms of Ultrasound-Enhanced Transdermal Drug Delivery", Pharmaceitcal Research 9(8), pp. 1043-1047.
Jennato S., et al. (512001), "What Color is my LED?" Photonics Spectra.
Laakso, et al. (1997), "Pain Scores and Side Effects in Response to Low Level Laser Therapy (LLLT) for Myofascial Trigger Points", Laser Therapy 9:67-72.
Labbe et al., (1990), "Laser Phobioactivation Mechanisms: In Vitro Studies Using Ascorbic Acid Uptake and Hydroxyproline Formation as Biochemical Markers of Irradiation Response", Lasers in Surgery and Medicine 10, pp. 201-207.
Liberman et al. (1996), "Light Years Ahead", pp. 277-283.
Lieb, Linda, et al. (1992), "Topical Delivery Enhancement with Multilamellar Liposomes into Pilosebaceous Units: I. In Vitro Evaluation Using Fluorescent Techniques with the Hamster Ear Model", The Journal of Investigative Dermatology 99(1).

Li, Lingna, et al. (1992), "Product-Delivering Liposomes Specifically Target Hair Follicles in Histocultured Intact Skin", In Vitro Cell Dev. Biol. 281, pp. 679-681.
Liu et al. (2002), "Inhibition of AP-1 Transcription Factor Causes Blockade of Multiple Signal Transduction Pathways and Inhibits Breast Cancer Growth", Oncogene 21:7680-7689.
Loevschall, (1994), "Effect of Low Level Diode Laser Irradiation of Human Oral Mucosa Fibroblasts in Vitro", Lasers in Surgery and Medicine 14, pp. 347-354.
Logdberg-Anderson et al. (1997), "Low Level Laser Therapy (LLLT) of Tendonitis and Myofascial Pains: a Randomized, Double-blind, Controlled Study", Laser Therapy 9:79-86.
Kloth, Luther, et al. (1996), "Promotion of Wound Healing with Electrical Stimulation", The Journal for Prevention and Healing Advances 9(5).
Coldman, M.F., et al. (1969), "Enhanced of Percutaneous Adsorption by the Use of Volatile: Nonvolatile Systems as Vehicles", Journal of Pharmaceutical Sciences vol. 58, #9.
Hrnjak, M., et al. (Nov. 1995), "Stimulatory Effect of Low-Power Density He-Ne Laser Radiation on Human Fibroblast in Vitro", Vojnosanit Pregl. 52(6), pp. 539-546.
Callam, M. J., et al. (Jul. 1987) ,"A Controlled Trial of Weekly Ultrasound Therapy in Chronic Leg Ulceration", The Lancet, pp. 204-206.
Pogrel, M., et al. (1997) ,"Effects of Low-Energy Gallium-Aluminum-Arsenide Laser Irradiation on Cultured Fibroblasts and Keratincytes", Lasers in Surgery and Medicine 20, pp. 426-432.
Weiner, M., et al. (1994), "Liposomes: A Novel Topical Delivery System for Pharmaceutical and Cosmetic Applications", Journal of Drug Targeting 2, pp. 405-410.
Dyson, Mary (Sep. 1982), "Stimulation of Tissue Repair by Therapeutic Ultrasound", Infections in Surgery 1(2), pp. 37-94.
Dyson, Mary, et al. (Apr. 1978), "Stimulation of Tissue Repair by Ultrasound: A Survey of the Mechanisms Involved", Physiotherapy 64(4), pp. 105-108.
McDaniel (May 2001), "Nonablative Skin Rejuvenation—The Wave of the Future", Cosmetic Surgery Times.
McDaniel, D. H., et al. (1996), "Treatment of Stretch Marks With the 585 Nm Flashlamp-Pumped Pulsed Dye Laser", Dermatological 22(4), pp. 332-337.
Menezes et al. (Oct. 1998), "Non-Coherent Near Infrared Radiation Protects Normal Human Dermal Fibroblasts from Solar Ultraviolet Toxicity", The Journal of Investigative Dermatology 111(4):629-633.
Monfrecola, G., et al (1987), "Topical Hematoporphyrin Plus UVA for Treatment of Alopecia Areata", Photodermatology 4:305-306.
Lehman, P. et al. (1991), "Effects of Ultraviolet A and B on the Skin Barrier: A Functional Electron Microscopic and Lipid Biochemical Study", Photodermatol Photoimmunol Photomed. 8, pp. 129-134.
Morganti, P., et al. (1997), "Enhancing the Glycolic Acid Efficacy by Piezoelectric Vibrations," J. Appl. Cosmotol. vol. 15, pp. 147-159.
Singh, Parminder, et al. (1993), "Iotophoretic Transdermal Delivery of Salicylic Acid and Lidocaine to Local Subcutaneous Structures", Journal of Pharmaceutical Sciences 82(2), pp. 127-131.
Parrish et al. (1981), "Action Spectrum for Phototherapy of Psoriasis," Journal of Investigative Dermatology 76(5):359-361.
De Deyne, Patrick G., et al. (711995), "In Vitro Effects of Therapeutic Ultrasound on the Nucleus of Human Fibroblasts", Physical Therapy 75(7), pp. 629-634.
Scheuplein, Robert ,et al. (1971), "Permeability of the Skin", Physiological Review, vol. 51, No. 4.
Polo, et al. (1999), "Role of Ground and Excited Singlet State Ozygen in the Red Light-Induced Stimulation of *Escherichia coli* Cell Growth", Biochemical and Biophysical Research Communications 257, pp. 753-758.
Potinen et al. (1996), "The Effect of Hair Lasers on Skin Blood Flow, Acupuncture & Electrotherapeutic", Res. Int. J., vol. 21, pp. 105-118.
Brucks, Richard, et al. (1989), "The Effect of Ultrasound on the In Vitro Penetration of Ibuprofen Through Human Epidermis", Pharmaceutical Research 6(8), pp. 697-701.
Borelli, S. (1955), "Chlorophyll in the Treatment 1-27 of Acne Vulgaris", Dematologie, Venerologie, and Verwandte Gebiete 6(7), pp. 320-324.

(56) References Cited

OTHER PUBLICATIONS

Mordon, S., et al (1997), "Thermal Damage Assessment of Blood Vessels in a Hamster Skin Flap Model by Fluorescence Measurement of a Liposome-Dye System", Lasers in Surg. & Med. 20, pp. 131-141.
Mordon, S., et al. (1997), "Selective Laser Photocoagulation of Blood Vessels in a Hamater Skin Flip Model using a Specific ICG Formulation", Lasers Surg. Med. 21(4), pp. 365-373.
Sakurai et al. (2000), "Inhibitory effect of low-level laser irradiation on LPS-stimulated prostaglandin E2 production and cyclooxygnase-2 in human gingival fibroblasts", in Er. J. Oral. Sci., Issue 108:pp. 29-34.
Schindl et al. (Sep. 2000), "Low-Intensity Laser Therapy: A Review", Journal of Investigative Medicine, 48(5).
Schul et al. (2002), "Enhanced repair of cyclobutane pyrimidine dimmers and improved UV resistance in photolyase transgenic mice", The European Molecular Biology Organization (EMBO) Journal 21(17):4719-4729.
ScienceDaily "2002 Nobel Price in Physiology or Medicine: Programmed Cell Death," dated Oct. 8, 2002, located at http://www.sciencedaily.com/releases/2002/10/021008064740.htm Retrieved on Oct. 24, 2007. (5 pages).
Shalita et al., (2001), "Acne PhotoClearing (APC) Using a Novel, High-Intensity, Enhanced, Narrow-Band, Blue Light Source", Clinical Application Notes 9(1).
Pinnell, Sheldon (1985), "Regulation of Collagen Biosynthesis of Ascorbic Acid: A Review" The Yale Journal of Biology and Medicine 58, pp. 553-559.
Tajima, Shingo, et al. (1996) "Ascorbic Acid Preferentially Enhances Type I and III Collagen Gene Transcription in Human Skin Fibroblasts", J. Dermatol. Sci. 11(3), pp. 250-253.
Schaefer, Hans, et al. (1996), "Skin Barrier Principles of Percutaneous Absorption", pp. 153 and 175.
Skinner et al., (1996), "A Preliminary Study of the Effects of Laser Radiation on Collagen Metabolism in Cell Culture", Australian Dental Journal 41(3), pp. 188-192.
Sommer et al. (2001), "Biostimulatory Windows in Low-Intensity Laser Activation: Lasers, Scanners and NASA's Light Emitting Diode Array System", Journal of Clinical Laser Medicine & Surgery 19(1), pp. 29-33.
Sroka et al. (1999), "Effects on the Mitosis of Normal and Tumor Cells Induced by Light Treatment of Different Wavelengths", Lasers in Surgery and Medicine 25, pp. 263-271.
Sumlan et al., "A New Method to Improve Penetration Depth of Dyes into the Follicular Duct: Potential Application for Laser Hair Removal", J. Am. Acad. Dermatol. 41(2), pp. 172-175.
Melo, T. B. (1987), "Uptake of Protoporphyrin and Violet Light Photodestruction of Propionibacterium acnes", Journal of Biosciences 42(1-2), pp. 123-128.
Phillips, Charlotte, et al. (1994), "Effects of Ascorbic Acid on Profileration and Collagen Synthesis in Relation to the Donor Age of Human Dermal Fibroblasts", The Journal of Investigative Dermatology, vol. 103, No. 2.
Srinivasan, V., et al. (1989), "Transdermal Iontophoretic Drug Delivery: Mechanistic Analysis and Application to Polypeptide Delivery", Journal of Pharmaceutical Sciences 78(5).
Srinivasan, V., et al. (1990), "Ionotphoresis of Polypeptides: Effect of Ethanol Pretreatment of Human Skin", Journal of Pharmaceutical Sciences 79(7), pp. 588-591.
Van Breugel et al. (1992), "Power Density and Exposure Time of H-Ne Laser Irradiation are More Important than Total Energy Dose in Photo-Biomodulation of Human Fibroblasts in Vitro", Lasers in Surgery and Medicine 12, pp. 528-537.
Vreman et al. (1998), "Light-Emitting Diodes: A Novel Light Source for Phototherapy", 44, pp. 5.
Vuillaume, et al. (2001), "Real Time RT-PCR Shows Correlation between Retinoid-Induced Apoptosis and NGF-R mRNA Levels", Biochemical and Biophysical Research Communications 289(3):647-652.

Harvey, W., et al. (1975), "The Stimulation of Protein Synthesis in Human Fibroblasts by Therapeutic Ultrasound," Rheumatology and Rehabilitation 14, 237.
Yu, W., et al. (1997), "Effects of Photostimulation on Wound Healing in Diabetic Mice", Lasers Sug. Med. 20(1), pp. 56-63.
Webb, et al., (1996), "Stimulatory Effect of 660 nm Low Level Laser Energy on Hypertrophic Scar-derived Fibroblasts: Possible Mechanisms for Increase in Cell Counts", Lasers in Surgery and Medicine 22, pp. 294-301.
Yu, Wei, et al. (1997), "Improvement of Host Response to Sepsis by Photobiomodulation", Lasers in Surgery and Medicine 21, pp. 262-268.
Wei, Li-Na (2004), "Retinoids and Receptor Interacting Protein 140 (RIP140) in Gene Regulation", Current Medicinal Chemistry 11(12):1527-1532.
Westerhof et al., "Treatment of Vitiligo with UV-B Radiation vs Topical Psoralen Plus UV-A", Arch Dermatol, vol. 133, Dec. 1997, pp. 1525-1528.
Whelan et al., "NASA Light Emitting Diode Medical Applications From Deep Space to Deep Sea", CP552, Space Technology and Applications International Forum 2001, p. 35-45.
Wikipedia Website [http://en.wikipedia.org/wiki/Bandwidth].
Ritschel, Wolfgang, et al. (1989), "Percutaneous Absorption of Coumarin, Griseofulvin and Propranolol Across Human Scalp and Abdominal Skin", Meth and Find Exp. Clin. Pharmacol. 11(10), pp. 643-646.
Joachims, Z. et al. (1987), "Noise-Induced Hearing Loss in Humans as a Function of Serum Mg Concentration", Mag-Bull, pp. 130-131.
Zelickson, et al. (1999), "Pulsed Dye Laser Therapy for Sun Damaged Skin", Lasers in Surgery and Medicine 25, pp. 229-236.
Goldman (Oct. 1999), "FotoFacial is a Pulsed Light Patient Pleaser", Skin and Allergy News.
Newman, J.T., et al. (1992), "Hydrocortisone Phonophoresis: A Literature Review," Journal of the American Podiatric Medical Association, 82(8). pp. 432-435.
Mitragotri, S., et al. (1995), "Ultrasound-Mediated Transdermal Protein Delivery," Science, 269. pp. 850-853.
Office Action dated Jun. 20, 2013 for U.S. Appl. No. 12/583,578.
Response to Final Office Action dated Dec. 3, 2012 for U.S. Appl. No. 12/550,799.
Final Office Action dated Jun. 14, 2007 for U.S. Appl. No. 10/903,483.
Appeal Brief filed Jan. 28, 2008 for U.S. Appl. No. 10/903,483.
European Office Action dated Jul. 21, 2008, directed to EP Application No. 02761449.4.
European Search Report dated Sep. 16, 2005, directed to EP Application No. 02761449.4.
Third-Party Observations dated Sep. 12, 2007, directed to EP Application No. 02749720.5.
Response to Official Notification dated Dec. 3, 2008 for Israeli Patent Application 171311.
Response to Second Office Action dated Nov. 2, 2007 for Chinese Patent Application 200480012575.X.
International Preliminary Examination Report dated Aug. 6, 2004 for Patent Application PCT/US02/26627.
Application to Amend a Complete Specification dated Jul. 24, 2012 for South African Patent Application 2004/1528.
Search Report dated Apr. 26, 2006 for European Patent Application 02792232.7.
Response to Office Action dated Oct. 18, 2010 for European Patent Application 02792232.7.
Response to Office Action dated Jan. 17, 2012 for towards Korean Patent Application 70007060/2004.
Response to Examiner's First Report dated Aug. 5, 2010 for Australian Patent Application 2007212519.
Office Action dated Feb. 29, 2013 for Japanese Patent Application 2008-553383.
Search Report dated Oct. 6, 2010 for European Patent Application 07752016.1.
Office Action dated Feb. 6, 2013 for Japanese Patent Application 2008-557382.
First Examination Report dated Feb. 8, 2007 for European Patent Application 02749720.

(56) References Cited

OTHER PUBLICATIONS

Response to First Examination Report dated Feb. 8, 2007 for European Patent Application 02749720.
Office Action dated Sep. 21, 2011 for Chinese Patent Application 03813556.6.
Response to Office Action dated Sep. 21, 2011 for Chinese Patent Application 03813556.6.
Office Action dated May 16, 2013 for European Patent Application 04779826.9.
Office Action dated Nov. 16, 2012 for Chinese Patent Application 201110210275.4.
Heikkila, H., Stubb, S., & Kiistala, U. (1996). "Nail growth measurement employing nail indentation—an experimental follow-up study of nail growth in situ," Clinical and Experimental Dermatology, 21(2). pp. 96-99.
Zimny, S., & Pfohl, M. (2005). "Healing times and prediction of wound healing in neuropathic diabetic foot ulcers: a prospective study," Experimental and Clinical Endocrinology & Diabetes, 113(2). pp. 90-93.
Martinez, D., et al. "Wound healing response of the medial collateral ligament during hindlimb unweighting in young rats."
Rosenburg, L. (2003). "Wound healing, growth factors," Emedicine.
Mitragotri, S. (2000). "Synergistic effect of enhancers for transdermal drug delivery," Pharmaceutical Research, 17(11). pp. 1354-1359.
Mitragotri, S., et al. (2000). "Analysis of ultrasonically extracted interstitial fluid as a predictor of blood g levels," Journal of Applied Physiology, 89(3). pp. 961-966.
Anvar M.D., et al. (2000). "Vascuar and sromal features in the sky of the lower limb in patens wth critical limb ischaemia," European Journal of Vascular and Endovascular Surgery, 20(2). pp. 125-131.
Eichler, W., et al, (2000). "Changes of inestitial fluid volume in superficial tssues detected by a miniature utrasound device", Journal of Applied Physiology, 89)1). pp. 359-363.
Mitragotri, S., et al. (2000). "Transdermal extraction of analytes using low-frequency ultrasound," Pharmaceutical Research, 17(4). pp. 466-470.
Moli, M., et al, (2000). "Two children with suspected primary vasculitis of messenteric vessels—a case report," Nihon Rinsho Meneki Gakkai Kaishi, 23(2). pp. 148-155.
Mitragotri, S., et al. (2000). "Synergistic effect of low-frequency ultrasound and sodium lauryl sulfate on transdermal transport," Journal of Pharmaceutical Science, 89(7). pp. 892-900.
Mitragotri, S., & Kost, J. (2000). "Low-frequency sonophoresis: A noninvasive method of drug delivery and diagnostics," Biotechnology in Progress, 16(3). pp. 488-492.
Taylor, B.K., et al. (2000). "Opioid inhibition of formalin-induced changes in plasma extravasation and blood flow in rats," Pain, 84(2-3). pp. 263-270.
Fang, J., et al. (1999). "Effect of low-frequency ultrasound on the in vitro percutaneous absorption of clobetasol 17-propionate," International Journal of Pharmaceutics, 191(1). pp. 33-42.
Shoab, S.S., et al. (1999). "Plasma VEGF as a marker of therapy in patients with chronic venous diseases with oral micronised flavonoid fraction- a pilot study," European Journal of Vascular and Endovascular Surgery, 18(4). pp. 334-338.
Meidan, V.M., et al. (1999) "Ultrsound -enhanced diffusion into coupling gel during phonophoresis of 5-fluorourcil," International Journal of Pharmaceutics, 185(2). pp. 205-213.
Terai, M., et al. (1999). "Vascular endothelial growth factor in acute Kawasaki disease," American Journal of Cardiology, 83(3). pp. 337-339.
Singer, A.J., et al. (1999). "The effects of low-frequency ultrasound on *Staphylococcus epidermidis*," Current Microbiology, 38(3). pp. 194-196.
Foldvari, M., et al. (1998) "Liposome encapsulated prostaglandin E1 in erectile dysfunction: Correlation in vitro delivery through foreskin and efficacy in patients," Urology, 52(5). pp. 838-843.

Wu, J., et al. (1998), "Defects generated in human sterum corneum specimens by ultrasound," Ultrasound in Medicine and Biology, 24(5) pp, 705-710.
Liu, J., Lewis, T.N., & Prausnitz, M.R. (1998) "Non-invasive assessment and control of ultrasound-mediated membrane permeabilization," Pharmaceutical Research, 15(6). pp. 918-924.
Pedder, V.V., et al. (1998). "Rationale of noninvasive method of drug administration at the preylmphatic," Med Tekh, 2 pp. 18-23.
Sigfridsson et al. (1995 ), "Electrogenetic light reactions in photosystem I: resolution of electron-transfers rates between the iron-sulfer centers," Proc. National Academy of Science U.S.A., pp. 3456-3462. (Abstract).
Voigt et al. (2002), "Spectral Substructure and Excitonic Interactions in the Minor Photosystem II Antenna Complex CP29 Revealed by Nonlinear Polarization Spectroscopy in Frequency Domain," Biochemistry, pp. 3049-3056. (Abstract).
Dacher et al. (2001), "Combinded NPLC-MS and HPLC-NMR on-line coupling for the separation and determination of lutein and zeaxanthin stereoisomers in spinach and in retina," Analytical Chemistry, pp. 667-674. (Abstract).
Varani et al. (2001) "Inhibtion of type I procollagen synthesis by damages collagen in photoaged skin and by collagenase-degraded collagen in vitro," American Journal of Pathology, pp. 931-941. (Abstract).
Yu et al. (1997) "Photmodulation of oxidative metabolism and electron chain enzymes in rat liver mitochondra," Photochem. Photobiol., pp. 866-871. (Abstract).
Quan et al. (2002), "Connective tissue growth factor: expression in human skin in vivo and inhibition by ultraviolet radiation," Journal of Investigative Dermatology, pp. 402-408. (Abstract).
Boudjelal et al. (2002), "Retinoid Signaling Is Attenuated by Protassome-Mediated Degradation of Retinoid Receptors in Human Keratinocyte HaCaTCells," Exp. Cell. Res., pp. 130-137. (Abstract).
Loschinger et al. (1998), "Stimulation of protein kinase A activity and induced terminal differentiation of human skin fibroblasts in culture by low-frequency electromagnetic fields," Toxicol, Lett., pp. 369-376. (Abstract).
Bourguignon, GJ. and Bourguignon, LY., (1987). "Electric stimulation of protein and DNA synthesis in human fibroblasts," FASBERS J., pp. 398-401 (Abstract).
Bourguignon et al. (1989), "Electric stimulation of human fibroblasts causes an increase in Ca2+influx and the exposure of additional insulin receptors," Journal of Cellular Physiology, pp, 379-385. (Abstract).
Quan et al. (2001), "Ultraviolet irradiation blocks cellular responses to transforming growth factor-beta by down-regulating its type-II receptor and inducing Smad7," Journal of Biological Chemistry, pp. 26349-26356, (Abstract).
Neudecker, B.A., et al. (2004) "Abberant Serum Hyaluronan and Hyaluronidase Levels in Scleroderma," The British Journal of Dermatology pp. 469-476.
Formby, Bent, et al. (2002) "Lactate Stimulates Hyaluronan and CD44 Expression in Cultured Fibroblasts: the Warburg Effect Revisited," Experimental Cell Research May 15, 2002;276(1):24-31.
Stern, Robert. (2001) "Minireview on the Mammalian Hyaluronidases: Introductory Remarks" pub. by Elsevier Science B.V., Matrix Biology p. 497.
Csoka, Antonei, B. (2001) "Minireview the Six Hyaluronidase-like Genes in Human and Mouse Genomes" pub. by Elsevier Science B.V. Matrix Biology pp. 499-508.
Boh, Erin E. (2001) "Free Radicals and Aging Skin" Cosmetic Dermatology vol. 14 No. 12 Dec. 2001 pr. 37-40.
Lubart, R. et al. (1992) "Effect of Light on Calcium Transport in Bull Sperm Cells" Journal of Photochemuistry Photobiology B. Sep. 15, 1992;15(4):337-41.
Webster, Guy (2001) "Acne Pathogenesis & update on Therapy" Jujisawa Healthcare, Inc. Lectureship Series IN Dermatology [pamphlet] pp. 1-24.
Loschinger, Monika (1998) "Stimulation of Protein Kinase a Activity and Induced Terminal Differentiation of Human Skin Fibroblasts in Culture by Low-Frequency Electromagnetic Fields" Toxicol Lett. Aug. 1998; pp. 96-97;369-76.

(56) References Cited

OTHER PUBLICATIONS

Bedi, Monika K. (2002) "Herbal therapy in dermatology" Archives of Dermatology Feb. 2002 pp. 138(2):232-42.
Yu, Wei. (1997) "Photomodulation of Oxidative Metabolism and electron Chain Enzymes in Rat Liver Mitochondria" Photochemistry and Photobiology. Dec. 1997;66(6):866-71.
Barber, James (2002) "Short communication: P680 What is it and Where is it?" Bioelectrochemistry, vol. 55, No. 1, Jan. 2002, pp. 135-138(4).
Matsuad, Tatsuru et al. (2002) "Biosynthesis and distribution of Chlorophyll Among the Photosystems During recovery of the Green Alga Dunaliella Salina From Irradiance Stress" Plant Physiology. Feb. 2002;128(2):603-14.
De Mattei, M, et al. (2001) "Effect of Pusled Electromagnetic Fields on human Articular Chodrocyte Proliferation" Connective Tissue Research 2001:42(4):269-79.
Krishtalik, Li et al. (2000) "Effects of Medium Polarization and Pre-Existing Field on Activation Energy of Enzymatic Charge-Transfer Reactions" Biochimica Biophysica Acta. Jul. 20, 2000;1459(1):88-105.
Edwards, AM, Silva, E. "Effect of Visible Light on Selected Enzymes, Vitamins and Amino Acids" Journal of Photochemistry Photobiology B. Oct. 2001;63(1-3):126-31.
Sommer, Andrei P. "Abstracts From the 1st International workshop on Nearfield Optical Analysis, Reisenberg, Germany, Nov. 2000" Journal of Clinical Laser Medicine & Surgery vol. 19 No. 2 2001.
Ishigaki, Y., et al. (1999). "Development and Characterizaton of a DNA Solar Dosimeter," Jounal of Photochemistry and Photobiology, 50. pp. 184-188.
Gross, A. (1999). "Entering the Japanese Medical Device Market: The latest trends mean even better opportunities for foreign medical technology manufacturers," Medical Devicelink, Accessed: Dec. 15, 2001.
Gross, A., & Dyson, P. (1996). "Changing Regulatory Climate Improves Korean Market of U.S. Companies," Medical Device and Diagnostic Industry.
LeDoux, S.P., & Wilson, G.L. (2001). "Base Excision Repair of Mitochondrial DNA Damage in Mammalian Cells," Progress in Nucleic Acid Research and Molecular Biology, 66. pp. 273-284.
Turnbull, D., & Lightowlers, R. (2001). "Might Mammalian Mitochondria Merge?" Nature Medicine, 7(6). pp. 895-896.
Nakada, K., et al. (2001). "Inter-mitochondrial complementation: Mitochondria-specific system preventing mice from expression of disease phenotypes by mutant mtDNA," Nature Medicine, 7(8). pp. 934-940.
Vogel, W.F. (2001) "Collagen-receptor signaling in health and disease," European Journal of Dermatology, 11(6). pp. 506-514.
Curat, C., et al. (2001) "Mapping of eptiopes in discoidin domain receptor 1 critical for collagen binding," Journal of Biological Chemistry, 6(49).
Hou, G., Vogel, W., & Bendeck M.P. (2001), "The discoidin domain receptor tyrosine kinase DDR1 in arterial wound repair," Journal of Clinical Investigation, 107(6), pp. 727-735.
Chin, G.S., et al. (2000), "Cellular signaling by tyrosine phosphorylation in keloid and normal human dermal fibroblasts," Plastic Reconstructive Surgery, 106(7). pp. 1532-1540.
Weiner, H.L., et al. (2000). "Consistent and selective expression of the discoidin domain receptor-1 tyrosine kinase in human brain tumors," Neurosurgery, 47(6), pp. 1400-1409.
Chin, G.S., et al. (2000). "Differential expression of receptor tyrosine kinases and Shc in fetal and adult rat fibroblasts: Toward defining scarless versus scarring fibroblast phenotypes," Plastic Reconstructive Surgery, 105(3). pp. 972-979.
Vogel, W., et al. (2000). "Discoidin domain receptor 1 is activated independently of beta 1 integrin," Journal of Biological Chemistry 275(8). pp. 5779-5784.
Vogel, W. (1999). "Discoidin domain receptors: Structural relations and functional implications, " FASEB Journal, 13. pp. 77-82.
Norman, J.T., & Fine, L.G. (1999). "Progressive renal disease: Fibroblasts, extracellular matrix, and integrins," Experimental Nephrology, 7(2). pp. 167-177.
Shrivastava, A., et al. (1997). "An orphan receptor tyrosine kinase family whose members serve as nonintegrin collagen receptors," Molecular Cell, 1(1). pp. 25-34.
Vogel, W., et al. (1997). "The discoidin domain receptor tyrosine kinases are activated by collagen, " Molecular Cell, 1 (1). pp. 13-23.
Sakuma, S., et al. (1996). "Receptor protein tyrosine kinase DDR is up-regulated by p53 protein," FEBS Letters, 2. pp. 398, 165-169.
Hardell, L., et al. (2001). "Ionizing radiation, cellular telephones and the risk for brain tumors," European Journal of Cancer Prevention, 10(6). pp. 523-529.
Seishima, M., Oyama. Z., & Yamamura, M. (2002). "Cellular phone dermatitis." Archives of Dermatology, 138(2). pp. 272-273.
Di Carlo, A., et al., (2002). "Chronic electromagnetic field exposure decreases HSP70 levels and lowers cytoprotection," Journal of Cellular Biochemistry, 84(3), pp. 447-454.
French, P.W., et al. (2001), "Mobile phones, heat shock proteins and cancer," Differentiation, 67(4-5), pp. 93-97.
Frumkin, H., et al. (2001). "Cellular phones and risk of brain tumors," CA: A Cancer Journal for Clinicians, 51(2). pp. 137-141.
Moustafa, Y.M., et al. (2001), "Effects of acute exposure to the radiofrequency fields of cellular phones on plasma lipid peroxide and antioxidase activities in human erythrocytes, "Journal of Pharmaceutical and Biomedical Analysis, 26(4). pp. 605-608.
Chiladakis, J.A., et al. (2001). "In-vivo testing of digital cellular telephones in patients with implantable cardioverter-defibrillators," European Heart Journal, 22(15). pp. 1337-1342.
Santini, R., et al. (2001). "Symptoms reported by mobile cellular telephone users." Pathological Biology, 49(3). pp. 222-226.
Roti, J.L., et al. (2001). "Neoplastic transformation in C3H 10T(1/2) cells after exposure to 835.62 MHz FDMA and 847.74 CDMA radiations," Radiation Research, 155(1-2). pp. 239-247.
Wainwright, P. (2000). "Thermal effects of radiation from cellular telephones," Physics in Medicine and Biology, 152 (3). pp. 293-302.
Adey, W.R., et al. (1999). "Spontaneous and nitrosourea-induced primary tumors of the central nervous system in Fischer 344 rats chronically exposed to 836 MHz modulated microwaves," Radiation Research, 152(3). pp. 293-302.
Robert, E. (1999). "Intrauterine effects of electromagnetic fields— (low frequency, mid-frequency RF, and microwave): A review of epidemiologic studies,"Teratology, 59(4). pp. 292-298.
De Seze. R., Fabbro-Peray, P., Miro, L. (1998). "GSM radiocellular telephones do not disturb the secretion of antepituitary hormones in humans," Bioelectromagnetics, 19(5). pp. 271-278.
Malyapa, R.S., et al. (1997), "Measurement of DNA damage after exposure to electromagnetic radiation in the cellular phone communication frequency band (835.62 and 847.74 MHz)," Radiation Research, 148(6). pp. 618-627.
Litovitz, T.A., et al. (1997). "Bioeffects induced by exposure to microwaves are mitigated by superposition of ELF noise," Bioelectromagnetics. 18(6). pp. 422-430.
Omura, Y., & Losco, M. (1993) "Electra-magnetic fields in the home environment (color TV, computer monitor, microwave oven, cellular phone. etc) as potential contributing factors for the induction of oncogen C-fos Ab1, oncogen C-fos Ab2, integrin alpha 5 beta 1 and development of cancer, as well as effects of microwave on amino acid composition of food and living human brain," Acupuncture and Electro-Theraputics Research, 18(1). pp. 33-73.
Knave, B. (2001). "Electromagnetic fields and health outcomes," Annals Academy of Medicine Singapore, 30(5). pp. 489-493.
De Seze, R., et al. (1999). "Evaluations in humans of the effects of radiocellular telephones on the circadian patterns of melatonin secretion, a chronobiological rhythm marker," Journal of Pineal Research, 27(4). pp. 237-242.
Fluhr, J.W., et al. (1999). "In-vitro and in-vivo efficacy of zinc acetate against propionibacteria alone and in combinaton with erythomycin," Zentralbl Bakteriol, 289(4). pp. 445-456.
Itoh, Y., et al. (2001). "Photodynamic therapy of acne vulgaris with topical delta-aminolaevulinic acid and incoherent light in Japanese patients," British Journal of Dermatology, 144(3). pp. 575-579.

(56) References Cited

OTHER PUBLICATIONS

Lang, K., et al. (2001). "Aminolevulinic acid: Pharmacological profile and clinical indication," Expert Opinion on Drug Discovery, 10(6). pp. 1139-1156.
Ashmead, H.D. "The Need for Better Nutrition in our Food." Clearfield, Utah. USA. pp. 1-20.
Van Remmen, H. & Richardson. A. (2001). "Oxidative Damage to Mitochondria and Aging," Experimental Geology 36, pp. 957-968.
Rice, B.W., et al. (2001). "In Vivo Imaging of Light-emitting Probes," Journal of Biomedical Optics 6(4), pp. 432-440.
Moretti, M. (2001). "ICN Develops Integrated Skin Treatment Package," Aesthetic Buyers Guide Nov. 2001.
Neudecker, B.A., Stern, R., & Connolly, M.K. "Aberrant Serum Hyaluronan and Hylauronidase Levels in Scleroderma," Department of Pathology and Dermatology, School of Medicine, University of California San Francisco.
Leyden, J., et al. (1999) "Finasteride in the Treatment of Men with Frontal Male Pattern Hair Loss," Jounal of the American Academy of Dermatology 40(6). pp. 930-937.
Sommer, A.P, et al. (2001). "Biostimulatory Windows in Low-Intensity Laser Activation: Lasers, Scanners, and NASA's Light-Emitting Diode Array System," Journal of Clinical Laser Medicine and Surgery 19(1). pp. 29-33.
Troy, T. (2002). "Fluorescent Pulsed Light Makes Foray," Dermatology Times Jan. 2002.
Panteleyev, A., Jahoda, C., & Christiano, A. (2001). "Hair Follicle Predetermination," Journal of Cell Science 114. pp. 3419-3431.
Yoon, J.H., et al. (2000). "The DNA Damage Spectrum Produced by Simulated Sunlight," Academic Press, pp. 681-693.
Draper, B., et al. (2002). "MNPs and TIMP-1 are Differentially Expressed Between Acute Murine Excisional and Laser Wounds," Lasers in Surgery and Medicine 30, pp. 106-116.
Takemura et al.,(1998), "Enhanced Interleukin 6 Production by Cultured Fibroblasts from Patients with Systemic Sclerosis in Response to Platelet Derived Growth," The Journal of Rheumatology, pp. 1534-1539.
Czuwara et al. (2001), "Differental regulaton of transforming growth factor-β receptors type I and II by platelet-derived growth factor in human dermal fibroblasts," British Journal of Dermatology, 569-575.
Loftsson et al. (1995), "Fatty acids from cod-liver oil as skin penetration enhancers," Die Pharmazie, pp. 271-773.
Stahl et al. (2000), "Carotenoids and carotenoids plus vitamin E protect against ultraviolet light-induced erythema in humans," The American Clinical Journal of Nutrition, pp. 795-798.
Gambichler et al. (2001), "Ultraviolet protection by summer textiles. Ultraviolet transmission measurements verified by termination of the minimal erythema dose with solar simulated radiation," British Journal of Dermatology, pp. 484-489.
Stahl et al. (2001), "Dietary Tomato Pasta Protects against Ultraviolet Light-Induced Erythema in Humans," Biochemical and Molecular Action of Nutrients Research Communication, pp. 1449-1451.
Lee et al. (2000), "Carotenoid Supplementation Reduces Erythema in Human Skin After Simulated Solar Radiation Exposure," Society of Experimental Biology and Medicine, pp. 170-174.
Moy et al. (2000), "Incresed Glycosaminolycans Production in Sclersoing Basal Cell Carcinoma-Derived Fibrolasts and Stimulation of Normal Skin Fibroblast Glycosaminoglycans Production by a Cytokine-Derived from Sclerosing Basal Cell Carcinoma," Dermatolgoic Surgery, pp. 1029-1035.
Takehara. K. (2000), "Grown regulation of skin fibroblasts." Journal of Dermatologial Science, pp. 70-74.
Loftsson, T. (1989), "Effect of choline esters and oleic acid on the penetration of acyclovir, estradiol, hydrocortisone nitroglycerin, retinoic acid and trifluorothymidine across hairless mouse skin in vitro," Acta. Pharm. Nord., pp. 279-286.
Masson et. al. (2000), "Marine lipids for prodrugs, soft compounds and other pharmaceutical applications," Pharmazie, pp. 172-177.
Gross et al. (1978) "Comprehensive compilation of empirical ultrasonic properties of mammalian tissues," Journal of the Acoustical Society of America, pp. 423-457.

Fei et al. (1986) "Ultrasonic backscatter from bovine tissues: Varation with pathology," Journal of the Acoustical Society of America, pp. 166-172.
Fei, D and Shung, K. (1986) "Ultrasonic backscatter from bovine tissues," Journal of the Acoustical Society of America, pp. 871-876.
Chivers, R. and Parry R.(1978), "Ultrasonic velocity and attenuation in mammalian tissues," Journal of the Acoustical Society of America, pp. 940-954.
de Weerd et al. (2002) "Pathways for Energy transfer in the Core Light Harvesting Complexes CP43 and CP 47 of Photosystem II," Biophysical Journal, pp. 1586-1597.
Fluhr et al. (1999), "In-vitro and in-vivo Efficacy of Zinc Acetate against Propionbacteria Alone and in Combination with Erythromycin," Zent. bl. Bakerologie, pp. 445-456.
Lang et al. (2001), "Aminolevulinic acid: pharmacological profile and clinical indication," Expert Opinion Investigative Drugs, pp. 1139-1156.
Yakushevska et al. (2001). "Supermolecular organization of photosystem II and its associated light-harvesting antenna in *Arabidopsis thalinana*." European Journal of Biochemistry, pp. 6020-6028.
Polivka et al. (2002), "Carotenoid Si State in a Recombinant Light-Harvesting Complex of Photosystem II," Biochemistry, pp. 439-450.
Vander Meulen et al. (2002), "Calcium Depletion Modifies the Structure of the Photosystem II O2-Evolving Complex" Biochemistry, pp. 958-966.
Park et al.(2000), "Epidermal Growth (EGF) Antagonizes Transforming Growth Factor (TGF)-β1-Induced Collagen Lattice Contraction by Human Skin Fibrolasts," Biological and Pharmaceutical Bulletin, pp. 1517-1520.
Diffey et al. (2000). "In vitro assessment of the broad-spectrum ultraviolet protection of sunscreen products," Journal of the American Academy of Dermatology, pp. 1024-1035.
Zhu et al. (1997), "Photo-Irradiation Improved Functional Preservation of the Isolated Rat Heart," Lasers in Surgery and Medicine, pp. 332-339.
Yu et al. (1997) "Impovement of Host Response to Sepsis by Photobiomodulaton," Lasers in Surgery and Medicine, pp. 262-268.
Shapiro, J and Price, V. (1998), "Hair Regrowth: Therapeutic Agents," Dermatologic Therapy, pp. 341-356.
El Sayed, S and Dyson, M. (1990), "Comparision of the Effect of Multiwavelength Light Produced by a Cluster of Semiconductor Diodes and of Each Individual Diode on mast Cell Number and Degranulation in Intact and Injured Skin," Lasers in Surgery and Medicine, pp. 559-568.
Huang et al. (2002), "Two-Photon Fluorescence Spectroscopy and Microscopy of NAD(P)H and Flavoprotein," Biophysical Journal, pp. 2811-2825.
Yamazaki et al. (1992), "Selective Chemical Modification of Amino Acids Residues in the Flavin Adrenie Dinucleotide Binding Site of Nadph-Ferredoxin Reductase," International Journal of Biochemistry, pp. 223-228.
Andersson et al. (1998), "Autofluoresence of living cells," Journal of Microscopy, pp. 1-7.
Chen et al. (2002), "New Technology for Deep Light Distribution in Tissue for Phototherapy," The Cancer Journal, pp. 154-163.
Baena-Gonzalez et al. (2001), "Cloroplast Transcription at Different Light Intensities. Glutathione-Mediated Phosphorylation of the Major RNA Polymerase Involved in Redox-Regulated Organellar Gene Expression," Plant Physiology, pp. 1044-1052.
Cheng, K. and Goldman, R. (1998), "Electronic Field and Proliferation in a Derma Wound Model: Cell Cycle Kinetics," Bioelectromagnetics, 68-74.
Stough et al. (2002), "Finasteride improves male pattern hair loss in a randomized study in indentical twins," European Journal of Dermatology, pp. 32-37.
Todd et al. (2001), "Electrical Stimulation of Transforming Growth Factor-β1 Secretion by Human Dermal Fibroblasts and the U937 Human Monocyctic Cell Line," pp. 693-701.
Unholzer, A and Korting, H. (2002), "High Frequency Ultrasound in the Evaluation of Pharmacological Effects on the Skin," Skin Pharmacology and Applied Skin Physiology, pp. 71-84.

(56) References Cited

OTHER PUBLICATIONS

Pelle et al. (2002), "Cigareete Smoke-Inducted Lipid Peroxidation in Human Skin and its Inhibition by Topically Applied Antioxidants," Skin Pharmacology and Applied Skin Physiology, pp. 63-68.

Garbaers et al. (2001), "Mössbauer study of iron centers in D1/D2/Cyt b 559 complexes isolated from photostem II of spinach," European Biophysics Journal, pp. 485-493.

O.Ishiawa et al. (1997) "Morphological and biochemical analyses on fibroblasts and self-produced collagens in a novel three dimensional culture," British Journal of Dermatology, pp. 6-11.

Harmon, C. and Nevins, T. (1994), Biophasic Effect of 1, 25-Dihyoxyvitamin D on Human Hair Follicle Growth and Hair Fiber Production in Whole Organ Cultures, Journal of Investigative Dermatology pp. 318-322.

Reiss, S. (2002), "Photodynamic Therapy: Reaching Beyond Cancer," Biophotonics International Journal, pp. 48-54.

Lahjomri et al. (1997), "Pulsed Photoacoustic Study of the Diffusion of Chromophores in Human Skin," Photochemistry and Photobiology, pp. 292-302.

Agramonte, A. (2001), "The Inside History of a Great Medical Discovery," Military Medicine, pp. 66-78.

Tsukahara et al. (2001), "Dirunal variation affects age-related profile in skin thickness," Journal of Cosmetic Science, pp. 391-397.

Ernst, E. and Huney, A. (2000), "Tea Tree Oil: A system Review of Randomzed Clinical Trials," Research Complemetary Medicine, pp. 17-20.

Masuda et al. (2002), "Biosynthesis and distribution of chlorophyll among the photosystems during recovey of the green alga Dunaliella salina from irradiance stress," Plant Physiology, pp. 603-614. (Abstract).

Joet et al. (2002), "Cyclic Electron Flow around Photosystem I in C(C) Plants. In Vivo Control byu the Redox State of Chloroplasts and Involvement of the NADH-Dehydroense Complex," pp. 760-769. (Abstract).

Christen et al. (2000), "Delayed Fluorescence emitted from the light harvesting complex II and photosystem II of higher plants in the 100 ns-5 micros time domain," FEBS Lett., pp. 103-106. (Abstract).

de Wijn et al. (2001), "Secondary stabilization reactions and proton-coupled electron transport in photosytem II investigated by electroluminescence and fluorescence spectroscopy," Biochemistry, pp. 5821-5834.

Hou et al. (2001), "Thermodynamics of electron transfer in oxygenic photosystem reaction centers; a pulsed photoacoustic study of electron transfer in photosystem I reveals a similarity to bacertial reaction centers in both volume change and entropy," Biochemistry, pp. 7109-7016.

Jarrousse, F., et al. (2001). "Identification of clustered cells in human hair follicle responsible for MMP-9 gelatinolytic activity: Consequences for the regulation of hair growth." International Journal of Dermatology, 40(6), pp. 385-392.

Langbein, et al. (2001). "Figure 8." Journal of Biological Chemistry, 276(37), pp. 35123.

King, A., et al. (2004). "Mitochondria-derived reactive oxygen species mediate blue light-induced death of retinal pigment epithelial cells." Photochemistry and Photobiology, 79(5), pp. 470-475.

"The EpiOcular™ Model." http://www.mattek.com/pages/products/epiocular. Mattek Corporation. Accessed: Apr. 27, 2005.

"Folliquant®: A range of in vivo assays of hair follicle damage and alopecia." EpiStem® LTD. Copyright 2003 Epistem Ltd.

Davis, S.C., et al. (2004). "To examine the effect of GentleWaves LED photomodulation device on deep partial thickness wound healin." Preliminary Protocol: Deep Partial thickness wound study. Department of Dermatology and Cutaneous Surgery, University of Miami School of Medicine.

"Virulite CS® . . . The Original Cold Sore Machine." http://www.virulite.com/technical_information.html Date accessed: Jan. 26, 2008.

Christensen, B. (2008). "Forced resonance ultra-short pulse laser kills viruses dead." Technovelogy.com Where Science Meets Fiction, http://www.technovelogy.com/ct/Science-Fiction-News.asp?NewsNum=1311. Date Accessed: Jan. 26, 2008.

"Visual Signal Transduction," Biocarta http://www.biocarta.com/pathfiles/h_rhodospinPathway.asp Date Accessed: Aug. 29, 2005.

Epstein, P. (2007). "Trials that matter: Two faces of progress in the treatment of age-related macular degeneration." Annals of Internal Medicine, 146(7). pp. 532-534.

Ostler, E.L. et al. (2000) "Telomerase and the cellular lifespan: Implications of the aging process." Journal of Pediatric Endocrinology and Metabolism, 13(6), pp. 1467-1476.

Lou, H. J. et al.(2002). "Lighting the way: Molecular beacons offer a highly sensitive, flexible method for DNA analysis." Spie's OEMagazine, February, pp. 23-25.

"The Relief Light: A sensible alternative to 'soft' laser technology." Retrieved: http://www.fredomunlimited.net/relief%20light.htm Date Accessed: Feb. 9, 2002.

Stern, R. et al. (2001)."Hyaluronidase can modulate expression of CD44." Experimental Cell Research, 265, pp. 1-10.

Mio, K. et al. (2000). "Evidence that the serum inhibor of hyaluronidase may be a member of the inter-a-inhibitor family." Journal of Biological Chemistry, 275(42), pp. 32413-32421.

Mortimer, A.J., & Dyson, M. (1988). "The effect of therapeutic ultrasound on calcium uptake in fibroblasts."Ultrasound in Medicine and Biology, 14(6), pp. 499-506.

Office Action issued Sep. 13, 2013 in U.S. Appl. No. 12/550,746.

Canadian Office Action dated May 30, 2013 issued in Canadian Patent Application No. 2,533,129.

Translation of amended claims filed in response to Second/Final Notice of Reasons for Rejection dated Feb. 20, 2013 issued in Japanese Patent Application No. 2008-553383.

Translation of Written Amendment filed Aug. 6, 2013 in response to Second/Final Notice of Reasons for Rejection dated Feb. 6, 2013 issued in Japanese Patent Application No. 2008-557382.

Response filed May 31, 2013 to office action dated Nov. 16, 2012 in Chinese Patent Application No. 201110210275.4.

Decision on Rejection issued Jun. 28, 2013 in Chinese Patent Application No. 201110210275.4.

European Office Action dated Oct. 3, 2013 issued in European Patent Application No. 02792232.7.

Canadian Office Action dated Aug. 23, 2013 issued in Canadian Patent Application No. 2644219.

Japanese Office Action dated Dec. 2, 2013 issued in Divisional Japanese Patent Application No. 2009-236857.

Canadian Office Action dated Oct. 8, 2013 issued in Canadian Patent Application No. 2640203.

Japanese Office Action dated Jan. 8, 2014 issued in Japanese Application No. 2008-557382, filed Mar. 2, 2007, GentleWaves LLC.

Japanese Office Action dated Feb. 10, 2014 issued in Japanese Application No. 2008-553383, filed Feb. 2, 2007, GentleWaves LLC.

Non-Final Rejection dated Sep. 22, 2009 for U.S. Appl. No. 11/116,434.

Response to Final Office Action dated Jan. 5, 2009 for U.S. Appl. No. 11/116,434.

Final Rejection dated Jan. 5, 2009 for U.S. Appl. No. 11/116,434.

Amendment to Non-Final Rejection dated Feb. 20, 2008 for U.S. Appl. No. 11/116,434.

Non-Final Rejection dated Feb. 20, 2008 for U.S. Appl. No. 11/116,434.

Amendment to Final Office Action dated Jun. 29, 2007 for U.S. Appl. No. 11/116,434.

Final Rejection dated Jun. 29, 2007 for U.S. Appl. No. 11/116,434.

Amendment to Non-Final Rejection dated Jan. 9, 2007 for U.S. Appl. No. 11/116,434.

Non-Final Rejection dated Jan. 9, 2007 for U.S. Appl. No. 11/116,434.

Response to Miscellaneous Action Regarding Drawing Inconsistency dated Aug. 24, 2005 for U.S. Appl. No. 09/876,157.

Miscellaneous Action Regarding Drawing Inconsistency dated Aug. 24, 2005 for U.S. Appl. No. 09/876,157.

Amendment to Non-Final Rejection dated Apr. 8, 2004 for U.S. Appl. No. 09/876,157.

(56) References Cited

OTHER PUBLICATIONS

Non-Final Rejection dated Apr. 8, 2004 for U.S. Appl. No. 09/876,157.
Response to Restriction Requirement dated Jul. 22, 2003 for U.S. Appl. No. 09/876,157.
Requirement for Restriction/Election dated Jul. 22, 2003 for U.S. Appl. No. 09/876,157.
Preliminary Amendment filed Jan. 7, 2002 for U.S. Appl. No. 09/876,157.
Amendment to Final Office Action dated Jan. 25, 2008 for U.S. Appl. No. 11/783,538.
Final Rejection dated Jan. 25, 2008 for U.S. Appl. No. 11/783,538.
Amendment to Non-Final Rejection dated Aug. 22, 2007 for U.S. Appl. No. 11/783,538.
Non-Final Rejection dated Aug. 22, 2007 for U.S. Appl. No. 11/783,538.
Non-Final Rejection dated Dec. 30, 2005 for U.S. Appl. No. 09/819,082.
Preliminary Amendment filed Feb. 15, 2001 for U.S. Appl. No. 09/819,082.
Amendment After Notice of Allowance filed Aug. 1, 2008 for U.S. Appl. No. 09/819,083.
Amendment to Final Office Action dated Jan. 24, 2008 for U.S. Appl. No. 09/819,083.
Final Rejection dated Jan. 24, 2008 for U.S. Appl. No. 09/819,083.
Amendment to Non-Final Rejection dated May 15, 2007 for U.S. Appl. No. 09/819,083.
Non-Final Rejection dated May 15, 2007 for U.S. Appl. No. 09/819,083.
Amendment to Final Office Action dated Dec. 22, 2006 for U.S. Appl. No. 09/819,083.
Final Rejection dated Dec. 22, 2006 for U.S. Appl. No. 09/819,083.
Amendment to Non-Final Rejection dated Mar. 24, 2006 for U.S. Appl. No. 09/819,083.
Non-Final Rejection dated Mar. 24, 2006 for U.S. Appl. No. 09/819,083.
Advisory Action dated Dec. 1, 2005 for U.S. Appl. No. 09/819,083.
Amendment to Final Office Action dated Sep. 1, 2005 for U.S. Appl. No. 09/819,083.
Final Rejection dated Sep. 1, 2005 for U.S. Appl. No. 09/819,083.
Amendment to Non-Final Rejection dated Dec. 15, 2004 for U.S. Appl. No. 09/819,083.
Non-Final Rejection dated Dec. 15, 2004 for U.S. Appl. No. 09/819,083.
Amendment to Non-Final Rejection dated Jan. 14, 2004 for U.S. Appl. No. 09/819,083.
Non-Final Rejection dated Jan. 14, 2004 for U.S. Appl. No. 09/819,083.
Preliminary Amendment filed Feb. 15, 2001 for U.S. Appl. No. 09/819,083.
Non-Final Rejection dated Feb. 19, 2003 for U.S. Appl. No. 09/819,083.
Amendment to Non-Final Rejection dated Feb. 19, 2003 for U.S. Appl. No. 09/819,083.
Preliminary Amendment filed May 2, 2005 for U.S. Appl. No. 11/119,378.
Non-Final Rejection dated Jun. 5, 2006 for U.S. Appl. No. 11/119,378.
Amendment to Non-Final Rejection dated Jun. 5, 2006 for U.S. Appl. No. 11/119,378.
Preliminary Amendment filed Aug. 29, 2005 for U.S. Appl. No. 11/212,916.
Non-Final Rejection dated Sep. 25, 2007 for U.S. Appl. No. 11/212,916.
Amendment to Non-Final Rejection dated Sep. 25, 2007 for U.S. Appl. No. 11/212,916.
Final Rejection dated Mar. 25, 2008 for U.S. Appl. No. 11/212,916.
Non-Final Rejection dated Jun. 19, 2008 for U.S. Appl. No. 11/332,517.
Non-Final Rejection dated Dec. 19, 2002 for U.S. Appl. No. 09/986,367.
Amendment to Non-Final Rejection dated Dec. 19, 2002 for U.S. Appl. No. 09/986,367.
Final Rejection dated Aug. 12, 2003 for U.S. Appl. No. 09/986,367.
Amendment to Final Office Action dated Aug. 12, 2003 for U.S. Appl. No. 09/986,367.
Advisory Action dated Mar. 8, 2004 for U.S. Appl. No. 09/986,367.
Non-Final Rejection dated Sep. 22, 2004 for U.S. Appl. No. 09/986,367.
Amendment to Non-Final Rejection dated Sep. 22, 2004 for U.S. Appl. No. 09/986,367.
Non-Final Rejection dated Jun. 26, 2008 for U.S. Appl. No. 11/366,811.
Non-Final Rejection dated Jun. 25, 2008 for U.S. Appl. No. 11/346,622.
Amendment to Non-Final Rejection dated Jun. 25, 2008 for U.S. Appl. No. 11/346,622.
Final Office Action dated Jan. 6, 2010 for U.S. Appl. No. 11/346,622.
Response to Final Office Action dated Jan. 6, 2010 for U.S. Appl. No. 11/346,622.
Advisory Action dated Mar. 12, 2010 for U.S. Appl. No. 11/346,622.
U.S. Office Action dated Sep. 30, 2010 for U.S. Appl. No. 11/346,622.
Response to U.S. Office Action dated Sep. 30, 2010 for U.S. Appl. No. 11/346,622.
U.S. Final Office Action dated Jun. 13, 2011 for U.S. Appl. No. 11/346,622.
Response to U.S. Final Office Action dated Jun. 13, 2011 for U.S. Appl. No. 11/346,622.
Amendment to Non-Final OA dated Sep. 22, 2009 for U.S. Appl. No. 11/116,434.
Final Rejection dated Sep. 15, 2010 for U.S. Appl. No. 11/116,434.
Response to Final Office Action dated Sep. 15, 2010 for U.S. Appl. No. 11/116,434.
Advisory Action dated Dec. 22, 2010 for U.S. Appl. No. 11/116,434.
Appeal Brief dated Aug. 15, 2011 for U.S. Appl. No. 11/116,434.
Office Action dated May 25, 2011 for U.S. Appl. No. 12/753,207.
Response to Office Action dated May 25, 2011 for U.S. Appl. No. 12/753,207.
Office Action dated Jul. 21, 2011 for U.S. Appl. No. 12/583,578.
Response to U.S. Office Action dated Jul. 21, 2011 for U.S. Appl. No. 12/583,578.
Final Office Action dated Apr. 11, 2012 for U.S. Appl. No. 12/583,578.
Response to Final Office Action dated Apr. 11, 2012 for U.S. Appl. No. 12/583,578.
U.S. Office Action dated May 10, 2011 for U.S. Appl. No. 12/550,749.
Response to Office Action dated May 10, 2011 for U.S. Appl. No. 12/550,749.
Final Office Action dated Jan. 18, 2012 for U.S. Appl. No. 12/550,749.
Response to Final Office Action dated Jan. 18, 2012 for U.S. Appl. No. 12/550,749.
Office Action dated May 11, 2011 for U.S. Appl. No. 12/550,799.
Response to Office Action dated May 11, 2011 for U.S. Appl. No. 12/550,799.
Final Office Action dated Dec. 3, 2012 for U.S. Appl. No. 12/550,799.
Illel, Brigette, et al. (1991), "Follicles Play an Important Role in Percutaneous Absorption," Journal of Pharmaceutical Sciences 80(5).
Finlay, A., et al., "A Fluorescence Photographic Photomeric Technique to assess Stratum Corneum Turnover Rate and Barrier Function in Vivo", British Journal of Dermatology, 1982, 107, 35-42.
Burgess, "Researchers Identify Key to Phototropism", Biophotonics International, Nov./Dec. 1999, pp. 22-23.
Green, C., et al. (1988), "311 nm UVB Phototherapy: an Effective Treatment for Psoriasis", Br J Dermatol. 119, pp. 694-696.
Callaghan et al. (1996), "Reactive Oxygen Species Inducible by Low-intensity Laser Irradiation Alter DNA Synthesis in the Hemopoietic Cell Line", U937, Lasers Surg. Med. 19(2):201-206.

(56) References Cited

OTHER PUBLICATIONS

Castro (Sep. 1983), "Effects of the Nd:YAG Laser on DNA Synthesis and Collagen Production in Human Skin Fibroblast Cultures", Annals of Plastic Surgery 11, pp. 3.
Ceccherelli et al. (1989), "Diode Laser in Cervical Myofascial Pain: A Double-blind Study Versus Placebo," The Clinical Journal of Pain 5:301-304.
Chung et al. (1996), "Histological Responses of Port Wine Stains in Brown Skin After 578 nm Copper Vapor Laser Treatment", Lasers Surg. Med. 18(4):358-366.
Roden, Dan, MD, "Electrophysiology, Pacing and Arrhythmia", Clin. Cardiol, 20, 285-290 (1997).
Breuer, Miklos M., "Ultrasonic Radiation for Hair Treatments", Cosmetics & Toiletries, vol. 113, pp. 67-75, Jun. 1998.
Webster, D.F., et al., "The Role of Cavitation in the In Vitro Stimulation of Protein Synthesis in Human Fibroblasts by Ultrasound," Ultrasound in Med & Biol., 4, pp. 343-351.
Webster, D. F, et al., "The Role of Ultrasound-Induced Cavitation in the 'In Vitro' Stimulation of Collagen Synthesis in Human Fibroblasts," Ultrasonics, pp. 33-37 (1980).
Castro, D. J., et al. (Dec. 1987), "Biostimulative Effects of Nd:YAG Q-Switch Dye on Normal Human Fibroblast Cultures: Study of a New Chemosensitizing Agent for the Nd: YAG Laser", Laryngoscope, 97(12), pp. 1454-1459.
Database WPI Week 2000046 Derwent Publications Ltd., London, GB; AN 2000-511628; XP002373743 & JP 2000 202044 A (Yamana Co Ltd.) Jul. 25, 2000 *abstract*.
Draper, David, et al. (1995), "Temperature Changes in Deep Muscles of Humans During Ice and Ultrasound Therapies: an in Vivo Study", JOSPT 12(3).
Doan et al, (1999), "In vitro Effects of Therapeutic Ultrasound on Cell Proliferation, Protein Synthesis, and Cytokin Production by Human Fibrosblasts, Osteoblasts, and Monocytes", J. Oral Maxillofac Surg. 57, pp. 409-419.
Edwards, (May 2001) "Keeping Up with the LEDs," Photonics Spectra.
Gann, Nancy, "Ultrasound: Current Concepts", Electrotherapy, vol. 11, No. 4, Jul./Aug. 1991.
Tur, Ethel, et al. (1991), "Percutaneous Penetration of Methy Nicotinate at Three Anatomic Sites: Evidence for an Appendagael Contribution to Transport?", Skin Pharmacol 4, pp. 230-234.
Heuber, F., et al. (1994), "Percutaneous Absorption of Estradiol and Progesterone in Normal and Appendage-Free Skin of the Hairless Rat: Lack of Importance of Nutritional Blood Flow", Skin Pharmacol 7, pp. 245-256.
Freeman et al. (2004), "NGF Deprivation-induced Gene Expression: After Ten Years, Where Do We Stand?," Chapter 8 in Progress in Brain Research 146, Elsevier B.V., 111-126.
Reddy, G. Kesave, et al. (1998), "Laser Photostimulation of Collagen Production in Healing Rabbit Achilles Tendons", Lasers in Surgery and Medicine, 22, pp. 281-287.
Nicolau, G., et al. (1987), "Deposition of Viprostol (a Synthetic PGE2 Vasodilator) in the Skin Following Topical Administration to Laboratory Animals", Xenobiotica 17(9), pp. 1113-1120.
Gao et al. (Jul. 13, 2004), "Induction of Phase 2 Genes by Sulforaphane Protects Retinal Pigment Epithelial Cells Against Photooxidative Damage", PNAS 101(28:10446-10451).
Giamundo (May 2001), "A Little Enlightenment," Photonics Spectra.
Menon, Gopinathan K., et al. (1994), "High-Frequency Sonophoresis: Permeation Pathways and Structural Basis for Enhanced Permeability", Skin Pharmacol. 7, pp. 130-139.
Gupta et al. (1998), "The Use of Low Energy Photon Therapy (LEPT) in Venous Leg Ulcers: A Double-Blind, Placebo-Controlled Study", Dermatol. Surg. 24, pp. 1383-1386.
Gupta, A. K., et al. (1997) "The Use of Low Energy Therapy in the Treatment of Leg Ulcers—A Preliminary Study," Journal of Dermatological Treatment 8(2), pp. 103-108.
Van Weelden, H., et al. (1990), "Comparison of Narrow band UV-B Phototherapy and PUV Photochemotherapy in the Treatment of Psoriasis", Acta Dermatol Venereol (Stockh) 70, pp. 212-215.

Benson, Heather A., et al, (1991), "Influence of Ultrasound on the Percutaneous Absorption of Nicotinate Esters," Pharmaceutical Research 8(2), pp. 204-209.
Benson, Heather A., et al. (1988), "Transmission of Ultrasound Energy Through Topical Pharmaceutical Products", Physiotherapy 74(11), pp. 587-589.
Huang et al. (Aug. 2004), "Downregulation of ATP Synthase Subunit-6, Cytochrome c Oxidase-III, and NADH Dehydrogenase-3 by Bright Clinic Light in the Rat Retina". Investigative Ophthalmology & Visual Science 45 (8):2489-2496.
Chen, Huxiong, et al. (1995), "Chemical Generation of Acoustic Waves: A Giant Photoacoustic Effect", Science 270.
Omura, T., "Hemoprotein H-450 Identified as a Form of Cytocherome P-450 Having an Endorgenous Ligand at the 6th Coordination Position of the Heme (Abstract)", J. Biochem (Tokyo), Nov. 1984; 96(5)1491-1500.
Kao, Jr., et al. (1988), "In Vitro Percutaneous Absorption in Mouse Skin: Influence of Skin Appendages", Toxicology and Applied Pharmacology 94, pp. 93-103.
Pospisilova,J., et al. (1977), "Ultrasonic Effect on Collagen Synthesis and Deposition in Different Localized Experimental Granulomas", Acta Chirurgiae Plasticae 19, pp. 148-156.
M. Suzuki et al. (May 1978), "Autoradiographic Study on Percutaneous Absorption of Several Oils Useful for Cosmetics", J. Soo, Cosmet. Shem., 29, 265-282.
Ferry, James, et al. (1990), "Relationship Between Contact Time of Applied Dose and Percutaneous Absorption of Minoxidil from a Topical Solution". Journal of Pharmaceutical Sciences 79(6), pp. 483-486.
Ortonne, Jean-Paul, "Psoralen Therapy in vitiligo", Clinics in Dermatology, 1989; vol. 7, No. 2, April-June.
Kumar, Saran, et al. (1992), "Studies of In Vitro Skin Permeation and Retention of a Leukotriene Antagonist from Topical Vehicles with a Hairless Guinea Pig Model", Journal of Pharmaceutical Sciences, vol. 81, No. 7.
Tsai, Jui-Chen, et al. (1992), "Drug and Vehicle Deposition from Topical Applications: Use of Vitro Mass Balance Technique with Minoxidil Solutions", Journal of Pharmaceutical Sciences, vol. 81, No. 8.
Mitragotri, Samir, et al. (Jun. 1995), "A Mechanistic Study of Ultrasonically-Enhanced Transdermal Drug Delivery," Journal of Pharmaceutical Sciences, vol. 84, No. 6.
Egbaria, Kamel ,et al. (1992), "Absorption of Fluorescein Dyes on Albumin Microspheres", Pharmaceutical Research 9, pp. 629-635.
Karu et al. (1996), "Effects of Monochromatic Low-intensity Light and Laser Irradiation on Adhesion of the HeLa Cells in Vitro", Lasers Surg. Med. 18(2):171-177.
Tachibana, Katsuro (1992), "Transdermal Delivery of Insulin to Allosxan-Diabetic Rabbits by Ultrasound Exposure", Pharmaceutical Research 9(7).
Newman, J.T., Nellermoe, M.D., & Carnett, J.L. (1992), "Hydrocortisone phonophoresis: A literature review," Journal of the American Podiatric Medical Association, 82(8). pp. 432-435.
Menon, G.K., Bommannan, D.B., & Elias, P.M. (1993). "High-frequency sonophoresis: Permeation pathways and structural basis for enhanced permeability," Skin Pharmacol, 7. pp. 130-139.
Mitragotri, S., Blankschtein, D., & Langer, R. (1995). "Ultrasound-mediated transdermal protein delivery," Science, 269. pp. 850-853.
Draper, D.O., Castel, J.C., & Castel, D. (1995). "Rate of temperature increase in human muscle during 1 MHz and 3 MHz continuous ultrasound," JOSPT, 22(4) pp. 142-150.
Rougier, A., et al. (1983) "In vivo correlation between stratum corneum reservoir fnction and percutaneous absorption," The Journal of Investigative Dermatology, 81. pp. 275-278.
Zabel, K. (1999). "Wrinkle removal without the wound," Dermatology Times, 20(6).
Zabel, K. (1999). "Future of laser surgery: Unexplored benefits await," Dermatology Times, 20(6).
Gniadecka, M., et al. (1994). "Ultrasound structure and digital image analysis of the subepidermal low echogenic band in aged human skin: Diurnal changes and interindividual variability." The Journal for Investigative Dermatology. 102(3). pp. 362-365.

(56) References Cited

OTHER PUBLICATIONS

Mitragotri, S., et al. (1995). "A mechanistic study of ultrasonically-enhanced transdermal drug delivery," Journal of Pharmaceutical Science. 84(6). pp. 697-706.
Meidan, V.M., et al. (1998), "Low intensity ultrasound as a probe to elucidate the relative follicular contribution to total transdermal absorption," Pharmaceutical Research, 15(1). pp. 85-92.
Mitragotri, S., Blankschtein, D., & Langer, R. (1996), "Transdermal drug delivery using low-frequency sonophoresis," Pharmaceutical Research, 13(3). pp. 411-420.
Mitagotri, S. Blankschtein, D., & Langer, R. (1986). "An explanation for the variation of the sonophoretic tansdermal transport enhancement from drug to drug," Journal of Pharmaceutical Science, 86(10). pp. 1190-1192.
Hippius, M., et al. (1998). "In vitro investigations of drug release and penetration—enhancing effect of ultrasound on transmembrane transport of flufenamic acid," International Journal of Clinical Pharmacological, Therapy, and Toxicology, 36(2). pp. 107-111.
Miyazaki, S., et al. (1992). "External control of drug release and penetration. VI. enhancing effect of ultrasound on the transdermal absorption of indomethacin from an ointment in rats," Chemical and Pharmaceutical Bulletin, 40(10). pp. 2826-2830.
Asano, J., et al (1997). "Effect of pulsed output ultrasound on the transdermal absorption of indomethacin fom an ointment in rats," Biological and Pharmaceutical Bulletin, 20(3). pp. 288-291.
Miyazak, S., et al. (1991). "External control of drug release and penetration: Enhancement of the transdermal absorption of indomethacin by ultrasound irradiation," Journal of Pharmaceutical Pharmacology, 43(2). pp. 115-116.
Bommannan, D. et al. (1992). "Sonophoresis.I. the use of high-fequency ultrasound to enhance transdermal drug delivery," Pharmaceutical Research, 9(4). pp. 559-564.
Tachibana, K., Tachibana, S. (1998) "Application of ultrasound energy as a new drug delivery system," Nippon Rinsho, 56(3). pp. 584-588.
Byl, N.N. (1995). "The use of ultrasound as an enhancer for transcutaneous drug delivery: phonophoresis," Physical Therapy, 75(6). pp. 539-553.
Hikima, T., Hirai, Y., & Tojo, K. (1998), "Effect of ultrasound application on skin metabolism of prednisolone 21-acetate," Pharmaceutical Research, 15(11). pp. 1680-1683.
Yata, N. (1998). "Enhancement of drug absorption by iontophoresis and phonophoresis and clinical application," Nippon Rinsho, 56(3). pp. 608-612.
Kimura, I.F., et al. (1998). "Effects of two ultrasound devices and angles of application on the temperature of tissue phantom," Journal of Orthopedic and Sports Physical Therapy, 27(1). pp. 27-31.
Mikulak, S.A., Vangsness, C.T., & Nimmi, M.E. (1998). "Transdermal delivery and accumulation of indomethacin in subcutaneous tissues in rats," Journal of Pharmaceutical Pharmacology, 50(2). pp. 153-158.
Murakami, T., et al. (1998). "Topical delivery of keloid therapeurtic drug, trailast, by combined use of oleic acid and propylene glycol as a penetration enhancer: Evaluation by skin microdialysis in rats," Journal of Pharmaceutical Pharmacology, 50(1). pp. 49-54.
Stott, P.W., Williams, A.C., & Barry, B.W. (1998). "Transdermal delieevery from eutictic systems: Enhanced permeation of a model drug, ibuprofen." Journal of Controlled Release, 50(1-3). pp. 297-308.
Morimoto, Y., & Fujimoto, S. (1985). "Albumin microspheres as drug carriers," Critical Review of Therapeutic Drug Carrier Systems, 2(1). pp. 19-63.
Johnson, M.E. et al. (1996). "Synergistic effects of chemical enhances and therapeutic ultrasound on transdermal drug delivery," Journal of Pharmaceutical Science, 85(7). pp. 670-679.
Illel, B. (1997). "Formulation for transfollicular drug administration: some recent advances," Critical Review of Therapeutic Drug Carrier Systems, 14(3). pp. 207-219.
Mitragotri, S. (2000). "Synergistic effect of enhances for transdermal drug delivey," Pharmaceutcal Research, 17(11). pp. 1354-1359.
Frenkel, V., Kimmel, E., & Iger. Y. (2000). "Ultrasound-facilitated transport of silver chloride (AgCl) particles in fish skin," Journal of Controlled Release, 68(2). pp. 251-161.
Mitragotri, S. (2001). "Effect of therapeutic ultrasound on partition and diffusion coefficients in human stratum corneum," Journal of Controlled Release, 71(1), pp. 23-29.
Tan, H.S., & Pfister, W.R. (1999), "Pressure-sensitve adhesives for transdermal drug delivery systems," PSTT, 2(2). pp. 60-69.
Tajima, S., & Pinnel. S.R. (1996). "Ascorbic acid preferentially enhances type I and III collagen gene transcription in human skin fibroblasts," Journal of Dermatological Science, 11(3), pp. 250-253.
Castro, D.J., et al. (1987). "Biostimulative effects of Nd: YAG Q-switch dye on normal human fibroblast cultures: Study of a new chemosensitizing agent for the Nd:YAG laser," Laryngoscope, 97(12). pp. 1454-1459.
Omura, T., et al. (1984). "Hemoprotein H-450 identified as a form of cytochrome P-450 having an endogenous ligand at the 6th coordination position of the heme," Journal of Biochemistry, 96(5). pp. 1491-1500.
Hrnjak, M., et al. (1995). "Stimulatory effect of low-power density He-Ne laser radiation on human fibroblasts in vitro," Vojnosanit Pregl, 52(6). pp. 539-546.
Krammer, B., Hubmer, A., & Hermann, A. (1993). "Photodynamic effects on the nuclear envelope of human skin fibroblasts," Journal of Photochemistry and Photobiology, 17(2). pp. 109-114.
Lyons, R.F., et al. (1987). "Biostimulation of wound healing in vivo by a helium-neon laser," Annals of Plastic Surgery, 18(1). pp. 47-50.
Yu, W., Naim, J.O., & Lanzafame, R.J. (1997). "Effects of photostimulation on wound healing in diabetic mice," Lasers in Surgery and Medicine, 20(1). pp. 56-63.
Morrone, G., et al. (1998). "In vitro experimental research of rabbit condrocytes biostimulation with diode laser Ga-Al-As: a preliminary study," Artificial Cells, Blood Substitutes, and Biotechnology, 26(4). pp. 437-439.
Van Breugel, H.H., & Bar, P.R. (1992). "Power density and exposure time of He-Ne laser irradiation are more important than total energy dose in photo-biomodulation of human fibroblasts in vitro," Lasers in Surgery and Medicine, 12(5). pp. 528-537.
Response to Office Action dated Jul. 2, 2007 for European Patent Application No. 02792232.7.
Office Action dated Jun. 22, 2009 for European Patent Application No. 02792232.7.
Response to Office Action dated Jun. 22, 2009 for European Patent Application No. 02792232.7.
Office Action dated Oct. 18, 2010 for European Patent Application No. 02792232.7.
Office Action dated Oct. 10, 2012 for European Patent Application No. 02792232.7.
First Examination Report dated Jul. 12, 2007 for Indian Patent Application No. 620/KOLNP/2004.
Official Action dated Feb. 14, 2008 for Israeli Patent Application No. 161865.
Response to Official Action dated Feb. 14, 2008 for Israeli Patent Application No. 161865.
Office Action dated Sep. 15, 2010 for Israeli Patent Application No. 161865.
Response to Office Action dated Sep. 15, 2010 for Israeli Patent Application No. 161865.
Office Action dated May 14, 2008 for Japanese Patent Application No. 2003-541770.
Report of Final Decision of Refusal dated Feb. 24, 2009 for Japanese Patent Application No. 2003-541770.
Office Action dated Sep. 23, 2009 for Korean Patent Application No. 7007060/2004.
Response to Office Action dated Sep. 23, 2009 for Korean Patent Application No. 7007060/2004.
Office Action dated Jul. 27, 2010 for Korean Patent Application No. 7007060/2004.
Response to Office Action dated Jul. 27, 2010 for Korean Patent Application No. 7007060/2004.
Appeal Brief dated Oct. 26, 2010 for Korean Patent Application No. 7007060/2004.

(56) References Cited

OTHER PUBLICATIONS

Office Action dated Dec. 9, 2010 for Korean Patent Application No. 7007060/2004.
Response to Office Action dated Dec. 9, 2010 for Korean Patent Application No. 7007060/2004.
Office Action dated Jan. 17, 2012 for Korean Patent Application No. 70007060/2004.
Official Letter dated May 21, 2008 for Mexican Patent Application No. 2004/004463.
Response to Official Letter dated May 21, 2008 for Mexican Patent Application No. 2004/004463.
Examination Report dated Mar. 13, 2006 for New Zealand Patent Application No. 533303.
Search Report dated May 22, 2008 for PCT Patent Application No. PCT/US07/02958.
Search Report dated May 27, 2008 for PCT Patent Application No. PCT/US07/05288.
Search Report dated Mar. 2, 2008 for PCT Patent Application No. PCT/US07/05288.
Examiner's first report dated Aug. 5, 2010 for Australian Patent Application No. 2007212519.
Response to Office Action dated Feb. 29, 2012 for Japanese Patent Application No. 2008-553383.
Office Action dated Feb. 29, 2012 for Japanese Patent Application No. 2008-553383.
Office Action dated Aug. 26, 2011 for European Patent Application No. 07763561.3.
Voluntary Amendment dated Dec. 4, 2008 for European Patent Application No. 07763561.3.
Search Report and Opinion dated Apr. 23, 2009 for European Patent Application No. 07763561.3.
First Examination Report dated Aug. 19, 2009 for European Patent Application No. 07763561.3.
Response to First Examination Report dated Aug. 19, 2009 for European Patent Application No. 7763561.3.
Response to Office Action dated Mar. 21, 2012 for Japanese Patent Application No. 2008-557382.
Office Action dated Mar. 21, 2012 for Japanese Patent Application No. 2008-557382.
Invitation to Correct Defects dated Jul. 22, 2002 for PCT Patent Application No. PCT/US02/20706.
Response to Invitation to Correct defects dated Jul. 22, 2002 for PCT Patent Application No. PCT/US02/20706.
Written Opinion dated Jul. 31, 2003 for PCT Patent Application No. PCT/US02/20706.
Response to Written Opinion dated Jul. 31, 2003 for PCT Patent Application No. PCT/US02/20706.
Preliminary Examination Report dated Oct. 27, 2005 for PCT Patent Application No. PCT/US02/20706.
International Search Report dated Aug. 11, 2003 for PCT Patent Application No. PCT/US03/10509.
Preliminary Examination Report dated Jun. 17, 2004 for PCT Patent Application No. PCT/US03/10509.
Official Action dated Jul. 28, 2010 for Israeli Patent Application No. 159579.
Response to Official Action dated Jul. 28, 2010 for Israeli Patent Application No. 159579.
Official Action dated Sep. 8, 2008 for Israeli Patent Application No. 159579.
Response to Official Action dated Sep. 8, 2008 for Israeli Patent Application No. 159579.
Voluntary Amendment dated Apr. 19, 2006 for Canadian Patent Application No. 2452408.
Office Action dated Jun. 2, 2006 for Canadian Patent Application No. 2452408.
Yano, K., Lawence, B.F., & Detmar M. (2001). "Control of hair growth and follicle size by VEGF-mediated angiogensis." The Journal of Clinical Investigation, 107(4), pp. 409-417.

Wei, Y.H., et al. (2001) "Mitochondrial theory of aging matures—Roles of mtDNA mutation and oxidative stress in human aging." Chinese Medical Journal, 64, pp. 259-270.
Hoffman, J.W., et al (2004). "Myocardial reperfusion injury: Etiology, mechanisms, and therapies." The Journal of the American Society of Extra-Corporeal Technology, 36, pp. 391-411.
Chwirot, W.B. (1986). "New indications of possible role of DNA in ultraweak photon emission from biological sysems." Journal of Plant Physiology, 122, pp. 81-86.
Albrecht-Buehler G. (1994). "Celluar infrared detector appears to be contained in the centrosome." Cell Motility and the Cytoskeleton 27, pp. 262-271.
Kiang, J.G. (2004). "Inducible heat shock protein 70kD and inducible nitric oxide synthase in hemorrhage/resuscitation-induced injury." Cell Research, 14(6), pp. 450-459.
Yu, W., et al (1997). "Improvement of host response to sepsis by photobiomodulatio." Lasers in Surgery and Medicine, 21(3), pp. 262-268.
Byrnes, K. R., et al. (2004). "Photobiomodulation improves cutaneous wound healing in an animal model of type II diabetes." Photomedicine and Laser Surgery, 22(4), pp. 281-290.
Byrnes, K.R., et al. (2005). "Light promotes regeneration and functional recovery and alters the immune response after spinal cord injury." Lasers in Surgery and Medicine. Feb. 9, (online).
Wong-Riley. M.T., et al. (2005). "Photobiomodulation directly benefits primary neurons functionally inactive by toxins: role of cytochrome c oxidase." Journal of Biological Chemistry, 280(6), pp. 4761-4771.
El Hindi, T., et al. (2004). "Determination of the antioxidant capacity of an antioxidant combination using the fluoroscan assay in vitro and visualization of its effects using histological methods." Archives of Dermatological Research, 296(6) pp. 258-264.
Elmes, C.A., Vargas, A., & Oresajo, C. (1992) "Photoprotective effecs of sunsceens in cosmetics on sunburn and Langerhans cell photodamage." Photodermatology, Photoimmunology, and Photomedicine, 9(3), pp. 113-120.
Stein, R. (2005). "Fat found to accelerate aging process." Washington Post, Jun. 14, 2005.
Block, G., et al. (2004). "Plasma-C reactive protein concentrations in active and passive smokers: influence of antioxidant supplementation." Journal of the American College of Nutrition, 23(2), p. 141-147.
Noda, Y., et al. (2002). "Antioxidant activities of pomegranate fruit extract and its anthocyanindins: delphindin, cyaniding, and pelagronidin." Journal of Agricultural and Food Chemistry, 50(1), pp. 166-171.
Monaco, J.L. & Lawrence, W.T. (2003). "Acute wound healing an overview." Clinics in Plastic Surgery, 30, pp. 1-12.
Hinz, B., et al. (2001). "Apha-smooth muscle actin expression upregulates fibroblast contractile activity." Molecular Biology of the Cell, 12, pp. 2730-2741.
Azevedo, L.H., et al. (2005). "Evaluation of low intensity laser effects on the thyroid gland of male mice." Photomedicine and Laser Surgery. 23(6), pp. 567-570.
Tuby, H., Maltz. L., & Oron, U. (2006). "Modulations of VEGF and iNOS in the rat heart by low level laser therapy are associated with cardioprotection and enhanced angiogensis." Lasers in Surgery and Medicine, 38, pp. 682-688.
Fratelli, M., et al. (2005), "Gene expression in profiling reveals a signaling role of gluthathione in redox regulation." PNAS, 102(39), pp. 13998-14003.
Hymes, S.R., Strom, E.A., & Fife, C. (2006). "Radiation dermatitis: Clinical presentation, pathophysiology, and treatment 2006." Journal for the American Academy of Dermatology, 54, pp. 28-46.
Omura, Y. (2004). "Special sunrise & sunset solar energy stored papers and their clinical applications for intractable pain, circulatory disturbances & cancer: Comparison of Beneficial effects between special solar energy stored paper and quigong energy stored paper." Acupunture & Electro-therapeutics, 29, pp. 1-42.
Stoica, E. & Enulescu, O. (1988). "Catecholamine response to light in migrainee" Cephalalgia, 8, pp. 31-36.

(56) References Cited

OTHER PUBLICATIONS

Kowluru, R.A. (2005). "Diabetic retinopathy: mitochondrial dysfunction and retinal capillary cell death." Antioxidants & Redox Signaling, 7(11,12), pp. 1581-1587.
McDaniel, D., et al. (1998), "Body contouring: A preliminary report on the use of the silhouette® device for treating cellulite." Aesthetic Surgery Journal, 18(3), pp. 177-182.
Noton, D. (2000). "Migraine and photic stimulation: Report on a survey of migraineurs using flickering light therapy." Complementary Therapies in Nursing & Midwifery, 6, pp. 138-142.
Alstadhaug, K.B., Salvesen, R., & Bekkelund, S.I. (2005). "Seasonal variation in migraine." Cephalalgiai, 25, pp. 811-816.
Claustrat, B., et al. (2004). "Melatonin secretion is supersensitive to light in migraine." Cephalalgia, 24, pp. 128-133.
Passache, G., et al. (2000). "Mitochondria of retinal muller (glial) cells: The effects of aging and of application of free radical scavengers." Opthalmic Research, 32, pp. 229-236.
Liang, F.Q. & Godley, B.F. (2003). "Oxidative stress-induced mitochondrial DNA damage in human retinal pigment epithelial cells: A possible mechanism for RPE aging and age-related macular degeneration," Experimental Eye Research, 76, pp. 397-403.
Anderson, D.J., et al. (1997) "Preliminary trial of photic mulation for premenstrual syndrome." Journal of Obstetrics and Gynaecology, 17(1), pp. 76-79.
Main, A., et al. (2000). "The wavelength of light causing photophobia in migraine and tension-type headache between attacks." Headache, 40, pp. 194-199.
Eells, J.T., et al. (2004). "Mitochondrial signal transduction in accelerated wound and retinal healing by near-infrared light therapy," Mitochondrion, 4, pp. 559-567.
"Thiol" From Wikipedia page: http://en.wikipedia.org/wiki/Thiol Accessed: May 6, 2007.
"Disulfide Bond" From Wikipedia page: http://en.wikipedia.org/wiki/Disulfide_bond Accessed: May 6, 2007.
"Permanent Wave" From Wikipedia page: http://en.wikipedia.org/wiki/Permanent_wave Accessed: May 6, 2007.
Martin, K. (2007). "Infrared and ramen studies of skin and hair: A review of cosmetic spectroscopy." The Internet Journal of Vibrational Spectroscopy, 3(2), online Accessed: Apr. 24, 2007.
Final Office Action dated Dec. 9, 2011 for U.S. Appl. No. 12/753,207.
Response to Final Office Action dated Dec. 9, 2011 for U.S. Appl. No. 12/753,207.
Notice of Restriction dated Mar. 29, 2006 for U.S. Appl. No. 10/665,390.
Response to Restriction dated Mar. 29, 2006 for U.S. Appl. No. 10/665,390.
Non Final Rejection dated Aug. 21, 2006 for U.S. Appl. No. 10/665,390.
Non Final Rejection dated Jan. 5, 2006 for U.S. Appl. No. 10/903,483.
Amendment to Non-Final Rejection dated Jan. 5, 2006 for U.S. Appl. No. 10/903,483.
Non Final Rejection dated Sep. 25, 2006 for U.S. Appl. No. 10/903,483.
Amendment to Non-Final Rejection dated Sep. 25, 2006 for U.S. Appl. No. 10/903,483.
Non Final Rejection dated May 22, 2008 for U.S. Appl. No. 10/903,483.
Non Final Rejection dated Jul. 18, 2007 for U.S. Appl. No. 11/205,316.
Amendment to Non-Final Rejection dated Jul. 18, 2007 for U.S. Appl. No. 11/205,316.
Final Rejection dated Jun. 9, 2008 for U.S. Appl. No. 11/205,316.
Non Final Rejection dated Oct. 19, 2007 for U.S. Appl. No. 11/272,042.
Amendment to Non-Final Rejection dated Oct. 19, 2007 for U.S. Appl. No. 11/272,042.
Final Rejection dated Jun. 6, 2008 for U.S. Appl. No. 11/272,042.
Non-Final Rejection dated Jun. 8, 2010 for U.S. Appl. No. 12/583,562.
Amendment to Non-Final Rejection dated Jun. 8, 2010 for U.S. Appl. No. 12/583,562.
Official Notification dated Dec. 3, 2008 for Israeli Patent Application No. 171311.
Official Notification dated Nov. 19, 2009 for Israeli Patent Application No. 171311.
Response to Official Notification dated Nov. 19, 2009 for Israeli Patent Application No. 171311.
First Office Action dated Mar. 10, 2006 for Chinese Patent Application No. 200480012575.X.
Response to First Office Action dated Mar. 10, 2006 for Chinese Patent Application No. 200480012575A.
Second Office Action dated Nov. 2, 2007 for Chinese Patent Application No. 200480012575.X.
Notice of Reexamination dated Jul. 27, 2010 for Chinese Patent Application 200480012575.X.
Response to Notice of Reexamination dated Jul. 27, 2010 for Chinese Patent Application No. 200480012575.X.
Official Notification regarding clarification of claims dated Sep. 19, 2002 for PCT Patent Application No. PCT/US02/26627.
Request for Rectification of Obvious Errors in the International Patent Application and Submission of Request to Record Change of Agent's Address dated Sep. 27, 2002 for PCT Patent Application No. PCT/US02/26627.
International Search Report dated May 16, 2003 for PCT Patent Application No. PCT/US02/26627.
Written Opinion dated Feb. 5, 2004 for PCT Patent Application No. PCT/US02/26627.
International Search Report dated May 8, 2003 for PCT Patent Application No. PCT/US02/35839.
International Preliminary Examination Report dated Oct. 7, 2003 for PCT Patent Application No. PCT/US02/35839.
First Statement of Proposed Amendments dated Oct. 27, 2005 for Australian Patent Application No. 2002326716.
Examiner's Report dated Mar. 22, 2007 for Australian Patent Application No. 2002326716.
Office Action dated Aug. 2, 2006 for Canadian Patent Application No. 2457590.
Response to Office Action dated Aug. 2, 2006 for Canadian Patent Application No. 2457590.
Office Action dated Apr. 30, 2007 for Canadian Patent Application No. 2457590.
Response and Amendment to Office Action dated Apr. 30, 2007 for Canadian Patent Application No. 2457590.
Office Action dated Jan. 31, 2008 for Canadian Patent Application No. 2457590.
Request for Reinstatement for Failure to Respond to Office Action dated Jan. 31, 2008 for Canadian Patent Application No. 2457590.
Office Action dated Oct. 2, 2009 for Canadian Patent Application No. 2457590.
Response to Office Action dated Oct. 2, 2009 for Canadian Patent Application No. 2457590.
Office Action dated Dec. 30, 2010 in Canadian Patent Application No. 2,457,590.
Office Action dated May 6, 2010 in Canadian Patent Application No. 2,457,590.
Response to Office Action dated May 6, 2010 in Canadian Patent Application 2,457,590.
Office Action dated Aug. 25, 2006 for European Patent Application No. 02761449.4-1216.
Response to Office Action dated Aug. 25, 2006 for European Patent Application No. 02761449.4-1216.
Office Action dated Jul. 31, 2007 for European Patent Application No. 02761449.4-1216.
Response to Office Action dated Jul. 31, 2007 for European Patent Application No. 02761449.4-1216.
Result of Consultation by Telephone with Applicant/Representative dated Aug. 28, 2008 for European Patent Application No. 02761449.4-1216.
Decision to Refuse a European Application dated Mar. 31, 2009 for European Patent Application No. 02761449.4-1216.

(56) References Cited

OTHER PUBLICATIONS

Official Action dated May 13, 2008 for Israeli Patent Application No. 160505.
Response to Official Action dated May 13, 2008 for Israeli Patent Application No. 160505.
Office Action dated May 16, 2010 for Israeli Patent Application No. 160505.
Response to Office Action dated May 16, 2010 for Israeli Patent Application No. 160505.
Office Action dated Mar. 1, 2007 for Indian Patent Application No. 00332/KOLNP/2004.
Response to Office Action dated Mar. 1, 2007 for Indian Patent Application No. 00332/KOLNP/2004.
Office Action dated Nov. 10, 2008 for Korean Patent Application No. 7002677/2004.
Decision of Rejection dated Dec. 1, 2008 for Japanese Patent Application No. 2003-522355.
Office Action dated Feb. 22, 2012 for Japanese Patent Application No. 2009-236857.
Response to Office Action dated Feb. 22, 2012 for Japanese Patent Application No. 2009-236857.
Office Action dated Sep. 12, 2012 for Japanese Patent Application No. 2009-236857.
Response to Office Action dated Sep. 12, 2012 for Japanese Patent Application No. 2009-236857.
Official Letter dated Sep. 3, 2007 for Mexican Patent Application No. 2004/001710.
Reply to Official Action dated Sep. 3, 2007 for Mexican Patent Application No. 2004/001710.
2nd Official Action dated Sep. 19, 2008 for Mexican Patent Application No. 2004/001710.
3rd Official Action dated Dec. 8, 2010 for Mexican Patent Application No. 2004/001710.
Response to 3rd Official Action dated Dec. 8, 2010 for Mexican Patent Application No. 2004/001710.
Examination Report dated Apr. 28, 2005 for New Zealand Patent Application No. 531491.
First Statement of Proposed Amendments dated Dec. 21, 2005 for Australian Patent Application No. 2002357695.
Official Report dated Jun. 28, 2007 for Australian Patent Application No. 2002357695.
Response to Official Report dated Jun. 28, 2007 for Australian Patent Application No. 2002357695.
Official Report dated Dec. 19, 2007 for Australian Patent Application No. 2002357695.
Office Action dated Aug. 9, 2006 for Canadian Patent Application No. 2465906.
Response to Office Action dated Aug. 9, 2006 for Canadian Patent Application No. 2465906.
Office Action dated Mar. 27, 2007 for Canadian Patent Application No. 2465906.
Response and Amendment to Office Action dated Mar. 27, 2007 for Canadian Patent Application No. 2465906.
Office Action dated Nov. 23, 2007 for Canadian Patent Application No. 2465906.
Response to Office Action dated Nov. 23, 2007 for Canadian Patent Application 2465906.
Office Action dated Oct. 5, 2010 for Canadian Patent Application No. 2465906.
Response to Office Action dated Oct. 5, 2010 for Canadian Patent Application No. 2465906.
Office Action dated Jun. 30, 2011 for Canadian Patent Application No. 2465906.
Response to Office Action dated Jun. 30, 2011 for Canadian Patent Application No. 2465906.
Office Action dated Mar. 3, 2010 Canadian Patent Application 2465906.
Response to Office Action dated Mar. 3, 2010 for Canadian Patent Application No. 2465906.
Office Action dated Oct. 14, 2005 for Chinese Patent Application No. 028247698.
Response to Office Action dated Oct. 14, 2005 for Chinese Patent Application No. 028247698.
Second Office Action dated Apr. 11, 2008 for Chinese Patent Application No. 028247698.
Response to Second Office Action dated Apr. 11, 2008 for Chinese Patent Application No. 028247698.
Third Office Action dated Aug. 15, 2008 for Chinese Patent Application No. 028247698.
Office Action dated Sep. 11, 2006 for European Patent Application No. 02792232.7.
Response to Office Action dated Sep. 11, 2006 for European Patent Application No. 02792232.7.
Office Action dated Jul. 2, 2007 for European Patent Application No. 02792232.7.

\* cited by examiner

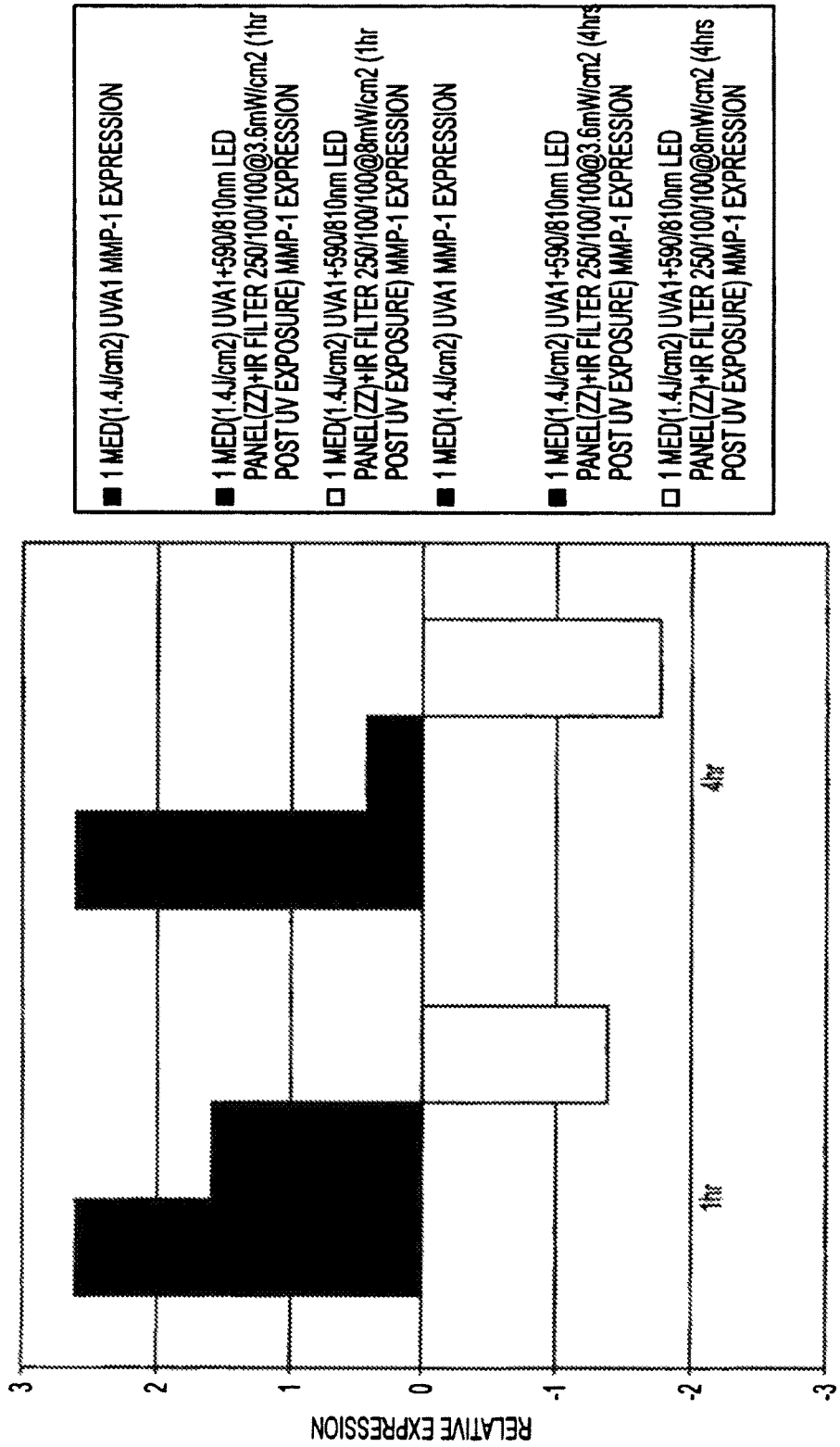

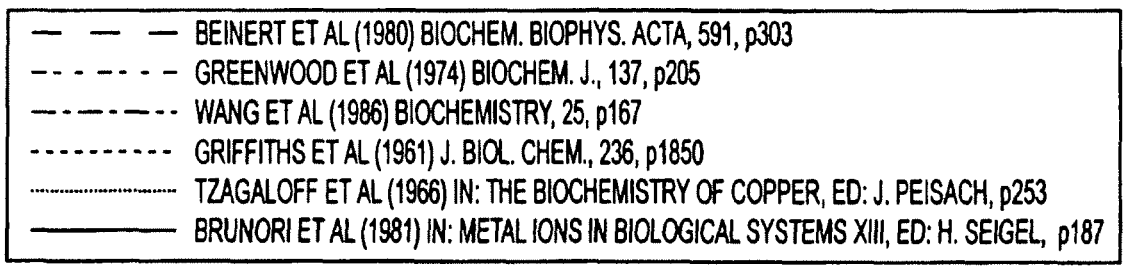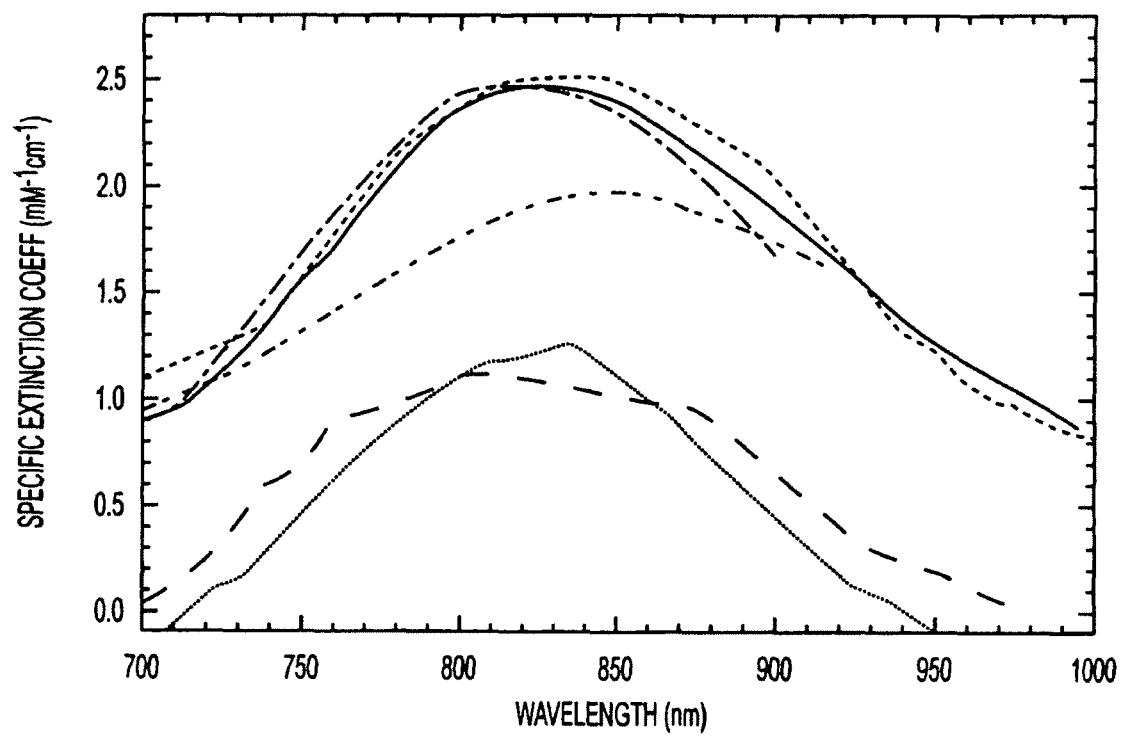
FIG. 26

SYSTEM AND METHOD FOR THE PHOTODYNAMIC TREATMENT OF BURNS, WOUNDS, AND RELATED SKIN DISORDERS

CROSS REFERENCE TO RELATED APPLICATIONS

This application is a continuation of U.S. application Ser. No. 10/903,483, filed Aug. 2, 2004, which is a non-provisional application of U.S. Provisional Application No. 60/491,277, filed Jul. 31, 2003, both of which are hereby incorporated by reference in their entirety.

BACKGROUND OF THE INVENTION

1. Field of the Invention

This invention relates to method and devices for the photodynamic regulation of cell proliferation and gene expression. In particular, the invention relates to the reducing, reversing, and/or diminishing the effects of sunburn, thermal burns, chemical burns, radiation burns, various types of wounds, such as traumatic, surgical, laser, chemical peel, cosmetic surgery, warfare agents or injuries, freezing, hypoxia, vascular insufficiency, bruising, chronic ulcers, etc., allergic reactions or contact dermatitis, and various inflammatory diseases.

2. Description of the Background

Chronological aging, "photo-aging", i.e., the aging of skin caused by exposure to natural and synthetic light sources, disease, and trauma all bring about changes in the appearance of human and mammalian skin as well as changes in the structure and function of the skin. All living cells, tissues and organs also undergo changes associated with chronological aging, bruising, photo-aging, disease, and trauma. Since the human skin is an organ that is highly visible, the changes associated with these conditions are readily apparent and visible. These changes are reflections of the underlying structural and functional changes.

The most widely appreciated form of skin aging is that which is produced by over exposure and repeated chronic exposure to sunlight and is generally termed photoaging. More specifically certain portions of the ultraviolet A (UVA) and ultraviolet B (UVB) and have been determined to be the principal causative factors of what are associated with photoaging.

For many years it was thought that photoaging occurred through a different mechanism of action or and was somehow different than chronological aging. However, more recently it appears that photoaging and chronological aging may share similar, if not identical pathways.

Solar radiation is composed of ultraviolet (LTV), visible and infrared, light. Current conventions divide IJV radiation into UVA (320-400 nm), UUB (290-320 nm) and UVC (<290 nm). UVC radiation is blocked by ozone in the stratosphere and does not reach the earth's surface, but can be generated by germicidal lamps and other machinery. UVA and UVB sunlight do reach the earth and are believed to be the principal agents of photoaging. UVA radiation is further subdivided into UVA 1 and UVA 2. While UVB has been believed to be the primary agent for photoaging, it is now appreciated that certain wavelength ranges within the UVA rays also contribute to changes associated with photoaging.

Acute environmental injuries include sunburn from UV light and other thermal, chemical, and other types of burns or burn-like injuries. These type of injuries produce not only damaged cells, but dying cells. Damaged cells may either repair the damage and return to normal, repair the damage imperfectly and produce an abnormal or sub-optimally functioning cell, or the cells may die. In the case of sunburn chronic sun-damage accumulates damaged and imperfectly repaired cells to produce what might be termed 'solar scars' but we more commonly think of these as 'wrinkles'. That is a wrinkle is really the result of accumulation of imperfectly repaired cell damage. Likewise the brown 'liver' or 'age spots' that are common as one ages and photoages are similarly damage to the pigment cells or melanocytes.

Acute UV injury or sunburn produces dying cells in the upper skin layer or epidermis called 'sunburn cells'. Counting sunburn cells is a classic scientific method to quantify the severity of damage to these keratinocyte cells. Therapies which reduce the number of sunburn cells are considered beneficial to diminishing the severity of the injury or repairing or reversing the injury. More generally speaking damaged cells which might recover or die are termed 'apoptotic' cells and those cells which are irreversibly damaged and will die are termed 'necrotic' cells. Treatments which can turn necrotic cells into living cells would be considered treatments which 'rescue' or 'revive' the cells which are destined for death. Such treatments and therapies would have great importance in treating not only acute sunburn, but sub-acute sun damage that leads to accumulated chronic damage. The ability to 'rescue' dying cells in wounds, burns, etc would have a powerful impact on healing time, scarring or lack thereof, infection risk, and even survival of entire organs or organisms. The pertinent arts have, heretofore, been unable to produce a system or method for reviving or rescuing necrotic cells or those in advanced stages of necrosis.

UVA and UVB light exposure to human skin triggers a series of molecular events including the induction of reactive oxygen species (ROS) in the skin. Through a series of cell signaling events collagen production is down regulated and various enzymes known to degrade structural proteins in the skin up-regulated. The net result of this is a decrease in collagen and the production of wound. The skin's reaction to UVA or UVB (or combined) wounding is to repair the wound through the skins wound healing mechanism. Typically these wound repair mechanisms are imperfect which is considered by many to be a solar scar. After many years of the UVA or UVB wounding of the skin, chronic solar scarring develops which manifests itself in the visible phenotypic changes termed photoaging, which might also be considered the visible outward evidence of solar scars.

Photoaging of the skin may occur through acute injury at higher levels, such as what one associates with sunburn. This triggers an inflammatory process in the skin and the associated cellular mechanisms. There is also a more chronic low-level type of injury that does not produce a sunburn reaction, but which produces the changes of chronic photoaging. Other processes, which are known to decrease collagen production and increase collagen-dissolving enzymes, such as tobacco smoking, also are associated with changes that visibly appear, similar to the photoaging from UVA/UVB light. This can be seen strikingly in photographs of identical twins wherein only one twin smoked tobacco for many years.

UVB radiation in sufficient doses produces reddening or sun burning of the skin. The threshold level is typically described as minimal erythema' dose (MED), typically produced by 290-300 nm UVB wavelengths. As the wavelengths increase they become much less likely to produce the redness and burning reactions and indeed wavelengths of 320 nm are about 100 times as powerful as wavelengths of 340 nm approximately 100 times less powerful than the 290-300 nm range of producing erythema and sunburns. The total UVB exposure is more related to the appearance of photoaging and sunburns are more likely to trigger malignant changes in the skin such as malignant melanoma. In contrast, UVA radiation can produce redness, but also produced tanning and these are the wavelengths typically used for the so-called tanning beds. UVA radiation is a longer wavelength and is proportionately greater in the early morning and late afternoon and the UUB rays, which are typically most predominant and intense at the midday summer sun time exposure period, UVA radiation may also penetrate certain sun blocks mid certain sunscreens and also window glass on automobiles, thus accounting for the frequently observed greater wrinkling, brown pigmentation and redness and overall aged appearance on the left side of the face than the right in patients who occupationally or recreationally spend considerable time driving a left hand drive motor vehicle.

In sunny countries with fair complexioned populations, such as Australia, where right hand drive motor vehicles are used, these changes are seen typically seen on the right side of the face. The patterns of photoaging are determined by which areas of the body are anatomically are more chronically exposed to sunlight. Thus, the face, neck, back of hands, upper chest, lower arms, lower legs and depending on hair styling and density, ears and balding areas manifest the greatest photoaging changes.

The chronological changes and photoaging changes typically are manifest by fine lines and wrinkling of the skin. A coarser, crepey texture to the skin, skin laxity and skin sagging, uneven pigmentation, brown splotchy pigment, loss of skin tone, texture and radiancy, bruising and sallowness. The skin is composed of several layers, the outermost layer is called the stratamocornium (SC), next layer is the epidermis (EPI), and underneath the epidermis lies the dermis (DER). The outer SC serves primarily a barrier function to protect the skin from environmental exposure and also to help minimize water loss from the skin. The epidermis serves many important and diverse roles as does the dermis. The dermis contains the principal structural proteins of the skin. These proteins are collagen, elastin and ground substance. They are manufactured by the fibroblast cells within the dermis. Fibroblast cells control the activity to produce these proteins as regulated by a complex and relatively well defined series of cell receptors and cell signaling mechanisms.

The proliferation of these cells is also an important activity. For example, the dermis also contains blood vessels, nerve fibers, oil and sweat glands, hair follicles and many other important components. There is a remarkably complex inner communication through cell signaling in the cells of the skin. Fibroblasts produced what are termed pro-collagen fibers, which are then insymmetrically assembled into collagen fibers, and form bundles within the dermis. Other molecules, such as decorin affect the function of the collagen. There are various sub-types of collagen fibers such as Collagen I, Ill, etc., within the body. Collagen I comprises approximately 85% of the skin and Collagen III approximately 10%. However, in photoaged skin the amount of Collagen I decreases so the ratio of Collagen III/I is altered.

There are also a variety of enzymes termed matrix metalloproteinases (MMP) which play important roles in aging skin. Fibroblasts also have important functions in wound healing with the removal of damaged structural ECM and the repair and production of (ECM). The Collagen I is degraded principally by MMP 1 (collagenase). There are a variety of MMP enzymes, which degrade one or more of the structural proteins in the skin. While these degrading MMP enzymes serve an important role in removing damaged skin (for example, in wound healing), their activation and synthesis in increased quantities in normal skin helps contribute to the changes seen in both chronological and photoaging. Likewise, if the production of Collagen I is decreased or diminished this results in changes which are associated with chronologically or photoaged skin. Aging or senescent fibroblasts may exhibit decreased synthesis of Collagen I and increased synthesis of MMP 1. Similar changes are seen with UVA/UVB exposure. Other environmental agents may produce similar changes.

Certain drugs, therapies, chemicals, active agents have been demonstrated to reversing the appearance of or phenotype of a chronologically aging or photoaging skin. Some topically applied agents serve as a physical or optical barrier either by reflection or absorption of ultraviolet light thus protecting the skin. There are also enzymes that have been to shown actually repair the DNA dimers which are produced from UV damage. Other topically applied or oral or systemically agents have been shown to improve the appearance of the skin. One of the classic and well-known agents is a topical Vitamin A derivatives termed Retinoids. Numerous studies have demonstrated the ability to improve the appearance or phenotype of photoaged skin with the use of all-trans retinoic acid (RA). Many of the pathways involve the mechanism of action of RA and also Retinol (RO), Much of the mechanism of action in the cell signaling pathways through which RA appears to produce anti-aging effects.

One of the goals of some current anti-aging therapies is to increase production of collagen in the ECM and the dermis of the skin. Some believe collagen I is the more desirable form of collagen to increase. There is some support for this since photoaged skin has less desirable visco elastic properties and this is thought in part to be due to the increased proportion of collagen Ill to collagen I. Other anti-aging approaches indicate that reducing the activity or production of the degrading enzymes in the ECM will similarly produce an anti-aging effect in the appearance of the skin. Doing a combination of both is even more beneficial. An analogy one might make is the production of new collagen I and that of freshly newly fallen snow. The amount of accumulation of the fresh snowfall is dependent both on the amount of snow that is fallen as well as the amount of the freshly fallen snow which then melts. Thus one could envision an anti-aging therapy which stimulated new collagen production (newly fallen snow). When a piece of black asphalt in a parking lot abuts a piece of warmer black asphalt adjoins a colder piece of concrete or frozen ground, while the amount of new snowfall is equal in both areas, the amount of accumulated snow is less was melted by the asphalt. If an anti-aging therapy stimulates collagen I production, but does not diminish MMP 1 activity, the net increase in collagen I will be smaller than if the MMP 1 activity is also decreased.

Historically there have been many approaches to restoring a youthful appearance to human skin for achieving anti-aging or age reversal therapies. Most methods utilize some form of triggering the body's own wound healing mechanism. The more destructive and traumatic methods use chemicals to peel off the stratum cornium epidermis and often a portion of the dermis or they mechanically abraded by sand papering or dermabrating or more recently high-energy thermal lasers have been used to vaporize or coagulate the skin. These methods have a prolonged and painful wounding period and require wound care and patients typically must limit their daily social and business activities during the wound-healing phase. Subsequently the skin undergoes months or years an on going wound healing and wound remodeling process whereby damage is repaired and new structural proteins in skin are generated. These treatments typically amount to trying to produce a controlled entry to the skin and proving the wound care environment that minimizes the risk of scarring. These methods are notoriously known for producing many problems and sometimes even disfiguring scarring or catastrophic pigment changes in the skin. However, properly performed and with good wound care, many people achieved significant and sometimes dramatic anti-aging effects. Other gentler methods have become more popular in recent years which involve the classic plastic surgery lifting procedures and newer procedures termed non-ablative where the outer stratum eornium and epidermis are not removed or blated from the skin, but are by various means and methods protected and left in tact. Non-ablative methods have typically been thermal in nature and through various means of laser light, intense pulsed light, radio frequency or microwave energy delivery then produced a thermal injury to the dermis. The theory behind these therapies is that this injury will result in a net increase in the desirable structural proteins, while not triggering, worsening, scarring or other complications. Results are occasionally traumatic but have been extremely variable with this therapy. The variability in individuals wound healing repair mechanism and the overall health of their body and skin and many other factors contribute to this variability.

There are various topical agents that have been developed for anti-aging purposes such as Retinoic acid, topical Vitamin C, topical Vitamin B and other antioxidant and other anti-wrinkle creams and lotions. Many of these are well defined. Additional topical compositions, cosmeceuticals, etc. are disclosed in applicant's copending application U.S. Ser. No. 09/899,894, entitled "Method and Apparatus for the Photomodulation of Living Cells", filed Jun. 29, 2001, which is hereby incorporated by reference in its entirety. Further, methods for enhancing the penetration of such composition into the skin using ultrasound radiation are described in U.S. Pat. No. 6,030,374, and U.S. Pat. No. 6,398,753, each of which is hereby incorporated by reference in its entirety. Use of such compositions for wound treatment, acne reduction, and other dermatological conditions is described in applicant's copending application Ser. No. 09/933,870, filed Aug. 22, 2001, which is also incorporated by reference herein in its entirety. Additional discussion of the related art is described in applications copending application Ser. No. 10/119,772, filed Apr. 11, 2002, and 60/461,512, filed Apr. 10, 2003, which are also incorporated by reference herein in their entirety.

There is a need to improve the appearance of chronologically aged, photoaged, or environmentally damaged skin, as well as skin that has been damaged by disease or trauma, but without producing the risk, complications, recovery time, pain, discomfort, wound care or other side effects traditionally associated with surgical, chemical, electromagnetic radiation and other types of therapies.

SUMMARY OF THE INVENTION

As embodied and broadly described herein, the present invention is directed to method and devices for improving the appearance of photoaged or damaged skin. Methods and devices involve the regulation of cell proliferation and gene expression of skin and other cells through photodynamic means such as photomodulation.

One embodiment of the invention relates to reducing the undesirable effects and enhancing the beneficial effects of narrowband and wideband multichromatic electromagnetic radiation, as well as monochromatic radiation, emitted by sources including, but not limited to lasers (monochromatic and filtered, narrowband multichromatic), LED's (narrowband multichromatic), radio frequency, electromagnetic therapy or non ablative thermally mediated surgical procedures, etc. For example, LED photomodulation and other similar non-LED therapies may be used to enhance the desired effects or inhibit the undesirable one. This may be accomplished via means such as thermal injury to the skin which forces the expression of MMP and causing an increase structural proteins like collagen. LED light sources may also boost collagen while decreasing the upregulated MMP to produce a beneficial net effect. Such means generally quench the inflammatory processes that thermal therapies typically produce.

One embodiment of the invention is directed to methods for both inhibiting, as well as reversing the appearance of photoaging (beauty maintenance or skin fitness) or chronological or environmentally damaged induced aging of human skin by application of photomodulation by, for example LED or other electromagnetic radiation treatment. Preferably, the invention is directed to the regulation of cell proliferation of cells of the skin, and/or the regulation of gene expression in such cells.

Another embodiment of the invention is directed to the various genotypes that characterize different phenotypes of aging skin and also a database comprising a collection or library of such phenotypes. The data base may comprise a plurality of genotypes identified from a variety of different individuals with the same disorder, or a variety of individuals with different disorders.

Another embodiment of the invention is directed to photomodulation by light or electromagnetic radiation so as to effect cell proliferation and/or gene expression. Examples of different types of electromagnetic radiation include ultrasound, radiowaves, micro rays, magnetic fields, any electrical stimulation that produces changes in the genotype or phenotype of aging skin, and combinations thereof.

Other embodiments and advantages of the invention are set forth in part in the description, which follows, and in part, may be obvious from this description, or may be learned from the practice of the invention.

BRIEF DESCRIPTION OF THE DRAWING FIGURES

FIG. 24 is a chart which illustrates the RT-PCR expression of MMP-1 in cultured human fibroblasts after exposure to electromagnetic radiation simulator solar radiation.

FIG. 25(*b*) illustrates specific extinction coefficients of the cytochromes of FIG. 25(*a*) from 700 nm to 1000 nm.

FIG. 26 illustrates specific extinction coefficients vs. wavelength.

DETAILED DESCRIPTION OF THE INVENTION

Figure 1:
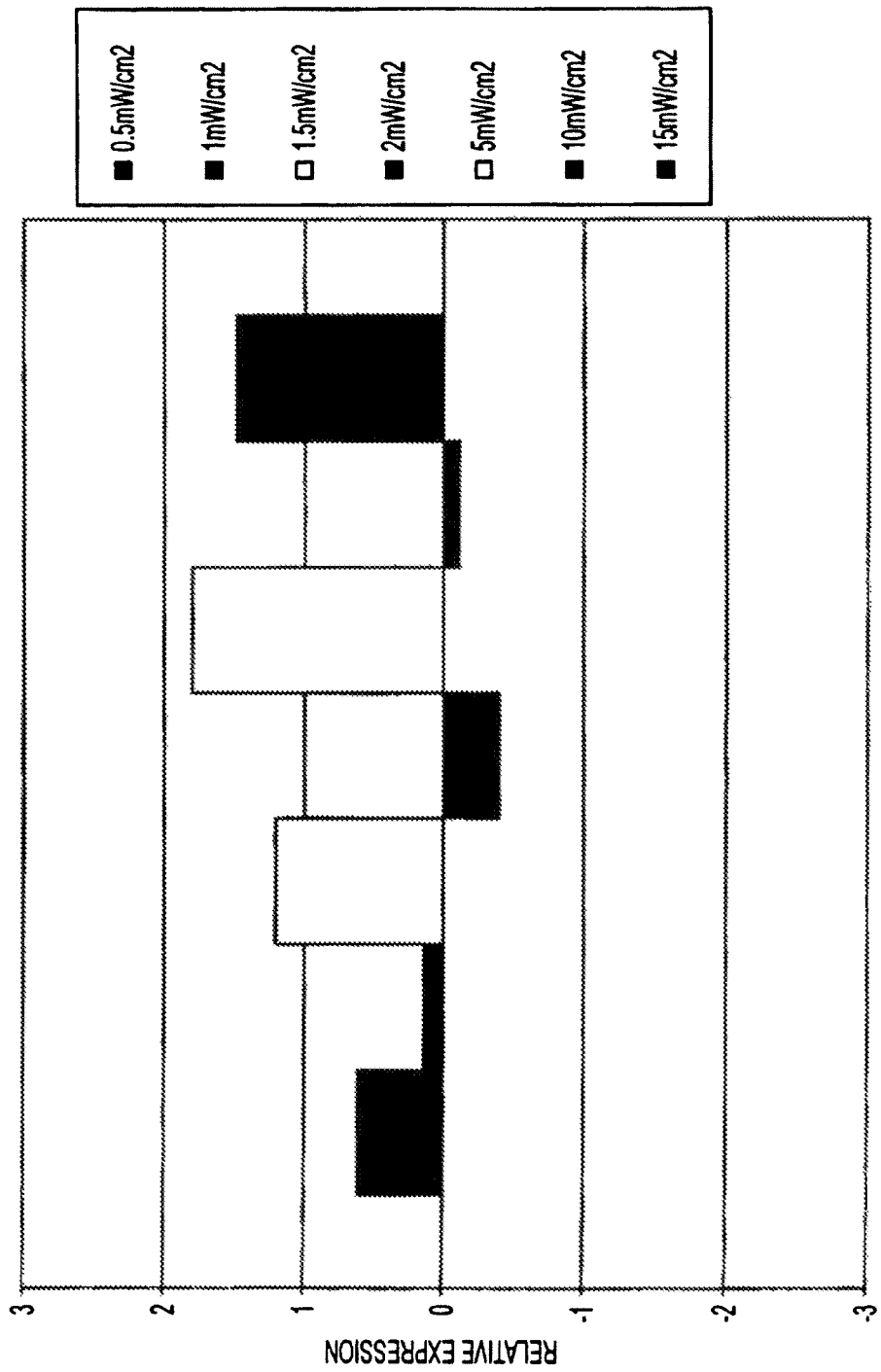
FIG. 1 is a chart which illustrates the RT-PCR expression of MMP-1 in cultured human fibroblasts.
Figure 2:
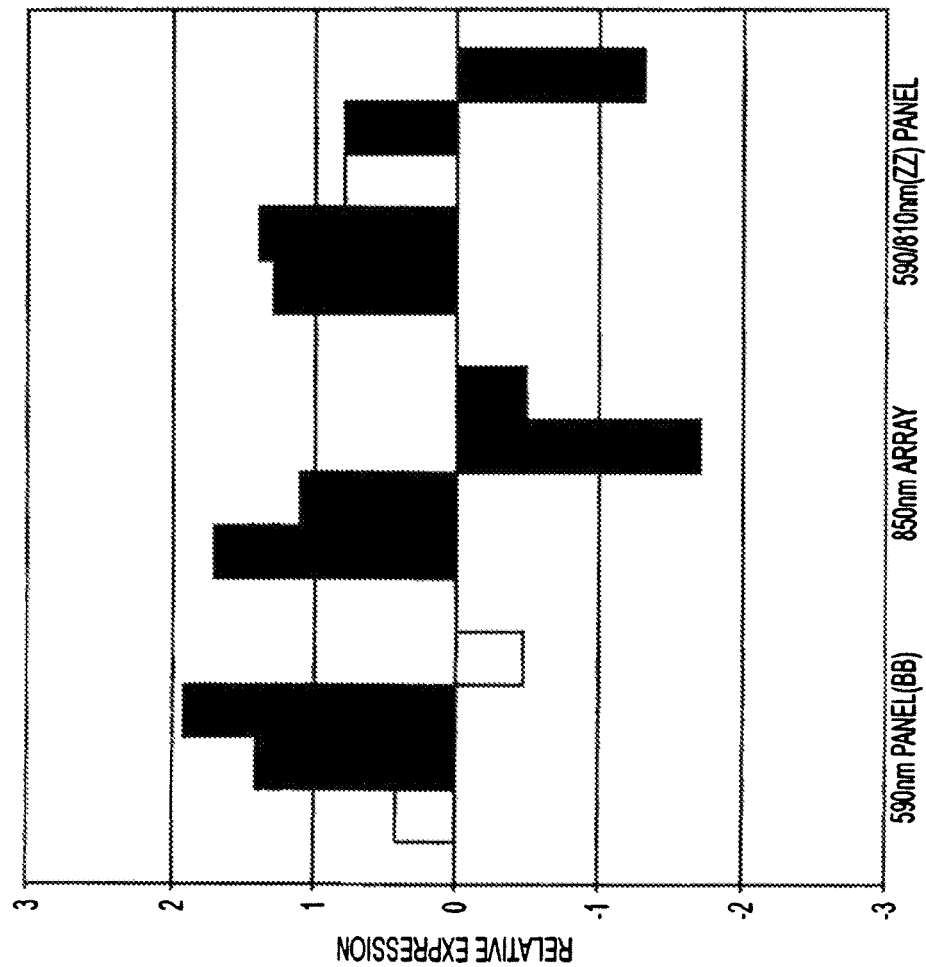
FIG. 2 is a chart which illustrates the RT-PCR expression of MMP-1 in cultured human fibroblasts under a variety of light exposure conditions.
Figure 3:
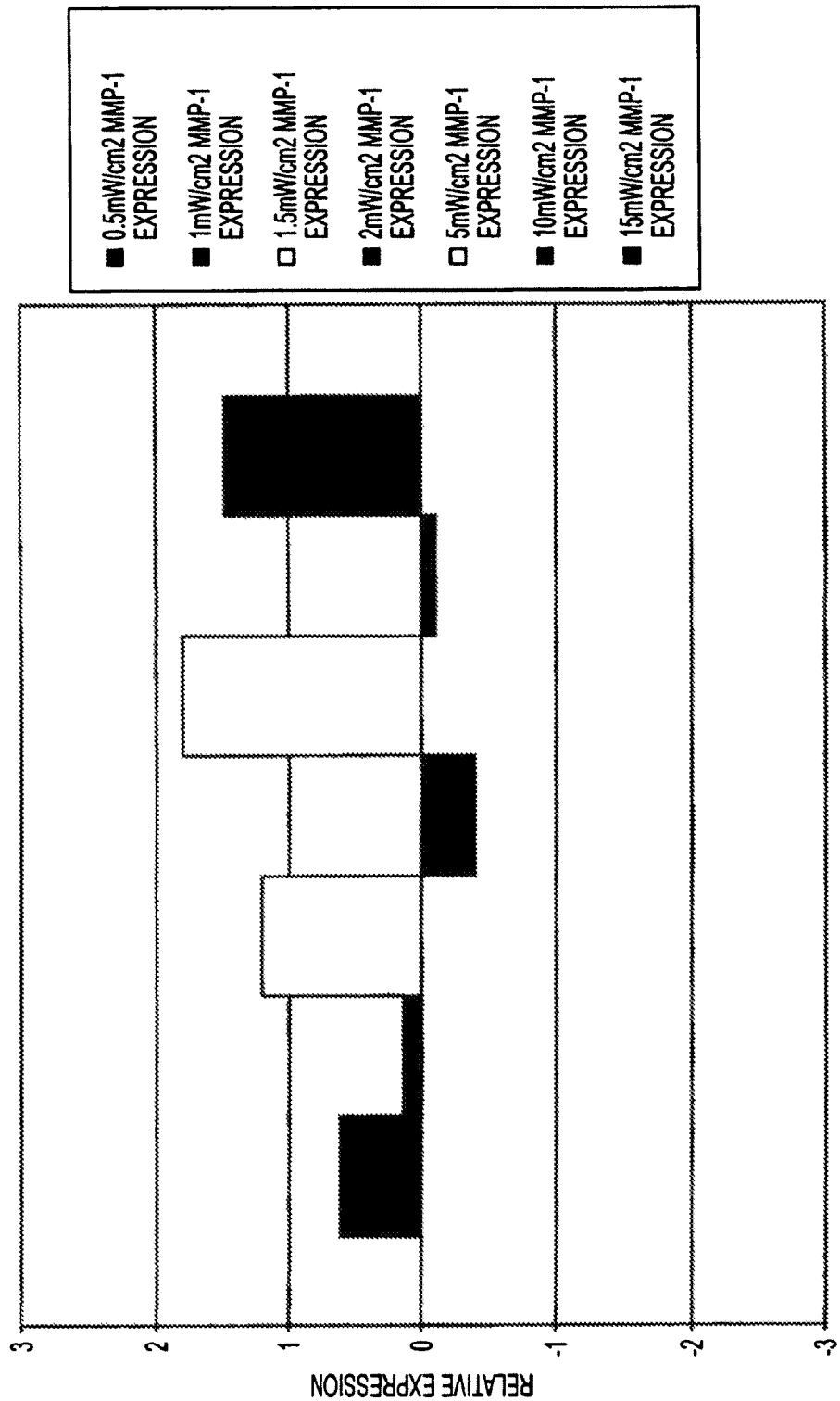
FIG. 3 is a chart which illustrates the RT-PCR expression of MMP-I in cultured human fibroblasts at varying energy fluences.
Figure 4:
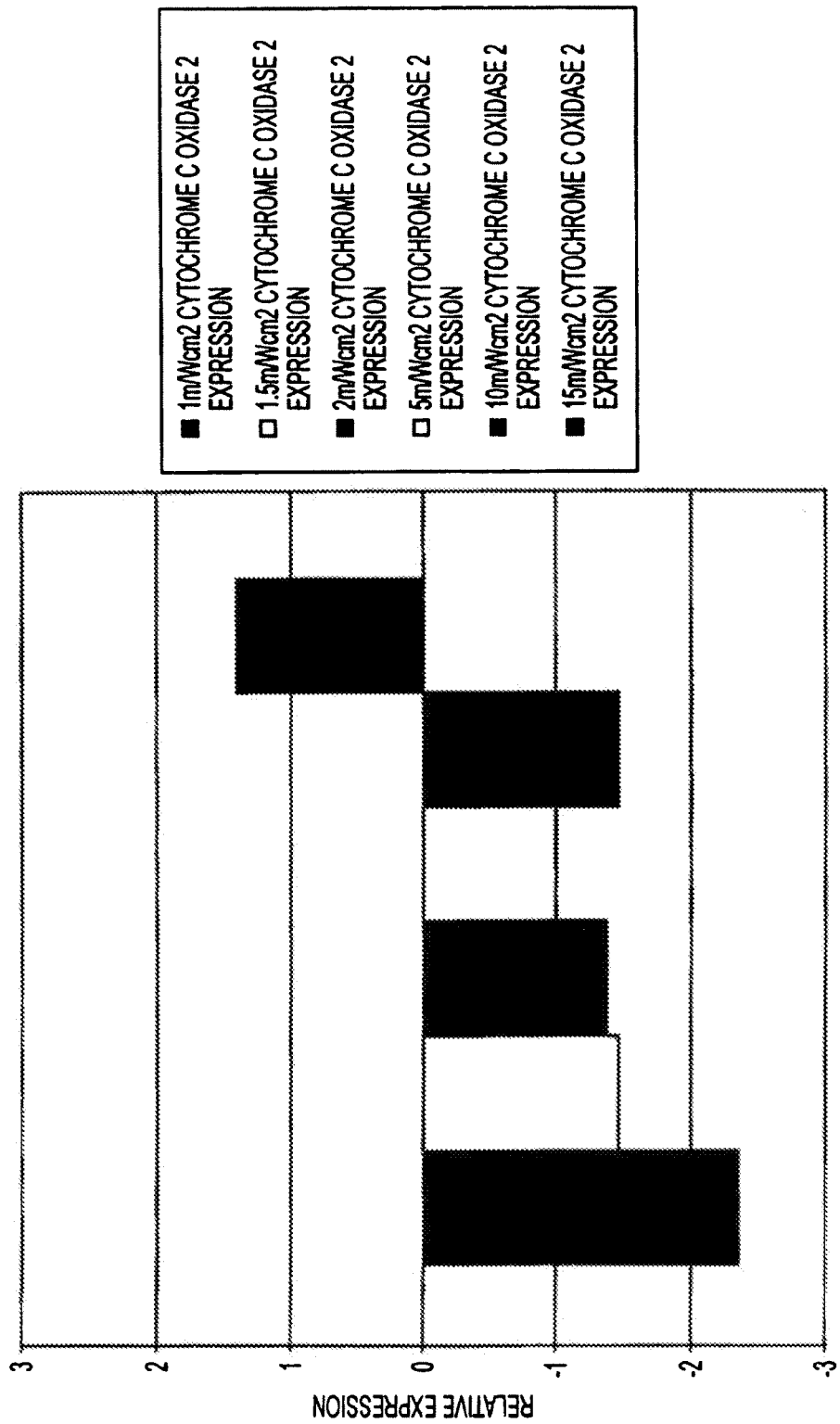
FIG. 4 is a chart which illustrates the RT-PCR expression of cytochrome c oxidase 2 in cultured human fibroblasts after exposure to narrowband, multichromatic electromagnetic radiation.
Figure 5:
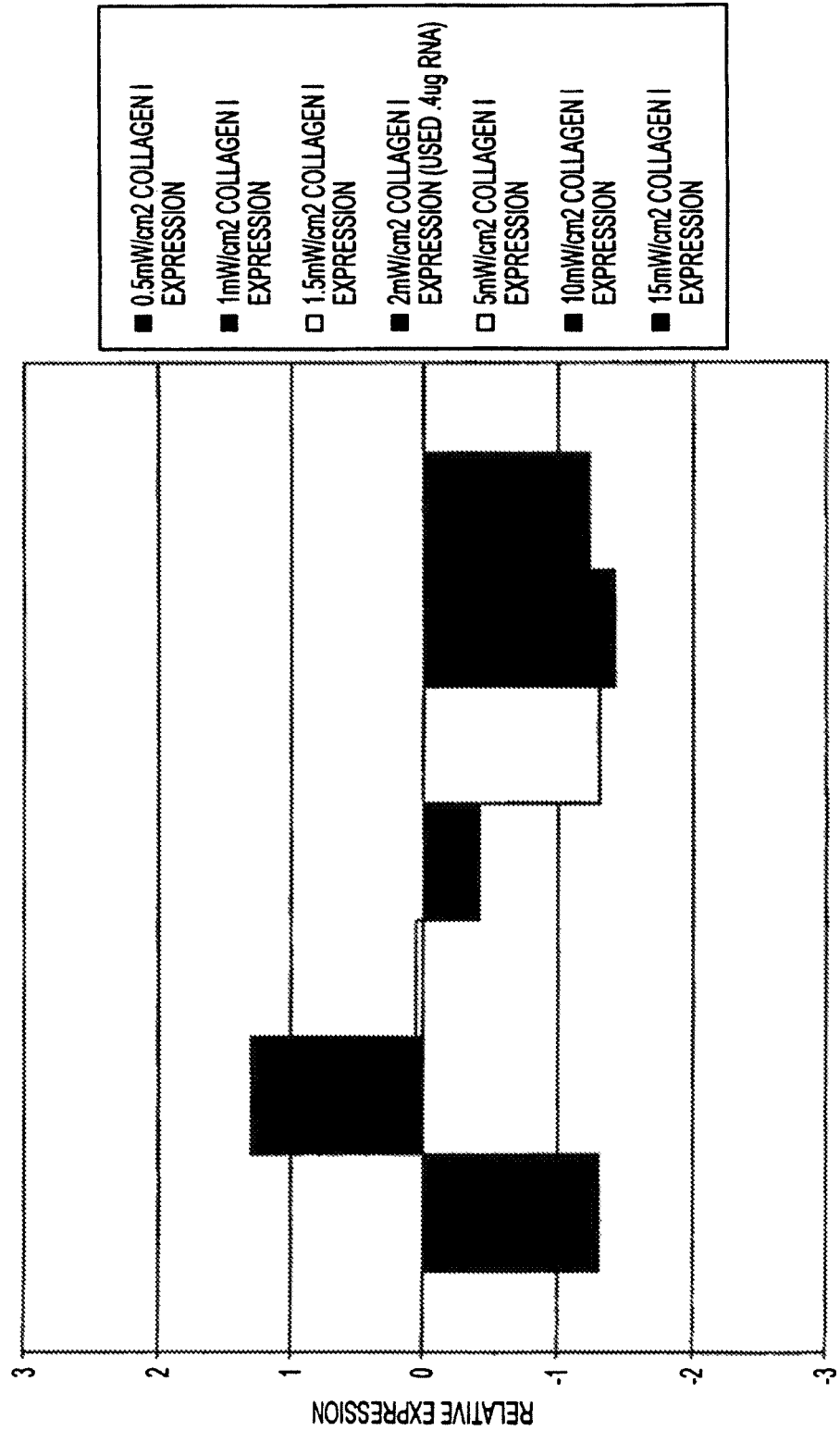
FIG. 5 is a chart which illustrates the RT-PCR expression of collagen I in cultured human fibroblasts after exposure to narrowband, multichromatic electromagnetic radiation.
Figure 6:
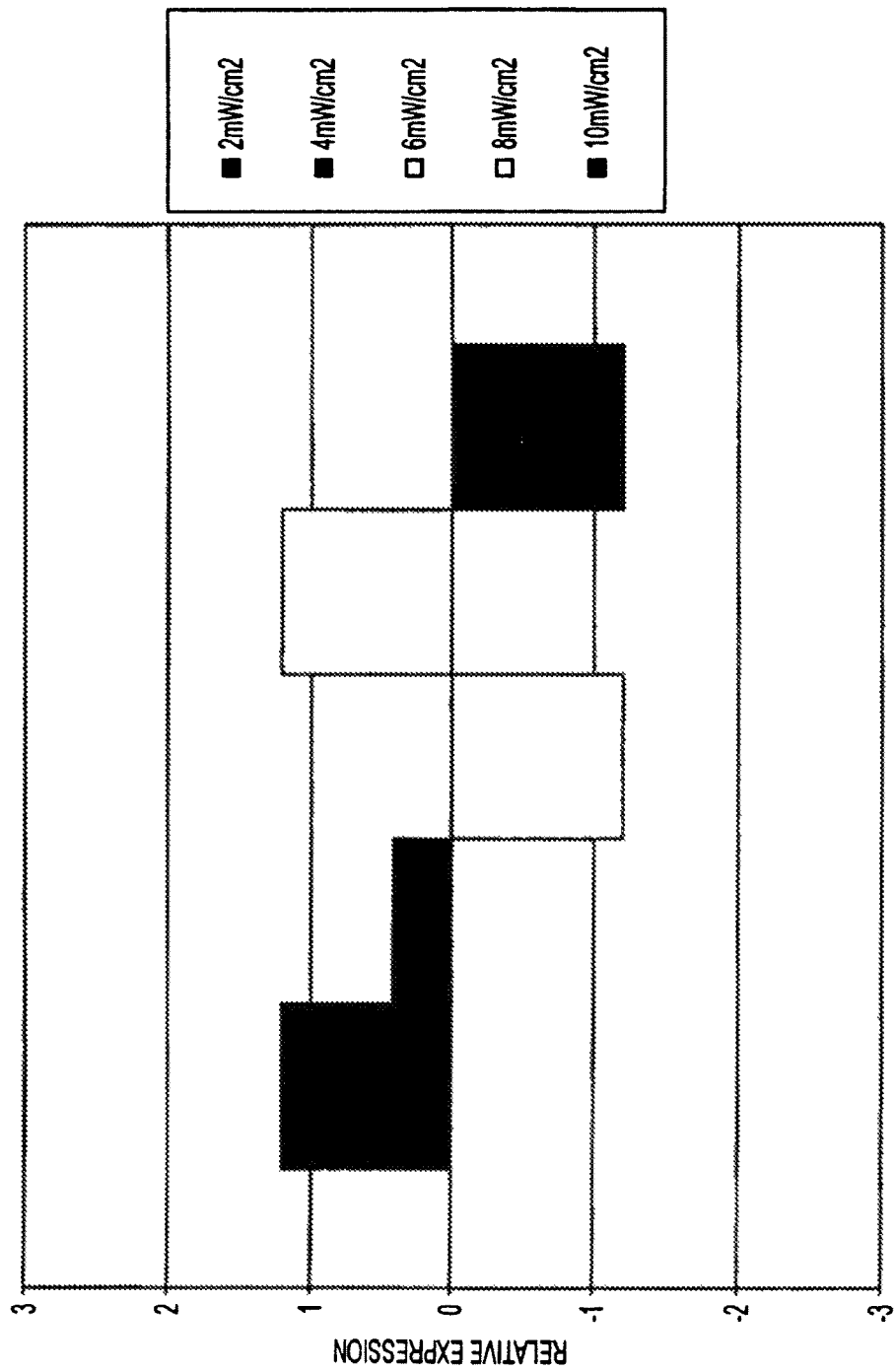
FIG. 6 is another chart which illustrates the RT-PCR expression of collagen I in cultured human fibroblasts after exposure to narrowband, multichromatic electromagnetic radiation.
Figure 7:
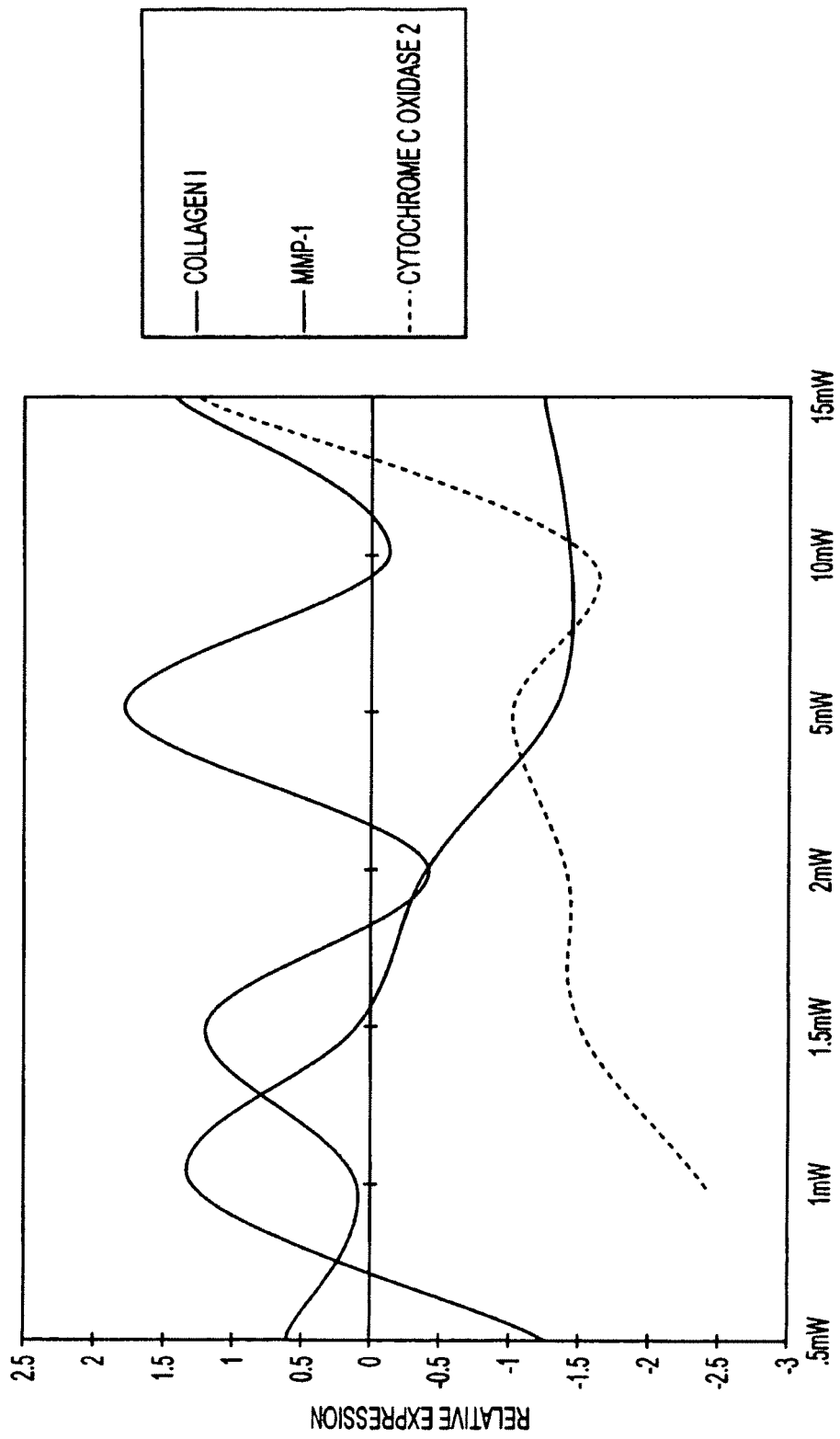
FIG. 7 is a chart which illustrates the RT-PCR expression of MMP-1, collagen I, and cytochrome c oxidase 2 in cultured human fibroblasts after exposure to narrowband, multichromatic electromagnetic radiation.
Figure 8:
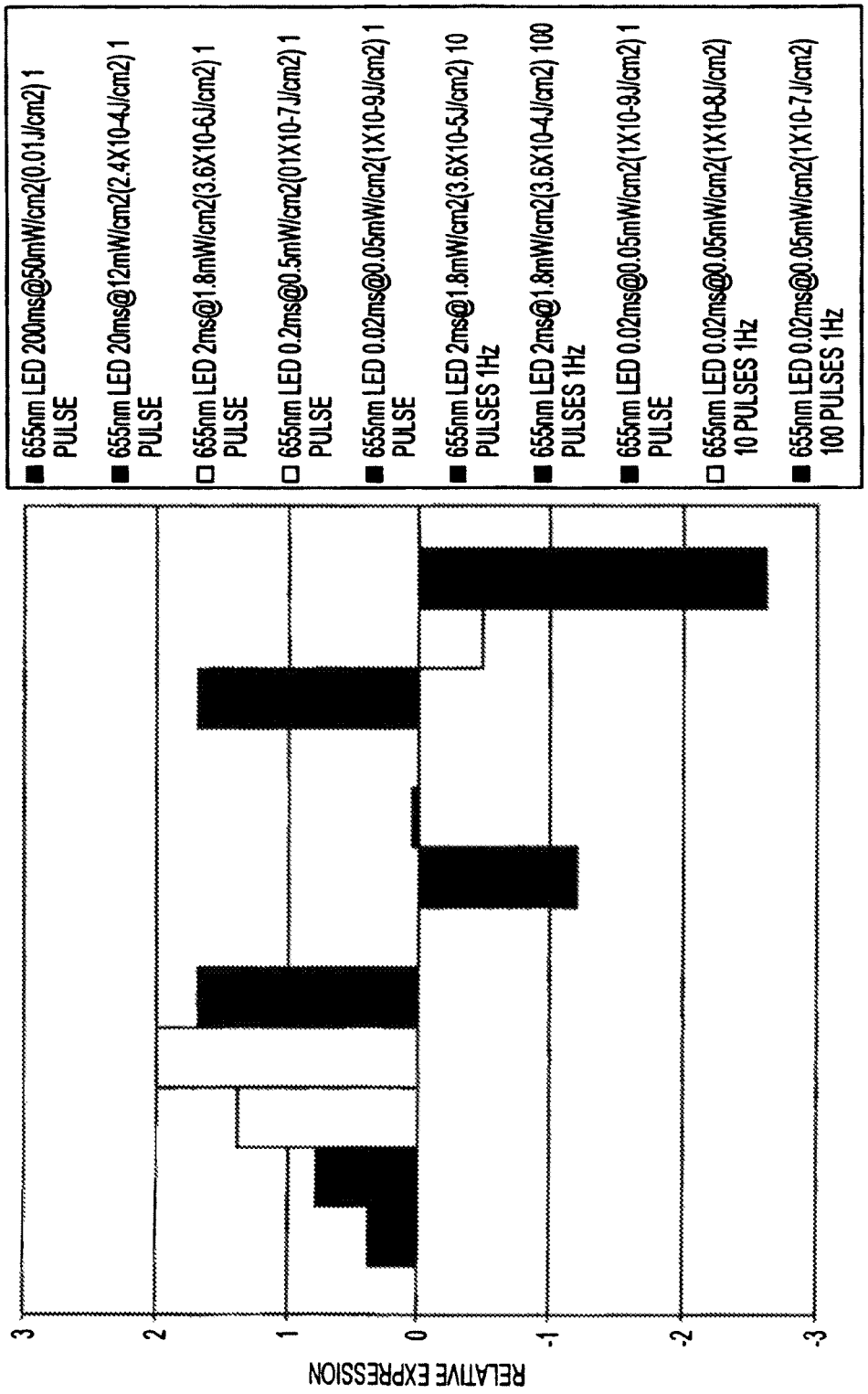
FIG. 8 is another chart which illustrates the RT-PCR expression of collagen I in cultured human fibroblasts after exposure to narrowband, multichromatic electromagnetic radiation.
Figure 9:
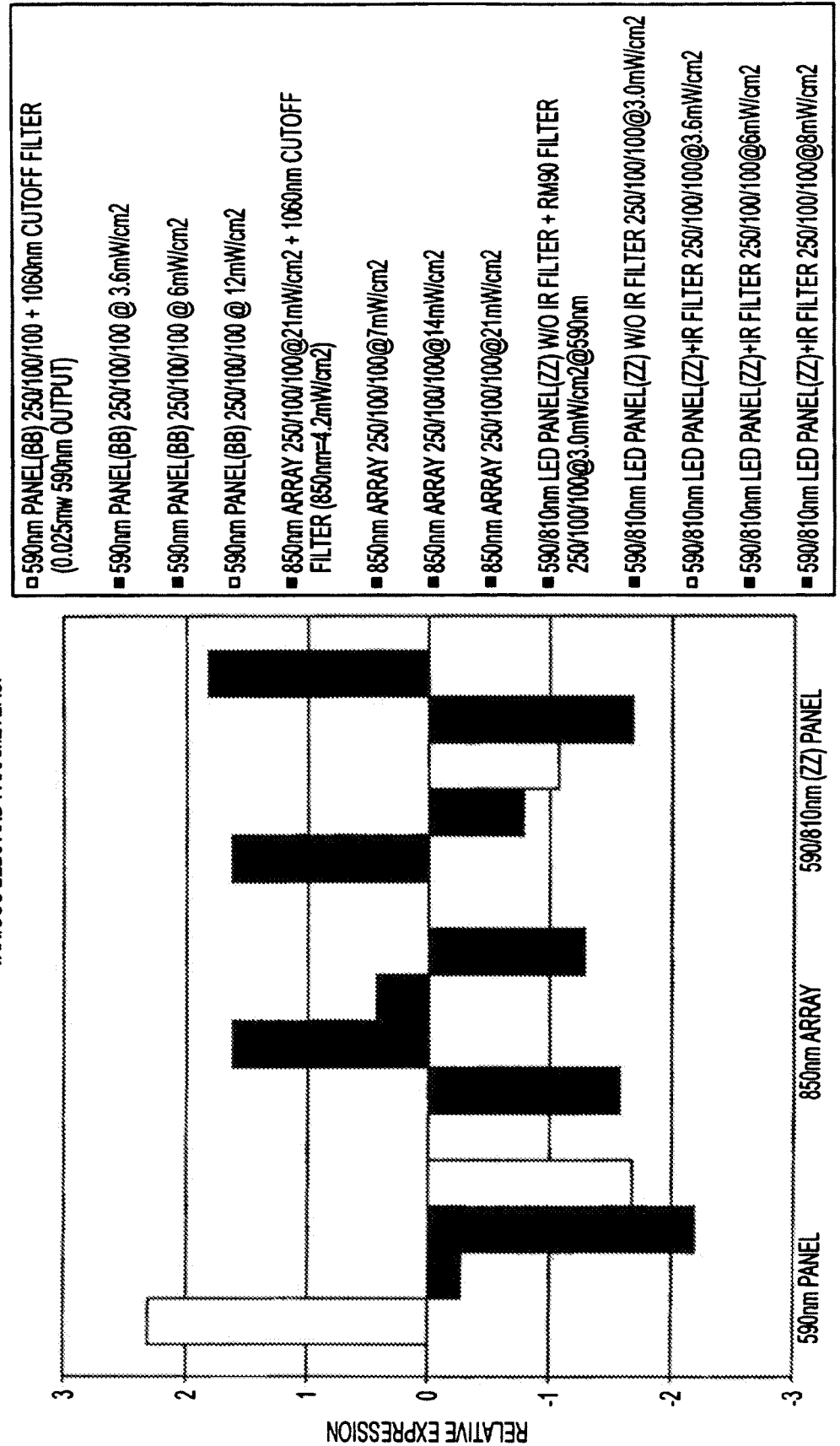
FIG. 9 is another chart which illustrates the RT-PCR expression of collagen I in cultured human fibroblasts after exposure to narrowband, multichromatic electromagnetic radiation.
Figure 10:
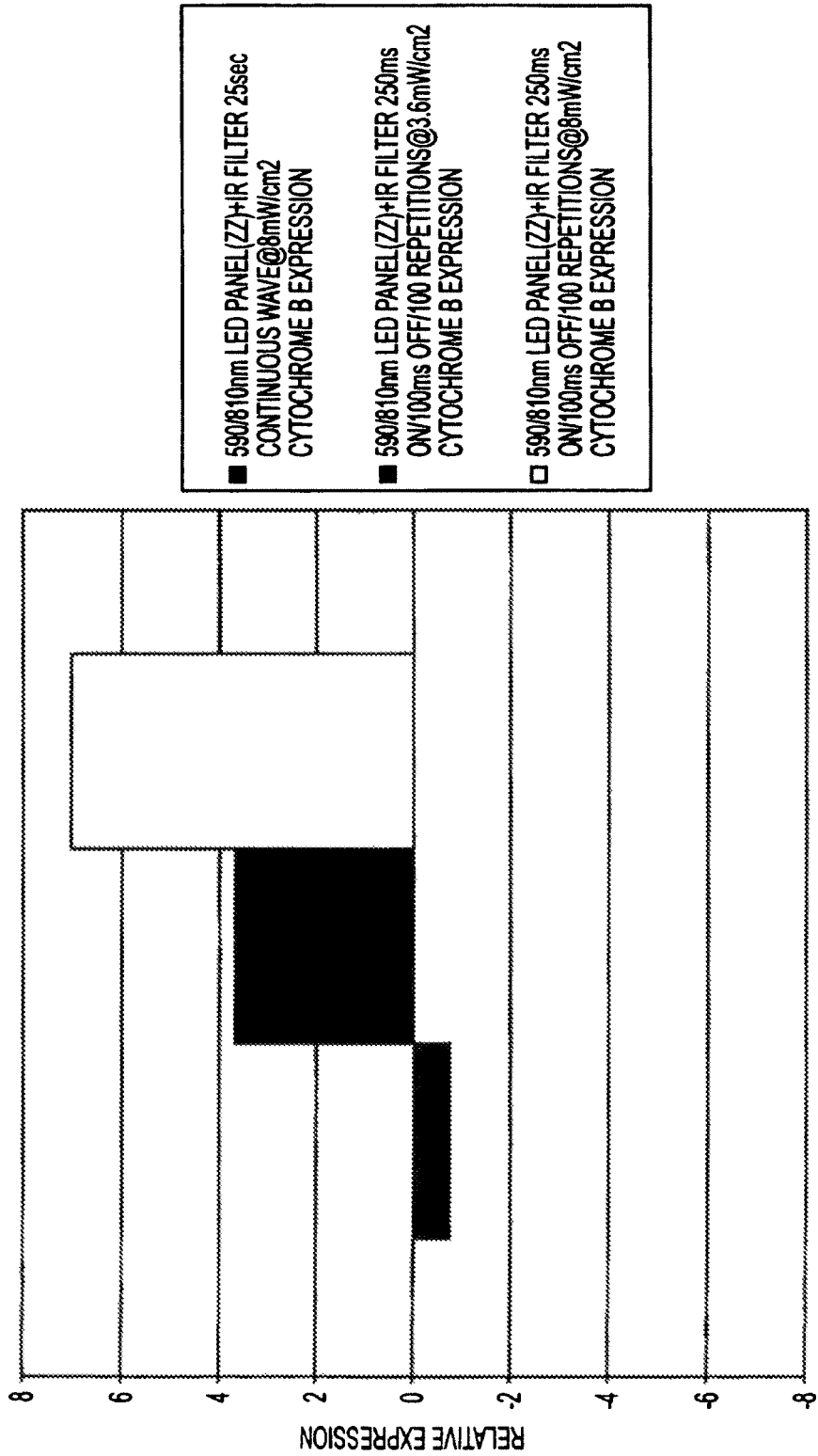
FIG. 10 is a chart which illustrates the RT-PCR expression of cytochrome b in cultured human fibroblasts after exposure to narrowband, multichromatic electromagnetic radiation.
Figure 11:
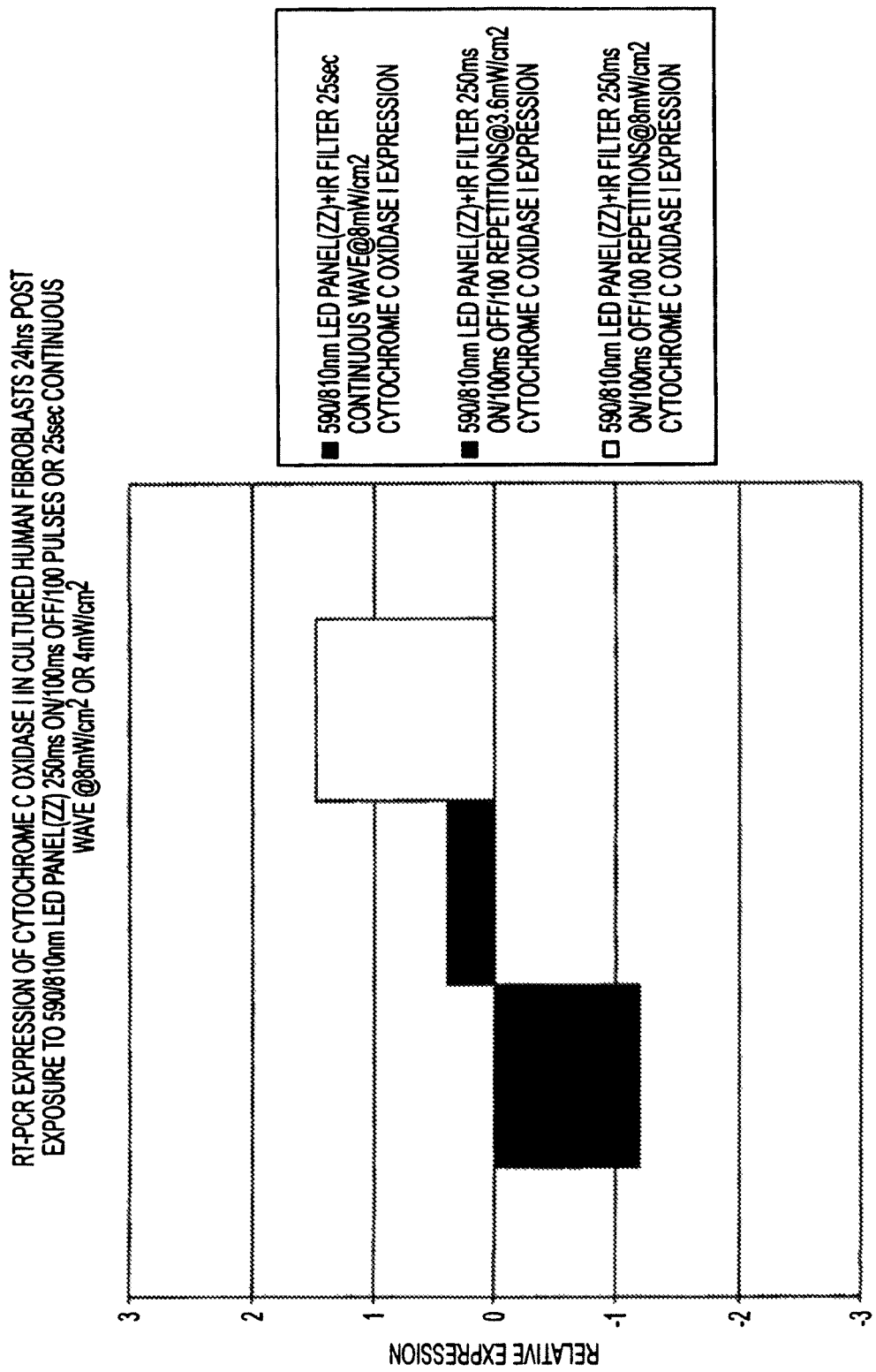
FIG. 11 is a chart which illustrates the RT-PCR expression of cytochrome b oxidase I in cultured human fibroblasts after exposure to narrowband, multichromatic electromagnetic radiation.
Figure 12:
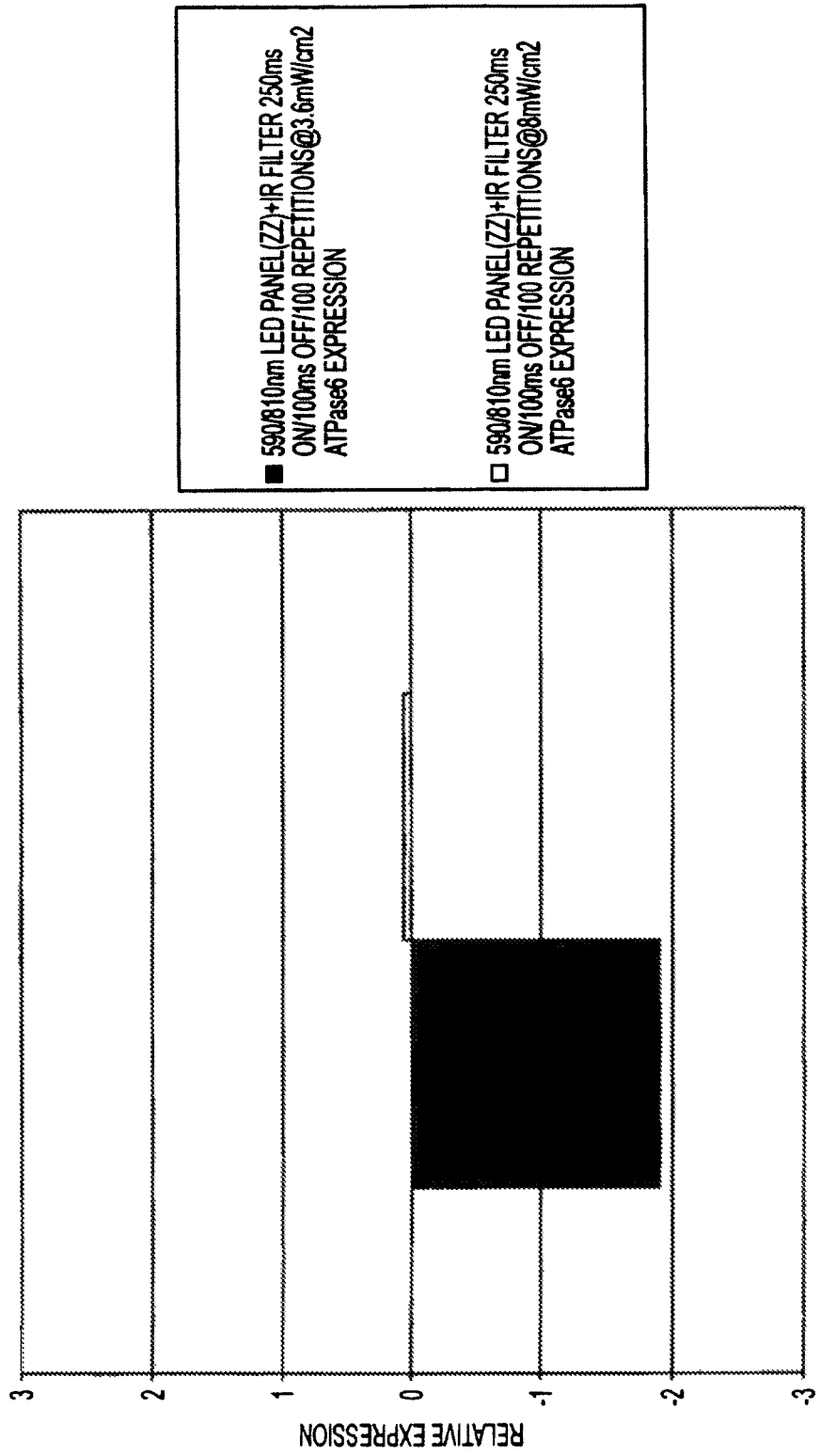
FIG. 12 is a chart which illustrates the RT-PCR expression of atpase6 in cultured human fibroblasts after exposure to narrowband, multichromatic electromagnetic radiation.
Figure 13:
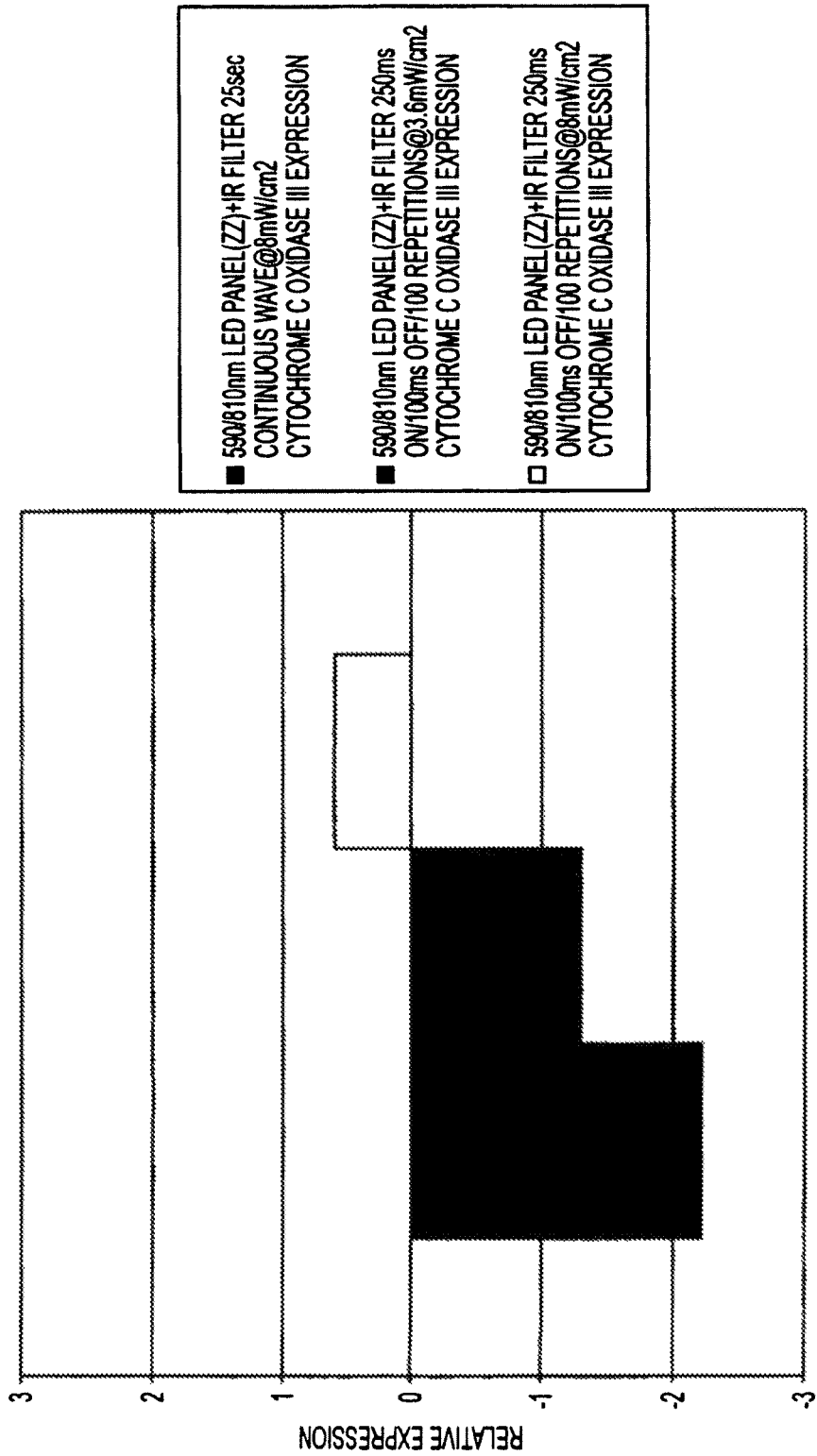
FIG. 13 is a chart which illustrates the RT-PCR expression of cytochrome c oxidase Ill in cultured human fibroblasts after exposure to narrowband, multichromatic electromagnetic radiation.
Figure 14:
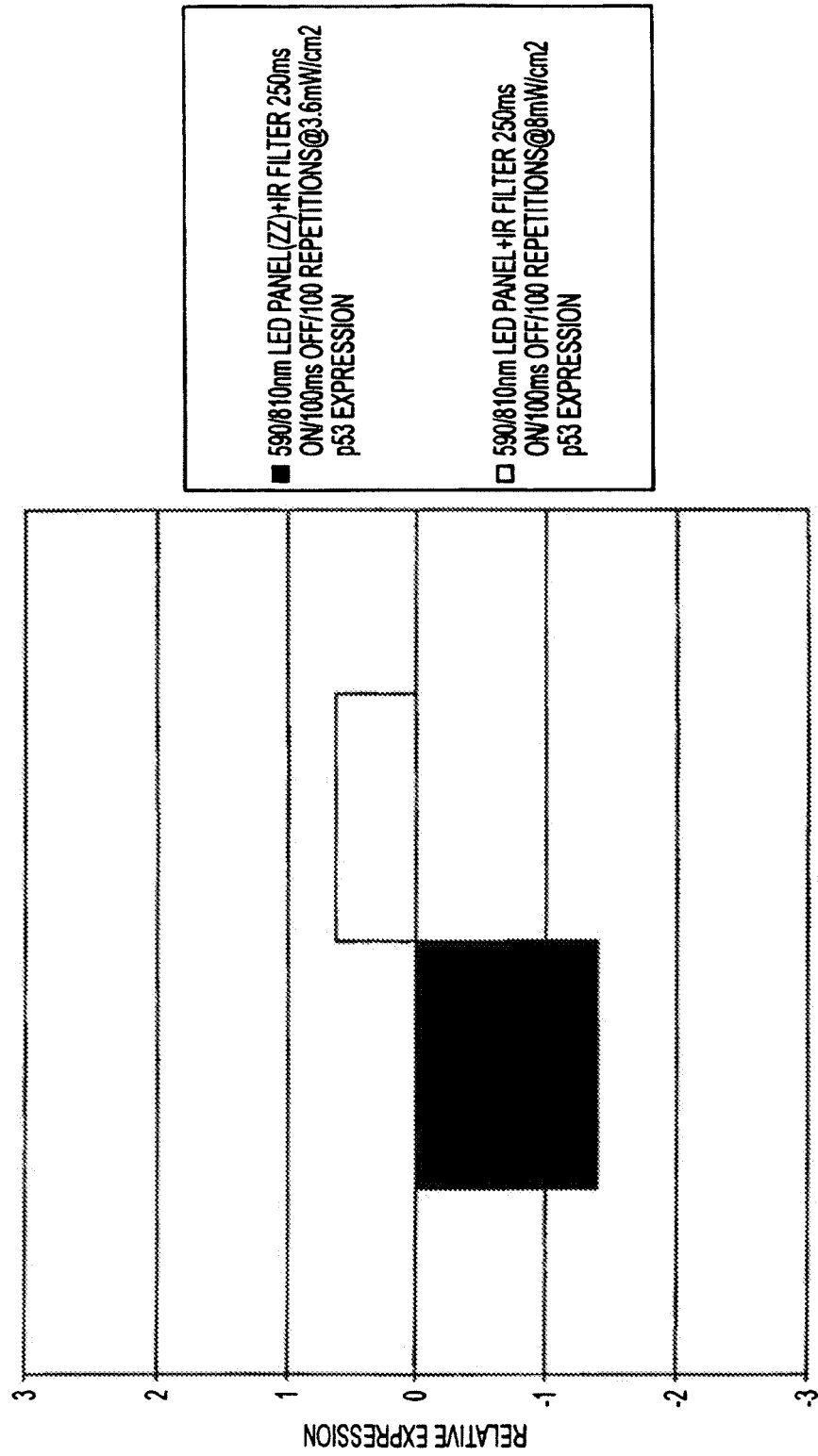
FIG. 14 is a chart which illustrates the RT-PCR expression of p53 in cultured human fibroblasts after exposure to narrowband, multichromatic electromagnetic radiation.
Figure 15:
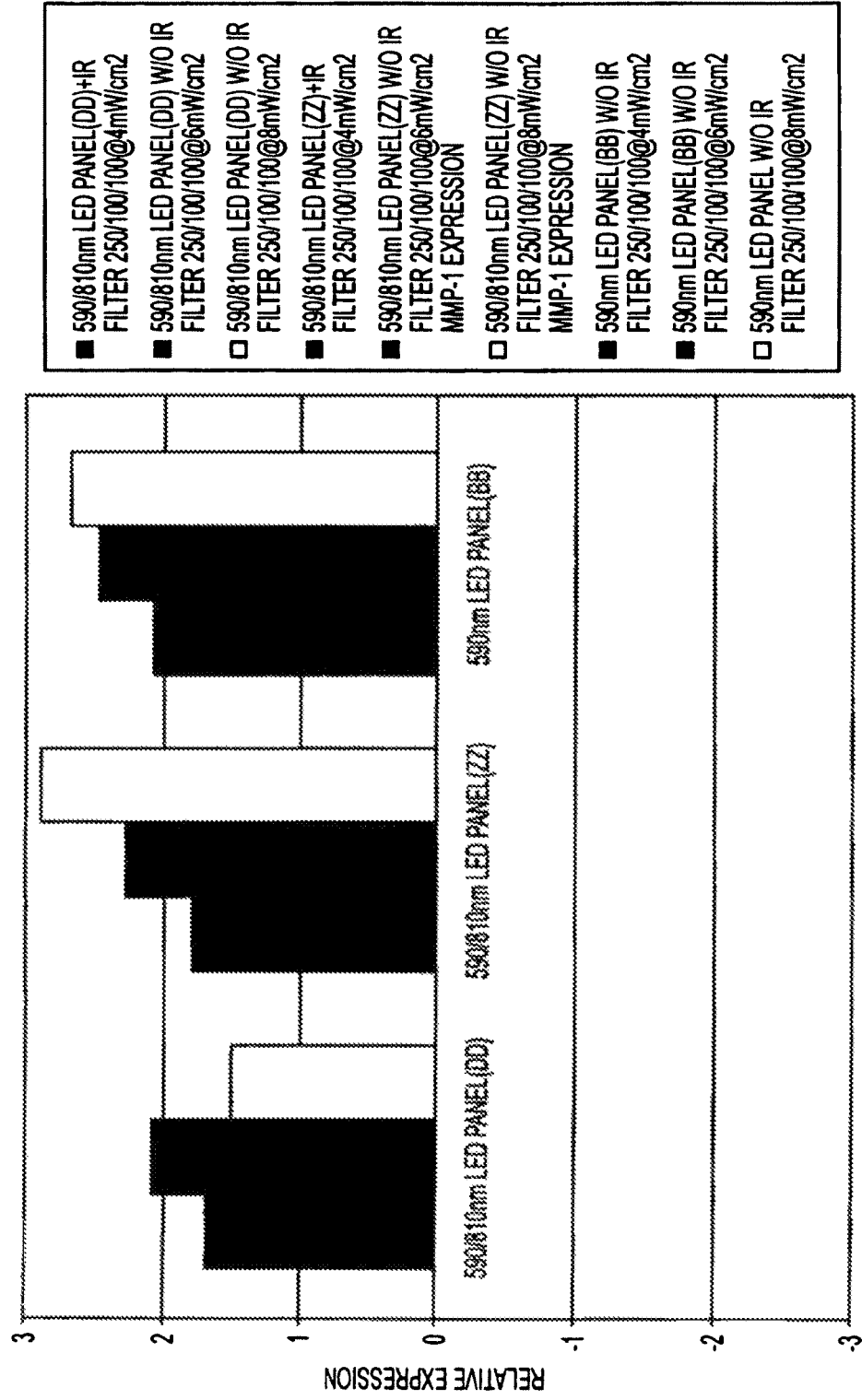
FIG. 15 is a chart which illustrates the RT-PCR expression of MMP-1 in cultured human fibroblasts after exposure to narrowband, multichromatic electromagnetic radiation with varying energy fluence.
Figure 16:
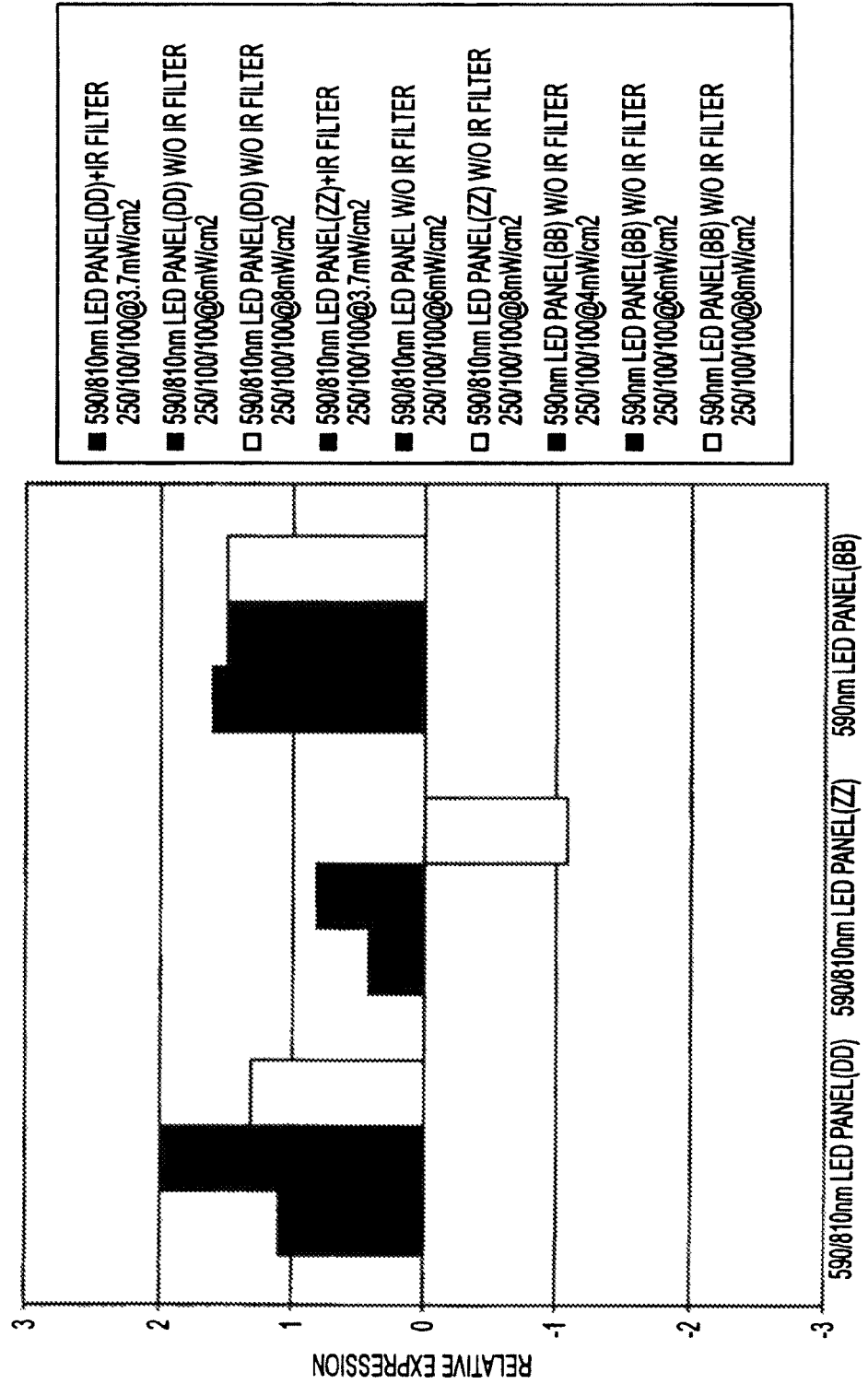
FIG. 16 is a chart which illustrates the RT-PCR expression of collagen I in cultured human fibroblasts after exposure to narrowband, multichromatic electromagnetic radiation.
Figure 17:
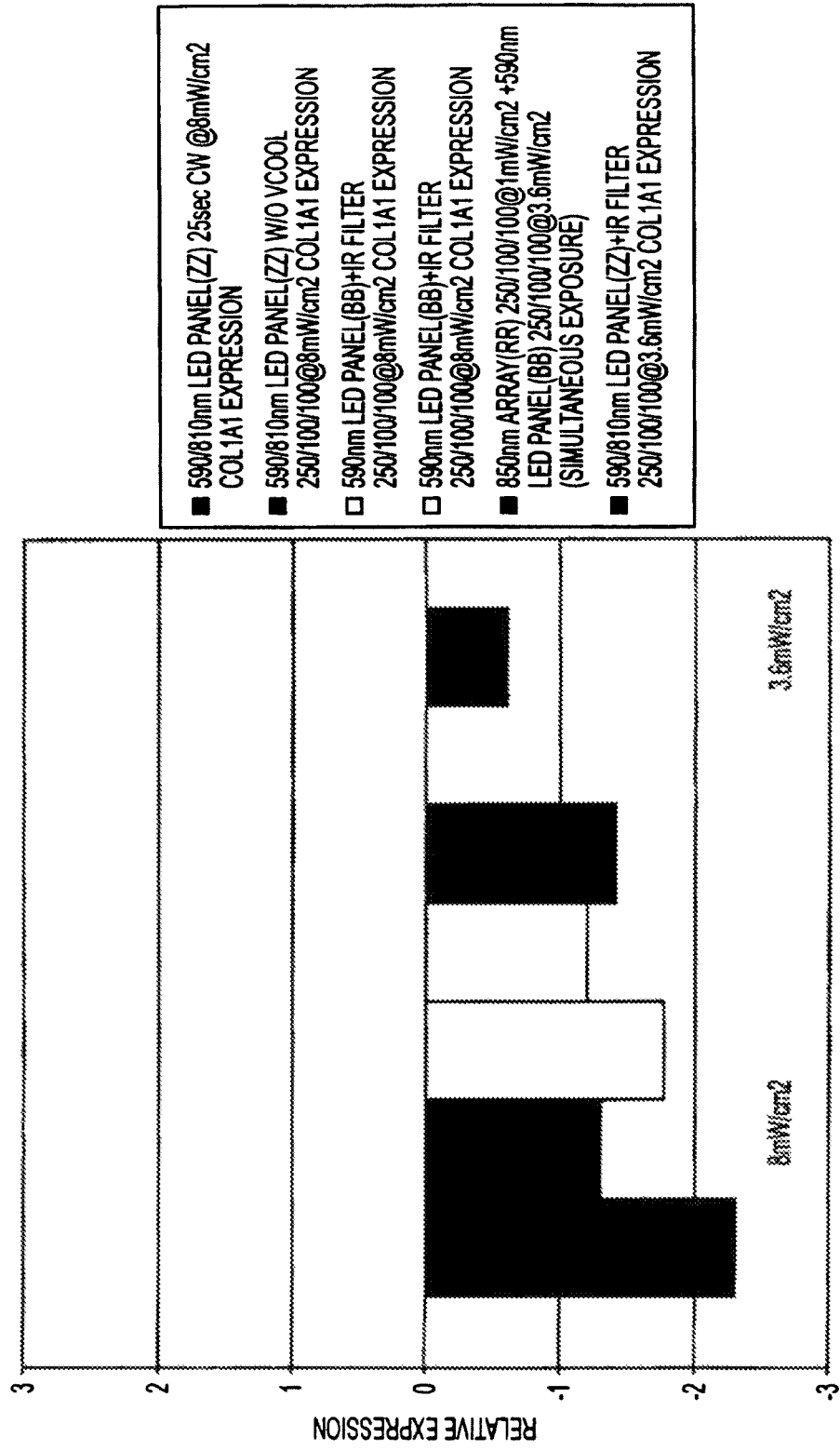
FIG. 17 is a another chart which illustrates the RT-PCR expression of collagen I in cultured human fibroblasts after exposure to narrowband, multichromatic electromagnetic radiation employing various light cycle regimen and filters.
Figure 18:
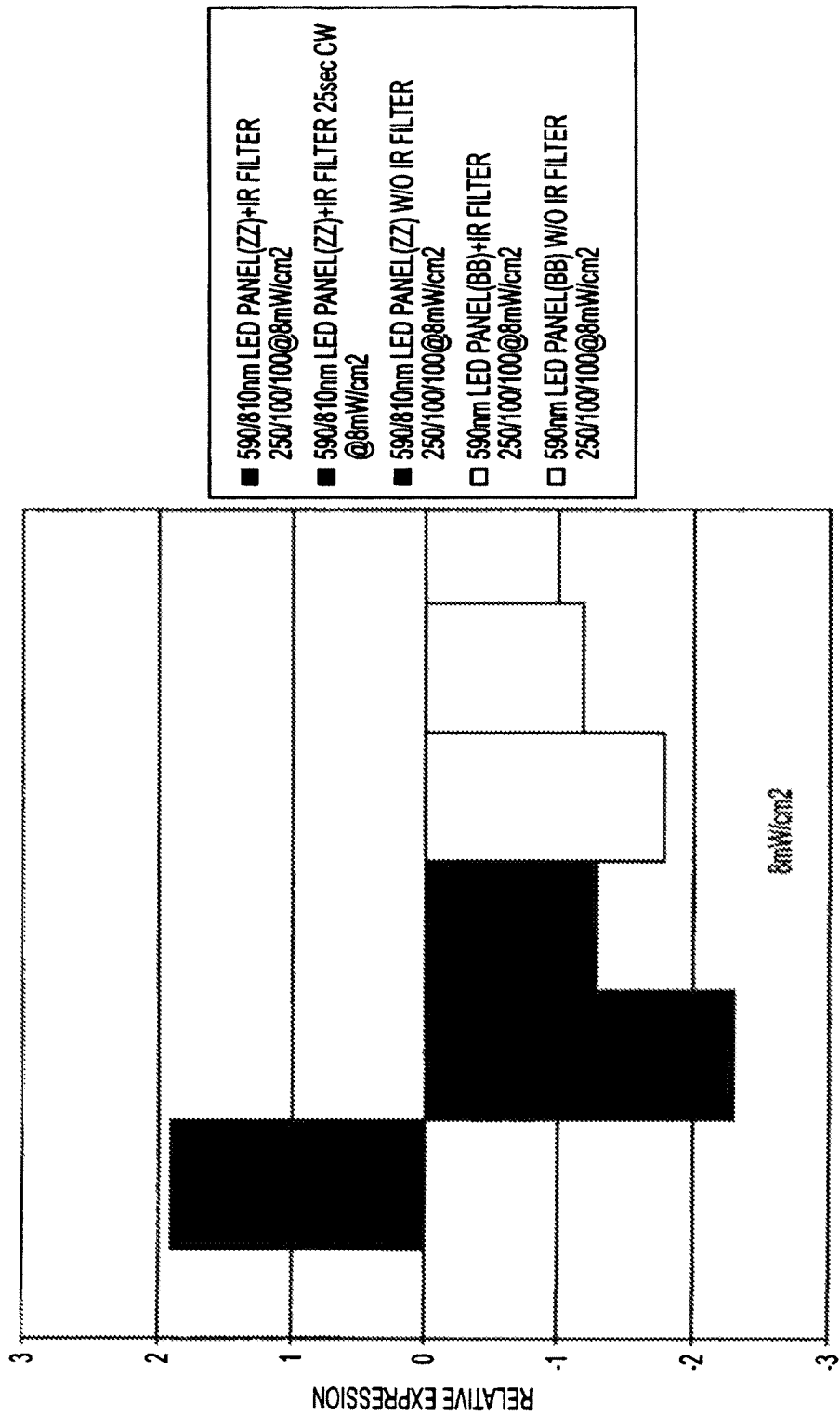
FIG. 18 is a another chart which illustrates the RT-PCR expression of collagen I in cultured human fibroblasts after exposure to narrowband, multichromatic electromagnetic radiation employing various light cycle regimen and filters.
Figure 19:
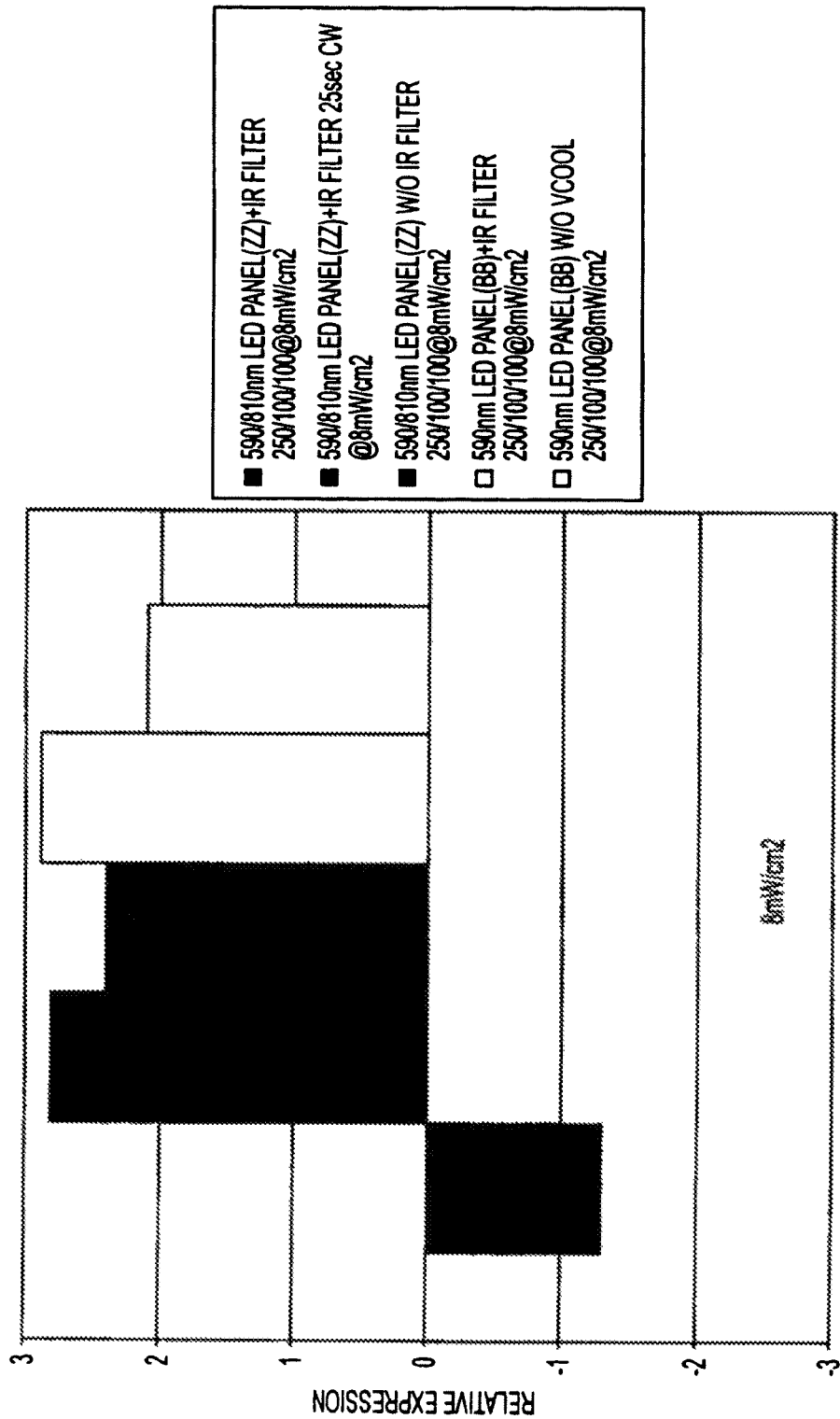
FIG. 19 is another chart which illustrates the RT-PCR expression of MMP-1 in cultured human fibroblasts after exposure to narrowband, multichromatic electromagnetic radiation employing various light cycle regimen and filters.
Figure 20:
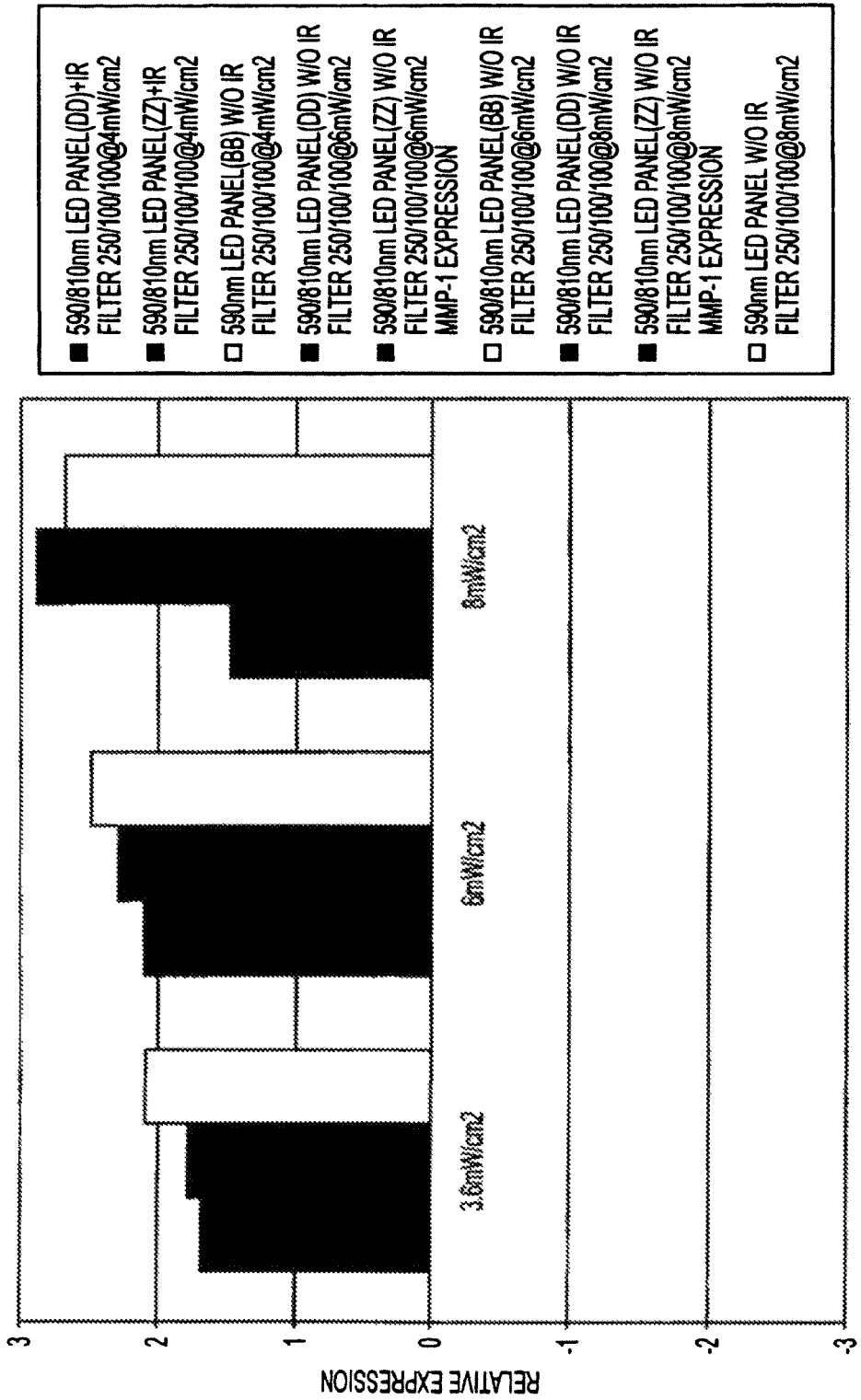
FIG. 20 is another chart which illustrates the RT-PCR expression of MMP-1 in cultured human fibroblasts after exposure to narrowband, multichromatic electromagnetic radiation employing various light cycle regimen and filters.
Figure 21:
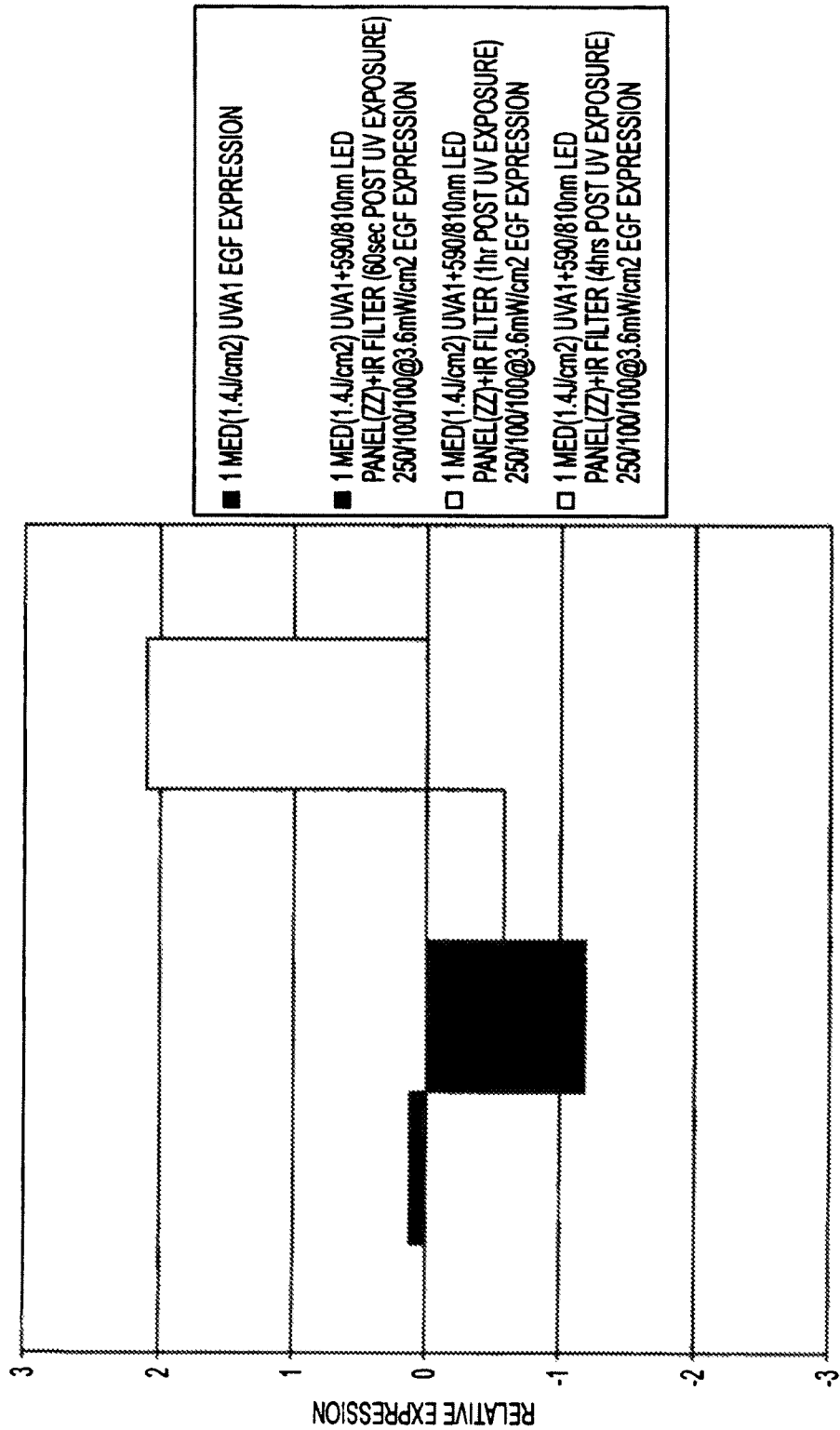
FIG. 21 is a chart which illustrates the RT-PCR EGF expression in cultured human fibroblasts after exposure to electromagnetic radiation simulator solar radiation.
Figure 22:
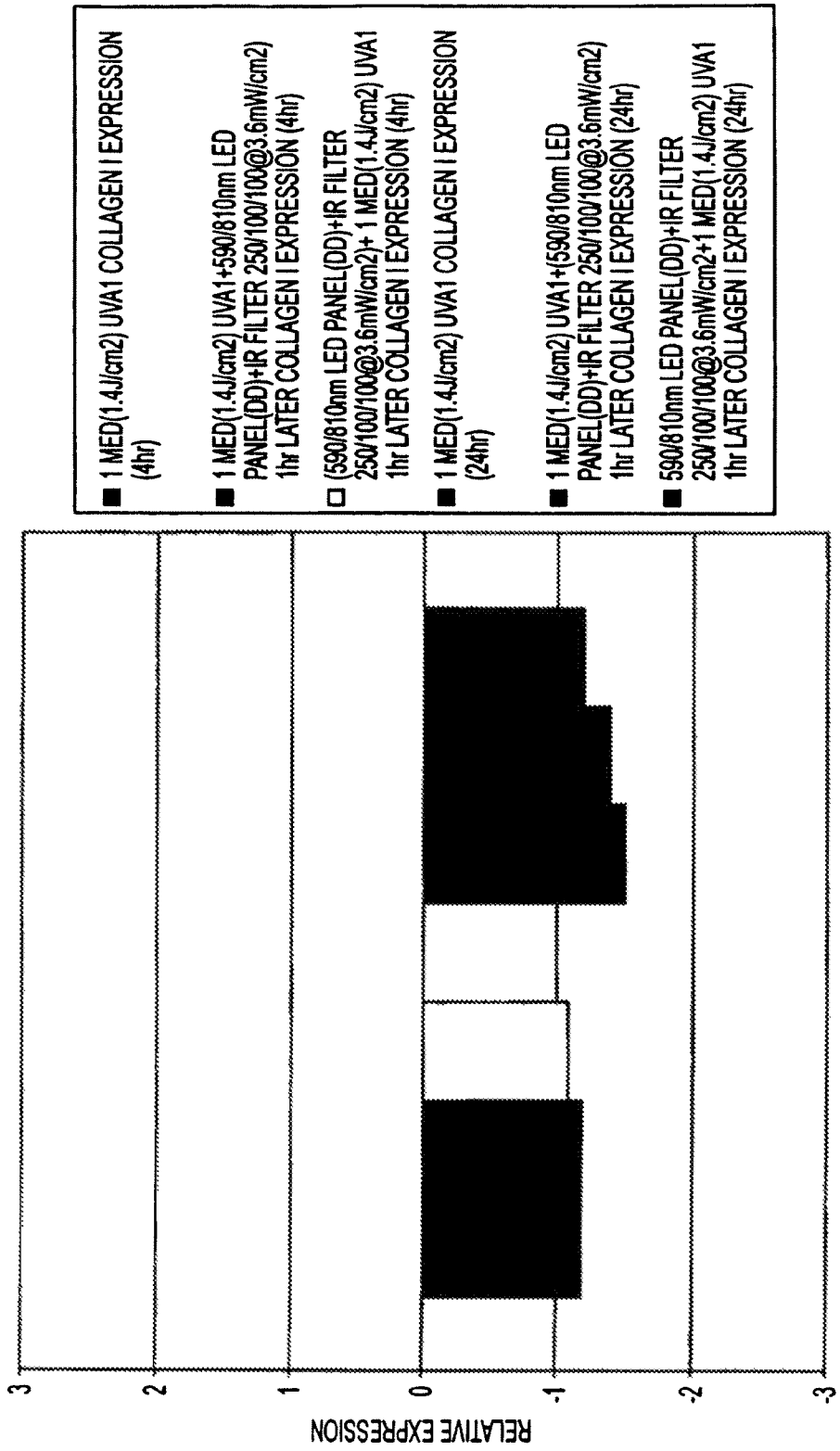
FIG. 22 is a chart which illustrates the RT-PCR expression of collagen I in cultured human fibroblasts after exposure to electromagnetic radiation simulator solar radiation.
Figure 23:
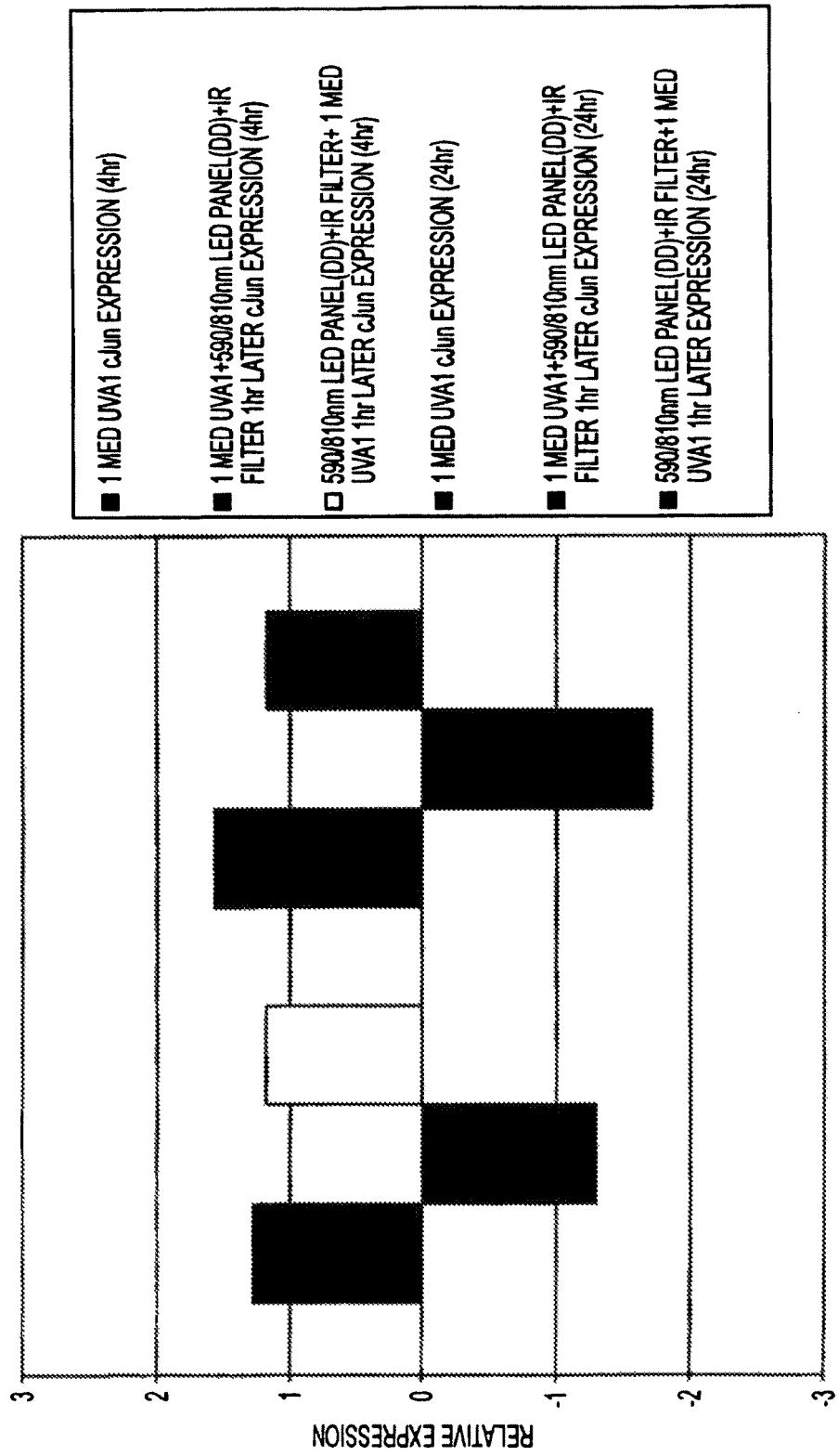
FIG. 23 is a chart which illustrates the RT-PCR expression of cJun in cultured human fibroblasts after exposure to electromagnetic radiation simulator solar radiation.
Figure 25A:
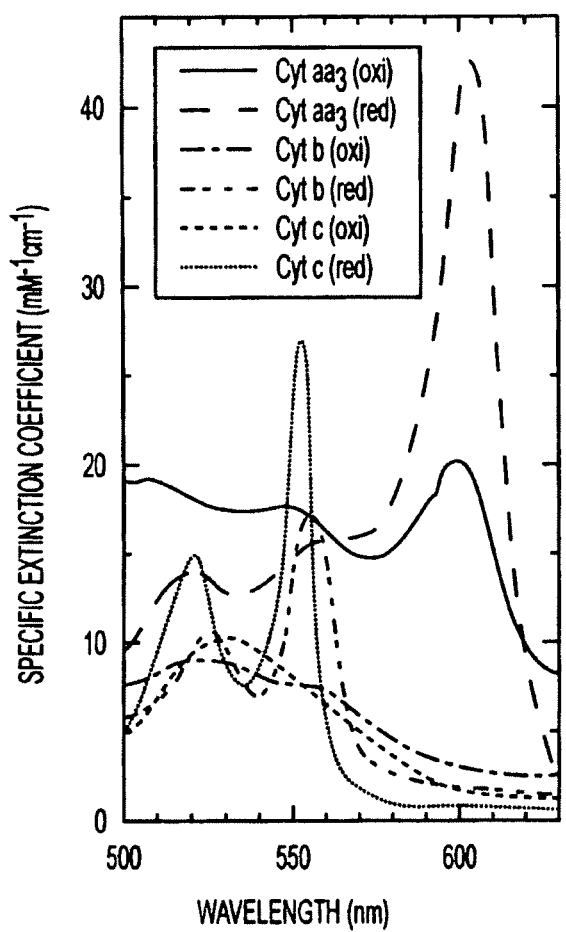
FIG. 25(*a*) illustrates the specific extinction coefficients of various cytochromes at various wavelengths.
Figure 25B:
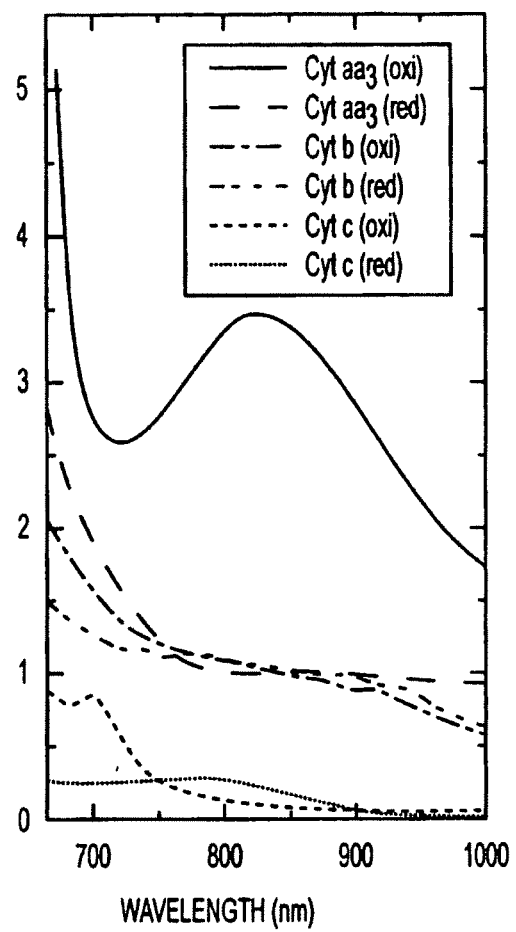
Figure 27:
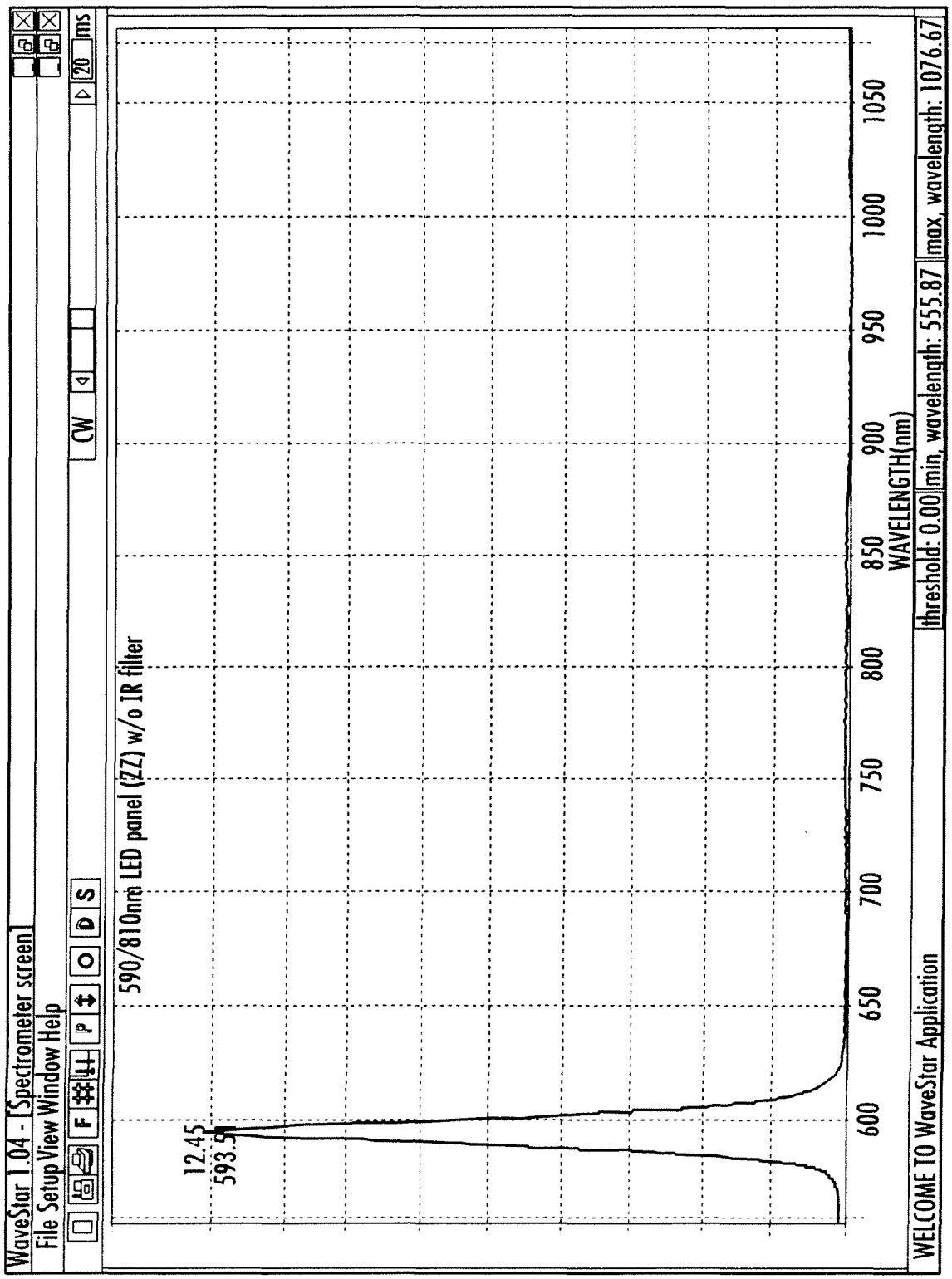
FIG. 27 shows the emission or spectral output of the LED with dominant visible and secondary infrared (IR) peaks and their relative intensity and shape.
Figure 28:
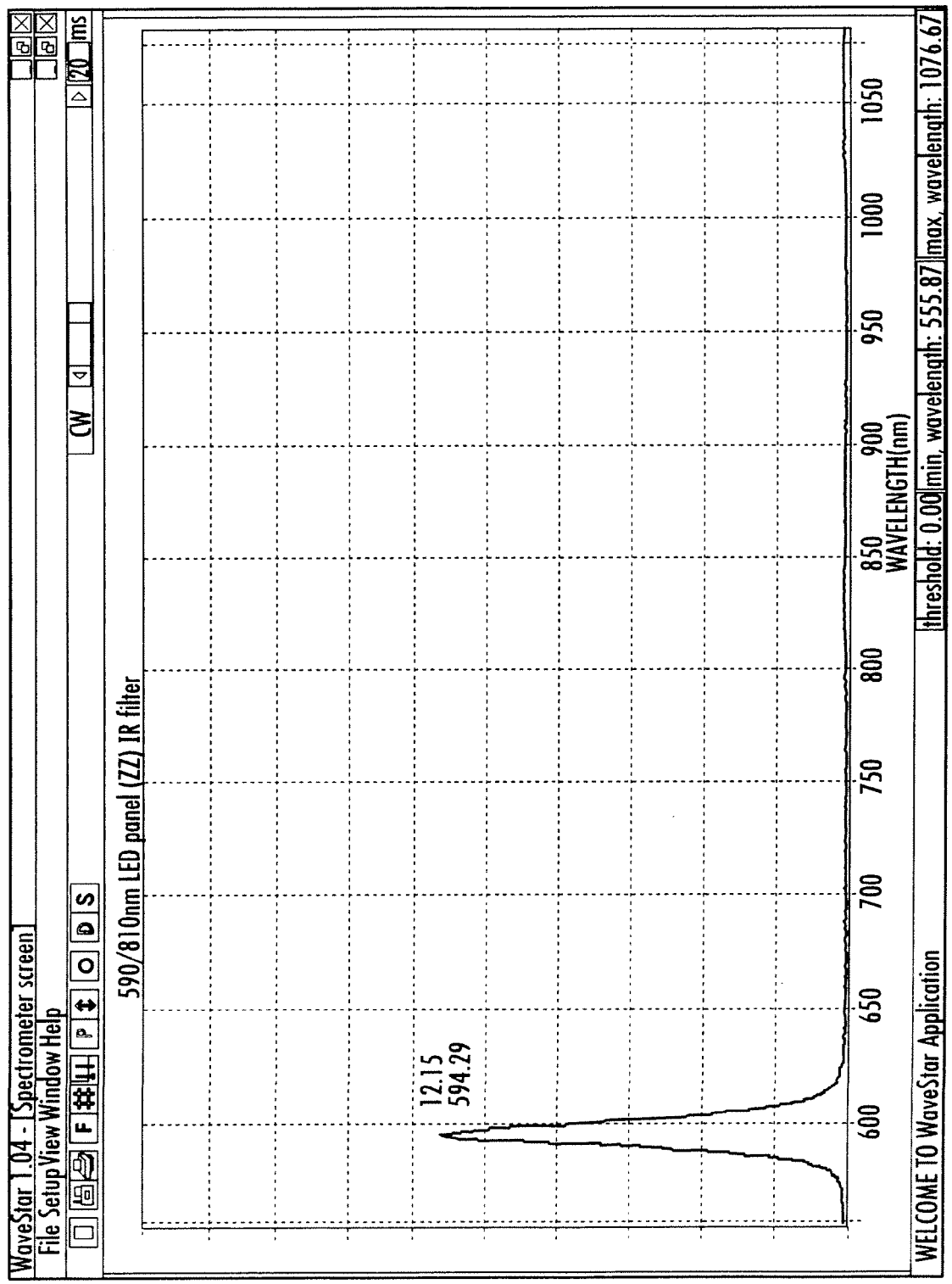
FIG. 28 shows the same LED emission with a selective infrared filter in place which reduces both the visible and IR output, but alters the relative ratio of visible to IR light as well as altering the shape of the IR spectral output curve.
Figure 29:
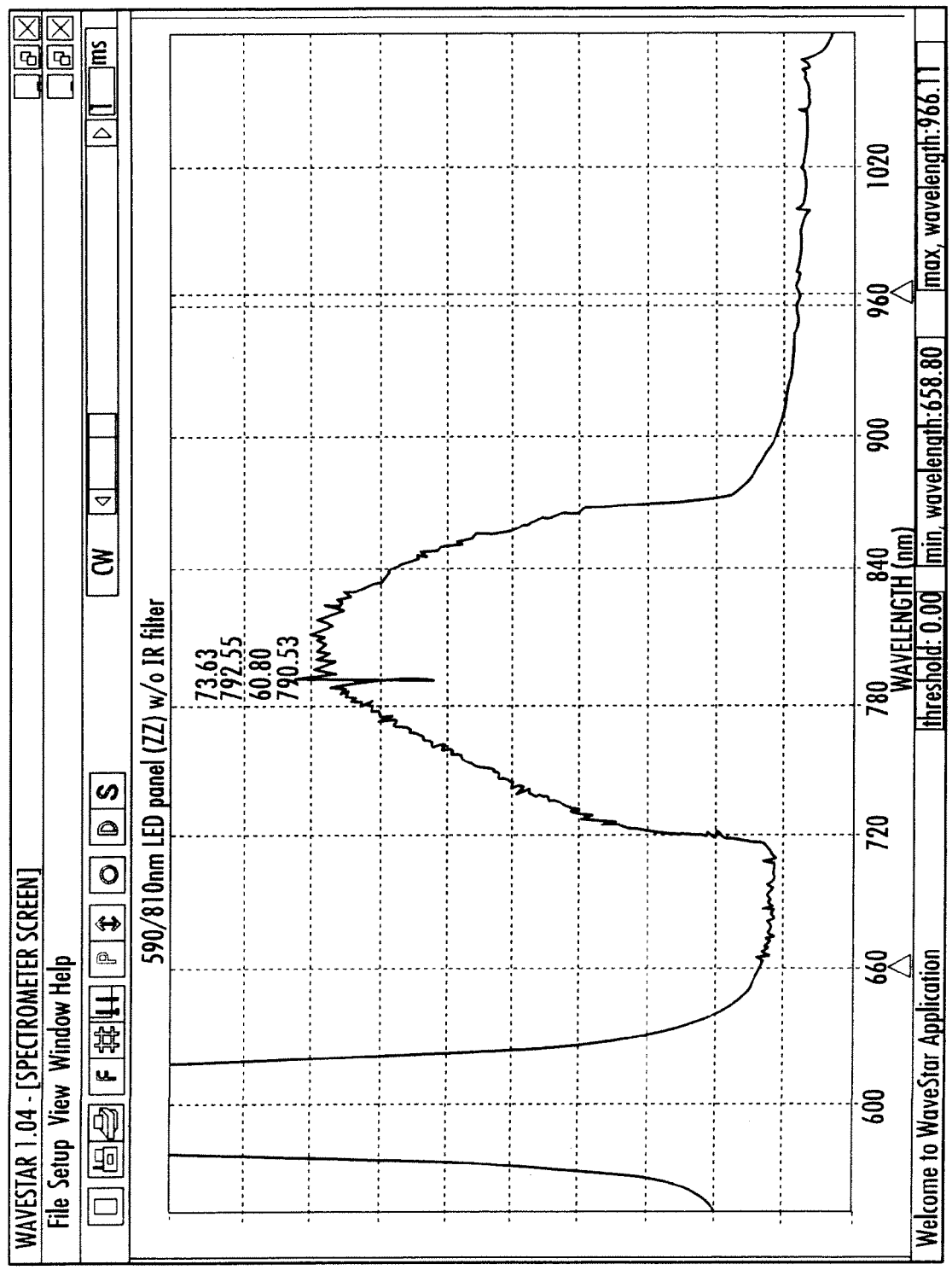
FIG. 29 shows the emission or spectral output of the LED with dominant visible and secondary infrared (IR) peaks and their relative intensity and shape.
Figure 30:
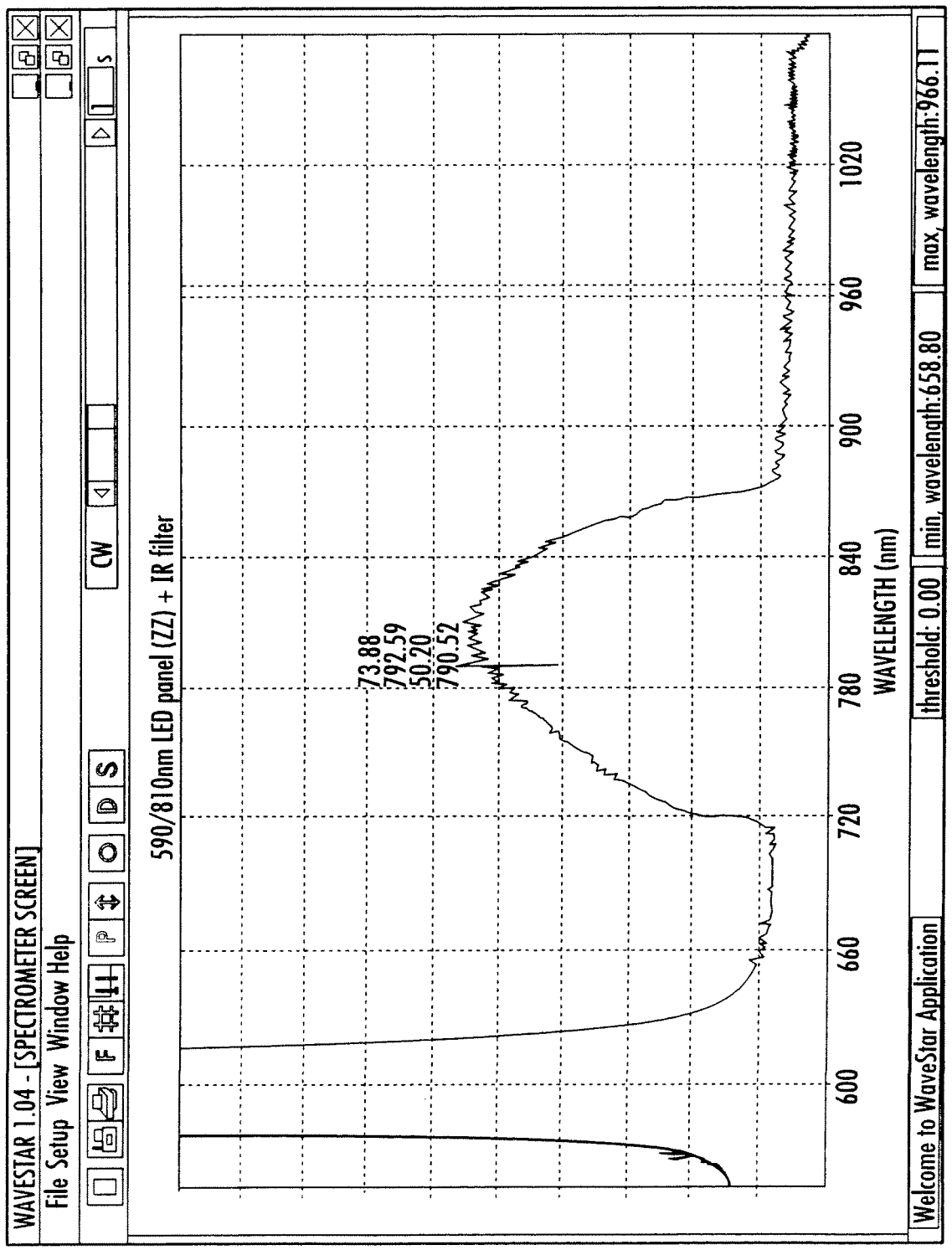
FIG. 30 shows the same LED emission with a selective infrared filter in place which reduces both the visible and IR output, but alters the relative ratio of visible to IR light as well as altering the shape of the IR spectral output curve.

As embodied and broadly described herein, the present invention is directed to method and devices for the regulation of cell proliferation and gene expression and, in particular, the inhibition of photoaging of the skin, and the revival of necrotic cells. As well, the invention is directed toward a system and method for rejuvenating cells in various stages of necrosis.

Photoaging of the skin occurs through many mechanisms, including, for example, environmental factors such as tobacco smoke, exposure to the sun, and poor health, to name a few. These events can triggers an inflammatory process in the skin and the associated cellular mechanisms. There is also a more chronic low-level type of injury that does not produce a sunburn reaction, but which produces the changes of chronic photoaging. Chronological aging of the skin and photoaging and other environmentally induced changes share many or in some cases, all of the same pathways as UV induced photoaging of the skin. These pathways involve up and/or down regulation of cell proliferation and also alterations in the level of expression of many different types of genes.

It was surprisingly discovered that, this combination of regulation of cell proliferation and regulation of gene expression, is responsible for photoaging of the skin and other cells and tissues, and thus, photoaging could be reversed or at least ameliorated by affecting these same processes. Accordingly, one embodiment of the invention is directed to identifying and correlating the phenotypic and genotypic expression characteristics of photoaging and other skin and cell-associated disorders. Once identified, correlated maps can be compiled and collected into a data base to allow for the rapid and efficient identification of similar disorders and conditions for the purpose of tailoring appropriate treatment. Further, once identified, treatment and appropriate intervention and prevention methods can be used to halt or even reverse the appearance and genotypic characteristics of photoaging. Thus, the invention is not directed to artificially hiding or covering up aspects associated with aging, but actually reversing the processes and mechanisms associated with aging-related phenomena.

A further embodiment of the invention is directed to applying these same mechanisms and tools to other cells such as stem cells (completely undifferentiated cells) and progenitor cells (partially differentiated cells). By altering the cell cycle, cell proliferation, and/or gene expression characteristics of these cells along defined parameters, it is possible to determine differentiation pathways and to create or recreate cells, tissues and other cell structures for disease therapy and prevention, and wound healing.

Methods to modulate cell proliferation and gene expression include exposure to electromagnetic radiation in an amount or dose that is sufficient to stimulate the desired effect (e.g. see U.S. Pat. Nos. 6,398,753, 5,837,224, and 6,130,254; and U.S. Patent Application Nos. 2002/0028185, 2001/0053347, 2003/0004556, 2003/0004499, and 2002/0123746, all of which are specifically and entirely incorporated by reference). For example, exposure of skin to LED can stimulate or inhibit the expression of various gene products. These same methods can be used to cause stimulation or inhibition of cell proliferation and cell cycle modulation in these cell populations. Further, photomodulation can be used in combination with certain oral agents (for systemic affects) or topical agents (for localized affects) (e.g. vitamin A, retin A, retinol), for a desired effect unachievable with either stimulant used individually.

The types of cells that can be affected include, but are not limited to skin cells (reversal of photoaging), nerve cells (disease prevention and treatment), stem cells (tissue reconstruction), cells of hair follicles (hair growth or inhibition), cells of the immune system including cells intimately involved with the process of inflammation (due to disease, infection, or congenital disorder), wound repair, and combinations thereof. Modulation can be achieved by exposing cells to electromagnetic radiation (e.g. photomodulation) such as, preferably, visible light, (e.g. purple, blue, green, yellow, orange, red), infrared radiation, ultraviolet light (UVA, UVB, UVAI, UVA2, or combinations thereof), or combinations of any. Preferred exposure strengths and exposure times are as set forth in the attachments hereto, but may include pulsed exposures, continuous and periodic exposures.

Modulation of Gene Expression

Ultraviolet light injury triggers reactive oxygen species and a series of cell signaling events called kinase cascades. One of the final common pathway in the up and down regulation of fibroblast activity is through AP-1 which up regulates and increases the production of various MMP's including MMP 1 (collagenase 1 or interstitial collagenase synthesis), MMP 9 (gelatinases B) and MMP 3 (stromelysins 1). The production of these MMP enzymes results in the breakdown of collagen, elastin and ECM in the dermis of the skin. Simultaneously the actual production of collagen I and other structural proteins may be diminished or down regulated thus further accelerating the process.

The aging of living cells, tissues and organs may be related to free radical exposure and oxidative stress. To apply this model to aging skin, chronological aging results from a decrease antioxidant defense mechanisms while UV photoaging and other environmental stresses can be thought of as increasing oxidative stress. The net result of decreased antioxidant defense or increased oxidative stress is increase production of (ROS) or free radicals.

Modulation of Gene Activity

Increased ROS production in the skin stimulates cell signaling or signals transduction pathways, which produce altered gene activity. Damage to structural proteins (e.g. damage, disruption and fragmentation of collagen caused by UV light) alters proteins, structure and function which in turn changes cell signaling and may alter gene activity. Another possible outcome of increased ROS production is the production of DNA mutations, which then alters gene structure and thus may alter the normal structure and function of cells.

Much of the variation in the human state, as far as disease and response to environmental insults may be mediated by relatively small differences in the genetic make-up from one individual to the next. Single nucleotide polymorphisms (SNPs) are currently being very actively investigated as a means of identifying and potentially predicting the differences in biological responses of humans and other animals. For example, characterization of SNPs may allow prediction of whether a patient is more or less likely to develop a specific disease or tumor and thus take known preventative measures. Another possible application is the use of SNPs to screen individuals before placing them on a prescription drug to identify those individuals who might be more likely to develop serious side effects and thus avoid the use of that drug. Another potential novel use of SNPs is to identify the haplotype or patterns of SNPs, which are associate with, for example, chronological aging of the skin. Some individuals and families have reduced risk of skin cancers or simply look younger than their peers of the same age group and like backgrounds. A profile of SNPs can be developed that characterizes common factors associated with the phenotypic changes of aging skin (defined the SNP genotypic pattern that puts an individual at a greater risk of accelerate aging from increased oxidative stress from environmental agents). This allows for a treatment plan, which would have greater anti-aging benefits.

TGF-B is a major cytokine for cell signaling and inhibits the growth of epidermal keratinocytes and stimulates the growth of thermal fibroblasts. It also induces synthesis and secretion of the major collagen elastin and inhibits the expression of MMP 1 and MMP 3. There are multiple TGF-B's, TGF-B 1, TBR I, TBR II, many of which are down regulated in aging skin cells. TGF-B is also activity altered in aging skin by binding with Decerin and when this combines with collagen affects the tinsel strength of skin as well as controlling the rate of collagen fiber formation. c Jun MRNA is doubled in activity and age human skin compared to young skin but c-fos was unchanged. MMP 2 is not regulated through AP 1. ERK activity is reduced in aging skin, but JNK activity is increased 3-4 times in aging skin. Environmental insults-damage can vary anatomically over a person's body. These methods allow for rejuvenating human skin including the steps of simultaneously preventing collagen degradation while also stimulating the formation of new collagen in aging human skin.

Increased MMP's result in reduced levels of ERK, cyclin D2 and type I and III pro collagen. This is part of the core genotype, phenotype stimulating a number of keratinocytes as well as decreasing c-gen activity and increasing ERK activity.

A system of sunscreens, topical oil and antioxidants, topical oil and photomodulated ECM stimulation and MMP and MMP inhibition and various combinations and mixtures of the above. Inhibiting c-gen formation also inhibits formation AP-I and thus diminishes MMP's, inducing the proliferation of keratinocytes and fibroblasts.

Modulation of Mitochondrial Activity

Mitochondria and ATP production mechanisms (e.g. cytochrome expression) can be modulated by electromagnetic radiation. LED light activates cell surface receptors via redox mediated in activation or a receptor type protein tyrosine phosphatase (RTPT). SAP (stress activated pathways) verses mitogen activated pathways compare and contrast SAP increase MMP and decreases pro collagen 1 and 2 if c Jun goes up. Primarily has to do with the ECM production whereas the MAP pathways activate ERK induced cyclins and promote cell growth so that PSAT's tend to increase or decrease protein production whereas the MAPS increase or decrease cell growth. Ras/MAP/AP-1 pathway plays a key role in response to wounding. FGFR1 contains sites in the promoter region and IL1 antagonist promoter. Antioxidant compounds also have anti-erythema sunscreen effect although they may not inhibit the increased MMP after UV exposure, lycopene is one of these. LED photomodulation can also be used to diminish sunburn activity and MMP levels were maxed about 24 hours later. Use a solar simulator to cause a one MED minimal erythema dose on the arm in two places on volunteers and treat one a couple times a day with the GW device and to reduce redness with the chromometer. Biopsy will show what happens when you treat them with GW after UV. Inhibiting cytocrome P-450 breakdown of retinoids increases retinoid strength concentration.

While not wishing to be constrained to a particular theory of operation, the invention includes the surprising discovery that multiple receptor-mediated pathways may be photomodulated in human or mammalian skin that lead to an expression of the genotype associated with a younger or more youthful or less aged skin both in appearance and structurally and functionally.

Reference to infrared-a radiation induced MMP 1. Infrared is capable of producing MMP 1 by way of up regulation or activation of MAPK signaling pathway that is the activation of ERK ½ that the promoter region of the MMP 1 gene was activated by IRA without the production of heat, but that TIMP 1 was not increased. MMP-8 or elastase is increased with inflammatory reaction, which also involves AP I. And when NF-KB is increased it activates more of IL-1 and TNFa that discontinues the presence of continued inflammation.

Fibroblasts sensor matrix surround them and when in contact with a matrix they tend to be less active produce little collagen, but when the presence of collagen breaks down products such as gelatin, they tend to produce more collagen if the inflammation persists. The collagen not only proliferates, but produces less scarring.

Topical compounds that inhibit cytokines are indirect MMP inhibitors because if they block the pathway the signals MMP the essentially block this. The same is true for MMP regulation. Regarding nutraceuticals, Vitamin C can be topically applied to assemble stable collagen molecules. Collagen I and collagen III can be stimulated by topical of Vitamin C, whereas elastin, Fibrilin ½ are not affected nor is MMP 1, 2, and 9 affected. TIMP was increased, TIMP 2 was unchanged.

Modulation for Wound Healing and Therapy

Proteolytic degradation of ECM is an essential feature of repair and remodeling during continuous wound healing. Wound repair consists of narcotic or damaged tissue, cell and/or tissue migration, angiogenisis, remodeling of newly synthesized ECM, and cell growth factor regulations. During wound repair MMP 1 and MMP 3 increase as well as MMP 2 and 9. MMP 13, in particular, for chronic wounds, but also acute. TIMP is also altered. MMP 1, 3, 9 are increased with UVB; increased elastin and fibrilian verscian; result in the formation of non functional elastin fibers and reduce skin elasticity and aging or photoaged skin. Collagen I is reduced, and UVA shows increased expression of MMP 1, 2, 3.

Disease states-systemic sclaraderma skin fibroblasts produced less MMP 1 and MMP 3 and more TIMP 1 compared to normal. Skin cancers BCC produce more MMP 1, 2, 9 and 11. More signs of photoaging, bruising, skin hypopigmented areas, fibrosis. Methods and inventions for preventing the photoaging or chronological or environmental aging of unaged skin include retinoids that retard the effects of photoaging topical antioxidants to reduce presence of ROS in the skin. Environmental stresses include oxidants, heat, UV light. Thus, LED phototherapy is both an ECM protein/collagen stimulator, and an MMP inhibitor. Dose dependent UVB induction of AP 1 and NF-KB, these induced MMP 2 and MMP 9. The formation of collagen bundles is responsible for the strength, resiliency and elasticity of the skin.

In one embodiment of the invention single or multiple light sources may be used, to produce either a single dominant emissive wavelength, i.e., a narrowband multichromatic radiation, or multiple wavelengths (either monochromatic, narrowband multichromatic, wideband multichromatic, or combinations thereof). The single or multiple combinations may be applied either simultaneously or sequentially.

For example a device emitting narrowband, multichromatic electromagnetic radiation with a dominant emissive wavelength of about 590 nm (+/− about 10 nm) and also some light in the 850 nm range and, optionally, a small amount in the 1060 nm range. It has been discovered that the combination of the visible 590 and the infrared 850 nm is bioactive. A special IR filter may also be added to reduce the IR component of the radiation that the target skin or tissue is exposed to, as this is believed to unsymmetrically dampen the shape of the IR/850 curve. Treatment examples of such a device are shown in the attached drawing figures and illustrate that at 850 nm, there is believed to be a 'dose dependent' effect on fibroblasts. Further, at a power level of about 1 mW/cm$^2$, photomodulation occurs for anti aging phenotype effect (those skilled in the art will recognize that power meters cannot measure this precisely, so there may be some variation/error in meter methods). Generally, where a treatment that does not cause thermal injury is desired, an energy fluence of less than about 4 J/cm$^2$ is preferable.

The ratio of yellow light to IR radiation in the radiation used for treatment has been found to have an effect on the overall performance of the present system. Relative amounts of each type of radiation are believed to be important, more so than the actual radiation level (provided that ablation does not occur). At about 4 mW/cm$^2$ for 590 nm and about 1 mW/cm$^2$ for the 850 nm (i.e., a 4:1 ratio of yellow to IR) has been found to produce good results. Mother factor to consider is the shape of the amplitude vs. wavelength curve for the IR component of the system.

The 'code' refers to the pulse scheme for various treatment regimen. This includes various factors such as pulse length, interpulse delay, and pulse repetition. For example a treatment may comprise a pulse code of 250 msec "on" time, 100 msec "off" time (or dark period), and 100 pulses. This produces a total energy fluence, in J/cm2, of 25 seconds times the power output level of the emitters. This permits a comparison of pulsed versus continuous wave treatment (the "code" for continuous wave treatment would be 1 pulse, an "on" time of whatever the treatment length is chosen to be, and an "off" time of 0 sec.) Examples showing various codes, ratios, and power levels and the resulting effect on the photoaging effect on certain genes, and other data, are shown in the attached data tables and drawing figures.

The present invention is also related to a method and apparatus for treating sunburn and other sun-related photoeffects on human or mammalian skin. One approach is to use Retin A for prior to sun exposure and research is being conducted using vitamins C, E, and other antioxidants topically. Another approach being tried is the use of the antioxidant Lycopene, administered orally, to quench some of inflammation from sunburn. The present invention shows great improvement of such treatment methods, however.

One may think of wrinkles, sun damage, and other sun-related photo effects as 'solar scars'. They are cumulative injuries that result from repeated or long-term exposure to the sun. The human body employs and imperfect wound repair mechanism, thus the solar simulator of the present invention is, in some ways, a model for other wound healings. The present invention employs a treatment that simulates sunlight broken down into its component parts. The UVA 1 portion is used in some embodiments, but there is UVB and combinations of UVA and UVR that are more oncogenic. For example, UV, and in particular UVA 1, causes skin sagging and photo-aging, changes to the dermal matrix and structural proteins, and upregulates MMPs. UV radiation also causes the upregulation of inflammatory pathways such as IL1, IL6 and NFkB. These pathways are known to affect aging and other sun-related skin disorders and environmental damage, such as smoking, pollution, drugs, diseases, thermal injuries, other wounds.

The present invention is believed to inhibit or reverse the effects of photoaging and other skin disorders by reversing the direction of gene up/down regulation from the unfavorable and destructive directions caused by the effects of the solar simulator UVA1 for things like collagen, MMP1, cJun which is important related to MMP1, IL/interleukins in inflammatory pathway, and cytochromes. The attached examples describe the use of the present system for illustrative treatments.

The systems and methods of the present invention may be used in combination with various wound dressings like bandage strips modified to have a transparent covering, so that the desired spectra of photomodulation by LED or other light is transmitted to the wounded area of the skin or target tissue. One embodiment includes 'trap door' to permit the periodic inhibition of light transmission. The opening or translucent/transparent portion of the bandage may comprise an IR filter, as well. In instances where it is undesirable to include an opening as part of the bandage or wound dressing, the size of LED's and other light sources makes it possible to include a light source within the bandage. Such a source could be powered from a small battery and include means for having the light source automatically or manually apply treatment at regular intervals and according to a variety of preset codes (for example, a dressed chemical burn may require a different code than a cut or electrical burn). As well, various topical compositions for enhancing the penetration of the light through the skin or target tissue can be included in the dressing or bandage or applied to the skin or target tissue prior to covering the affected skin with the bandage or dressing.

A light source within the bandage may also be coded to 'release' or to 'activate' substances or delivery vehicles for substances so that oxygen, antibacterial, antiviral, anti fungal, etc., or other agents released. Combinations of such compositions may be used as well.

Another application would allow for the treatment of blood outside of the body (extracorporeally, in a phoresis device for example). The blood may be run through banks of arrays of LED, or other light or EMR, and then photomodulated either directly or by an agent that was photoactivatable, or both, to stimulate the immune system, treat disease, etc.

The present system and method may also be used for retinal and other eye treatments, alone or along with antioxidant eyedrop-type medications, bioengineered peptides, and growth factors. Antioxidant eyedrops include, but are not limited to glutathione, vitamin C, vitamin E, catalase, ubiquinone, idebenone, etc.

Other applications of the present invention include nerve regeneration, hormone manipulation (thyroid disease is common and is particularly contemplated due to the proximity of the thyroid to the skin). As well, photomodulating adipocytes for fat reduction, cellulite, etc. may be accomplished using light sources in the range of about 850-950 nm and 1000-1100 nm.

The following examples illustrate embodiments of the invention, but should not be viewed as limiting the scope of the invention.

EXAMPLES

Below are tables of data and examples that further illustrate the various embodiments of the invention, as well as lists of gene products which can be regulated by methods of the invention. In the below section, the results of two experiments which illustrate the embodiments are shown.

Examples

A. MGW49 Experiment #2

A healthy female volunteer with photoaged skin, age 50 years old, with skin type III participated in the study. The treatments were twice weekly for a total of 8 treatments. Skin biopsies were taken pre and 4 months post final treatment 590/810 nm LED Panel(ZZ)+IR filter, 250 ms on/100 ms off/100 pulses.

TABLE 1

| WGW49 IL-6%    | Tissue | Stained |
|----------------|--------|---------|
| Pre            | 30%    | −17%    |
| Post (4 month) | 13%    |         |

TABLE 2

| WGW49 Coll 1% | Tissue | Stained |
|---------------|--------|---------|
| Pre           | 16%    |         |
| Post          | 25%    | 9       |

TABLE 3

| WGW49 MMPI % | Tissue | Stained |
|--------------|--------|---------|
| Pre          | 37%    | −13%    |
| Post         | 24%    |         |

TABLE 4

| WGW49 MMP3% | Tissue | Stained |
|-------------|--------|---------|
| Pre         | 11%    | −8%     |
| Post        | 3%     |         |

TABLE 5

| WGW49 MMP9% | Tissue | Stained |
|-------------|--------|---------|
| Pre         | 11%    | −5%     |
| Post        | 6%     |         |

TABLE 6

| WGW49 MMP2% | Tissue | Stained |
|---|---|---|
| Pre | 10% | −5% |
| Post | 5% | |

TABLE 7

| WGW49 c-Fos % | Tissue | Stained |
|---|---|---|
| Pre | 12% | −6% |
| Post | 6% | |

TABLE 8

| WGW49 c-Jun % | Tissue | Stained |
|---|---|---|
| Pre | 35% | −17% |
| Post | 18% | |

TABLE 9

| WGW49 ERKI % | Tissue | Stained |
|---|---|---|
| Pre | 26% | −24% |
| Post | 2% | |

TABLE 10

| WGW49 ERK2% | Tissue | Stained |
|---|---|---|
| Pre | 13% | −11% |
| Post | 2% | |

TABLE 11

| WGW49 TIMP1% | Tissue | Stained |
|---|---|---|
| Pre | 15% | −4% |
| Post | 11% | |

TABLE 12

| WGW49 EGFr % | Tissue | Stained |
|---|---|---|
| Pre | 9% | −2% |
| Post | 7% | |

B. Solar Simulator

The solar simulator has a 1000-watt xenon arc lamp equipped with a water filter and a UV-reflecting dichroic mirror (280 nm-400 nm). A Schott WG-360 filter is used to simulate UVA1 radiation. An I-Line filter centered at 365 nm is added to remove residual visible and infrared radiation, and a Hoya UV34 filter is used to filter out any remaining UVB and UVC radiation.

A photoresist radiometer (International Light Inc., Newburyport, Mass.) is used to measure total irradiance. All Results from exposure to 590/810 nm LED(ZZ) or (DD) 250 ms on/100 ms off/100 pulses@3.6 mW/cm$^2$ 590/810 nm LED(DD) 24 hr Microarray Genes Aging Related:

TABLE 13

| Ratio | Gene | Title |
|---|---|---|
| 2.1 | HSPB1 | heat shock 27 kD protein 1 |
| 1.6 | HSPB2 | heat shock 27 kD protein 2 |
| −2.0 | SAA1 | serum amyloid Al |
| −1.1 | GADD45A | growth arrest and DNA-damage-inducible, alpha |
| 1.5 | RAC1 | ras-related C3 botulinum toxin substrate 1 (rho family, small GTP binding protein Racl) |
| −1.1 | RAC1 | ras-related C3 botulinum toxin substrate 1 (rho family, small GTP binding protein Racl) |
| −1.1 | DCTN1 | dynactin 1 (p150, Glued (*Drosophila*) homolog) |
| −1.4 | CKMT2 | creatine kinase, mitochondrial 2 (sarcomeric) |
| −1.1 | LONP | Lon protease-like protein |
| 1.1 | | ESTs, Highly similar to ALPHA-AMYLASE PANCREATIC PRECURSOR [*H. Sapiens*] |
| 1.5 | | ESTs, Highly similar to ALPHA-AMYLASE PANCREATIC PRECURSOR [*H. sapiens*] |
| −1.4 | GFER | growth factor, erv1 (*S. cerevisiae*)-like (augmenter of liver regeneration) |
| −1.3 | | ESTs, Highly similar to ATP SYNTHASE ALPHA CHAIN, MITOCHONDRIAL PRECURSOR [*H. sapiens*] |
| 1.0 | UCHL1 | ubiquitin carboxyl-terminal esterase L1 (ubiquitin thiolesterase) |
| −1.1 | TST | thiosulfate sulfurtransferase (rhodanese) |
| 1.3 | TST | thiosulfate sulfurtransferase (rhodanese) |
| 1.3 | TST | thiosulfate sulfurtransferase (rhodanese) |
| 1.3 | TST | thiosulfate sulfurtransferase (rhodanese) |
| 1.2 | NDN | necdin (mouse) homolog |
| 1.9 | S100A10 | S100 calcium-binding protein A10 (annexin II ligand, calpactin I, light polypeptide (p11)) |
| 1.8 | S100A10 | S100 calcium-binding protein Al 0 (annexin II ligand, calpactin I, light polypeptide (p11)) |
| 1.5 | S100A10 | S100 calcium-binding protein Al 0 (annexin II ligand, calpactin I, light polypeptide (p11)) |
| 1.2 | CALM3 | calmodulin 3 (phosphorylase kinase, delta) |
| 1.2 | CAMK1 | calcium/calmodulin-dependent protein kinase I |
| −1.4 | SCD | stearoyl-CoA desaturase (delta-9-desaturase) |
| 1.0 | TKT | transketolase (Wernicke-Korsakoff syndrome) |
| −1.3 | ALDOB | aldolase B, fructose-bisphosphate |
| 1.1 | ALDOA | aldolase A, fructose-bisphosphate |
| −1.3 | ALDOC | aldolase C, fructose-bisphosphate |
| −1.7 | ALDOB | aldolase B, fructose-bisphosphate |
| −1.7 | PPARG | peroxisome proliferative activated receptor, gamma |
| −1.4 | PPARD | peroxisome proliferative activated receptor, delta |
| −1.7 | FBP1 | fructose-bisphosphatase 1 |
| 1.1 | | EST, Highly similar to CARBONIC ANHYDRASE IV PRECURSOR [*H. sapiens*] |
| −1.1 | PKLR | pyruvate kinase, liver and RBC |
| 1.3 | PSME2 | proteasome (prosome, macropain) activator subunit 2 (PA28 beta) |
| −1.1 | PSME3 | proteasome (prosome, macropain) activator subunit 3 (PA28 gamma; Ki) |
| 1.6 | USA-CYP | cyclophilin |
| 1.0 | SSR1 | signal sequence receptor, alpha (translocon-associated protein alpha) |
| −1.4 | CYP3A3 | cytochrome P450, subfamily IIIA (niphedipine oxidase), polypeptide 3 |
| 1.0 | CYP3A3 | cytochrome P450, subfamily IIIA (niphedipine oxidase), polypeptide 3 |
| −1.3 | CYP3A3 | cytochrome P450, subfamily IIIA (niphedipine oxidase), polypeptide 3 |
| 1.0 | CYP3A7 | cytochrome P450, subfamily IIIA, polypeptide 7 |
| 1.3 | CYP3A7 | cytochrome P450, subfamily IIIA, polypeptide 7 |
| 1.1 | CYP3A7 | cytochrome P450, subfamily IIIA, polypeptide 7 |
| 1.2 | CYP3A7 | cytochrome P450, subfamily IIIA, polypeptide 7 |
| 1.4 | CYP3A7 | cytochrome P450, subfamily IIIA, polypeptide 7 |
| −1.1 | CYP3A7 | cytochrome P450, subfamily IIIA, polypeptide 7 |
| −1.3 | | Human thymidylate kinase (CDC8) mRNA, complete cds |

TABLE 13-continued

| Ratio | Gene | Title |
|---|---|---|
| 1.4 | CYP1B1 | cytochrome P450, subfamily I (dioxin-inducible), polypeptide 1 (glaucoma 3, primary infantile) |
| 1.0 | CYP1B1 | cytochrome P450, subfamily I (dioxin-inducible), polypeptide 1 (glaucoma 3, primary infantile) |
| 1.6 | CYP1B1 | cytochrome P450, subfamily I (dioxin-inducible), polypeptide 1 (glaucoma 3, primary infantile) |
| -1.1 | THRA | thyroid hormone receptor, alpha (avian erythroblastic leukemia viral (v-erb-a) oncogene homolog) |

590/810 nm LED(ZZ) 24 hr Microarray Genes Aging Related:

TABLE 14

| Ratio | Gene | Gene Title |
|---|---|---|
| 1.5 | HSPB1 | heat shock 27 kD protein 1 |
| 1.0 | HSPB2 | heat shock 27 kD protein 2 |
| -1.7 | SAA1 | serum amyloid A1 |
| 1.0 | GADD45A | growth arrest and DNA-damage-inducible, alpha |
| 1.1 | RAC1 | ras-related C3 botulinum toxin substrate 1 (rho family, small GTP binding protein Rac1) |
| 1.2 | RAC1 | ras-related C3 botulinum toxin substrate 1 (rho family, small GTP binding protein Rac1) |
| -1.1 | DCTN1 | dynactin 1 (p150, Glued (*Drosophila*) homolog) |
| -1.1 | CKMT2 | creatine kinase, mitochondrial 2 (sarcomeric) |
| -1.4 | LONP | Lon protease-like protein |
| 1.4 | | ESTs, Highly similar to ALPHA-AMYLASE PANCREATIC PRECURSOR [*H. sapiens*] |
| 1.0 | | ESTs, Highly similar to ALPHA-AMYLASE PANCREATIC PRECURSOR [*H. sapiens*] |
| 1.1 | LONP | GFER growth factor, erv1 (*S. cerevisiae*)-like (augmenter of liver regeneration) |
| -1.1 | | ESTs, Highly similar to ATP SYNTHASE ALPHA CHAIN, MITOCHONDRIAL PRECURSOR [*H. sapiens*] |
| 1.1 | UCHL1 | ubiquitin carboxyl-terminal esterase L1 (ubiquitin thiolesterase) |
| -1.3 | TST | thiosulfate sulfurtransferase (rhodanese) |
| 1.3 | TST | thiosulfate sulfurtransferase (rhodanese) |
| -1.3 | TST | thiosulfate sulfurtransferase (rhodanese) |
| -1.3 | TST | thiosulfate sulfurtransferase (rhodanese) |
| -1.1 | NDN | necdin (mouse) homolog |
| 1.5 | S100A10 | S100 calcium-binding protein A10 (annexin II ligand, calpactin I, light polypeptide (p11)) |
| 1.6 | S100A10 | S100 calcium-binding protein A10 (annexin II ligand, calpactin I, light polypeptide (p11)) |
| 1.2 | S100A10 | S100 calcium-binding protein A10 (annexin II ligand, calpactin I, light polypeptide (p11)) |
| -1.1 | CALM3 | calmodulin 3 (phosphorylase kinase, delta) |
| -1.3 | CAMK1 | calcium/calmodulin-dependent protein kinase I |
| -1.1 | SCD | stearoyl-CoA desaturase (delta-9-desaturase) |
| -1.1 | TKT | transketolase (Wernicke-Korsakoff syndrome) |
| -1.1 | ALDOB | aldolase B, fructose-bisphosphate |
| 1.7 | ALDOA | aldolase A, fructose-bisphosphate |
| -1.1 | ALDOC | aldolase C, fructose-bisphosphate |
| 1.0 | ALDOB | aldolase B, fructose-bisphosphate |
| -1.3 | PPARG | peroxisome proliferative activated receptor, gamma |
| -1.1 | PPARD | peroxisome proliferative activated receptor, delta |
| -1.4 | FBP1 | fructose-bisphosphatase 1 |
| -1.3 | | EST, Highly similar to CARBONIC ANHYDRASE IV PRECURSOR [*H. sapiens*] |
| 1.0 | PKLR | pyruvate kinase, liver and RBC |
| 1.1 | PSME2 | proteasome (prosome, macropain) activator subunit 2 (PA28 beta) |
| 1.1 | PSME3 | proteasome (prosome, macropain) activator subunit 3 (PA28 gamma; Ki) |
| 1.0 | USA-CYP | cyclophilin |
| 1.1 | SSR1 | signal sequence receptor, alpha (translocon-associated protein alpha) |
| -1.3 | CYP3A3 | cytochrome P450, subfamily IIIA (niphedipine oxidase), polypeptide 3 |
| -1.1 | CYP3A3 | cytochrome P450, subfamily IIIA (niphedipine oxidase), polypeptide 3 |
| 1.2 | CYP3A3 | cytochrome P450, subfamily IIIA (niphedipine oxidase), polypeptide 3 |
| 1.0 | CYP3A7 | cytochrome P450, subfamily IIIA, polypeptide 7 |
| 1.1 | CYP3A7 | cytochrome P450, subfamily IIIA, polypeptide 7 |
| -1.1 | CYP3A7 | cytochrome P450, subfamily IIIA, polypeptide 7 |
| 1.2 | CYP3A7 | cytochrome P450, subfamily IIIA, polypeptide 7 |
| 1.3 | CYP3A7 | cytochrome P450, subfamily IIIA, polypeptide 7 |
| 1.0 | CYP3A7 | cytochrome P450, subfamily IIIA, polypeptide 7 |
| 1.0 | | Human thymidylate kinase (CDC8) mRNA, complete cds |
| 1.1 | CYP1B1 | cytochrome P450, subfamily I (dioxin-inducible), polypeptide 1 (glaucoma 3, primary infantile) |
| -1.3 | CYP1B1 | cytochrome P450, subfamily I (dioxin-inducible), polypeptide 1 (glaucoma 3, primary infantile) |
| 1.5 | CYP1B1 | cytochrome P450, subfamily I (dioxin-inducible), polypeptide 1 (glaucoma 3, primary infantile) |
| 1.0 | THRA | thyroid hormone receptor, alpha (avian erythroblastic leukemia viral (v-erb-a) oncogene homolog) |

All Results from exposure to 590/810 nm LED(ZZ) or (DD) 250 ms on/100 ms off/100 pulses@3.6 mW/cm$^2$:

Glycolysis Pathway Genes 590/810 nm LED(DD)@24 hrs:

TABLE 15

| Ratio | Expression | Gene | Title |
|---|---|---|---|
| 2.182361 | 2.18 | TPI1 | triosephosphate isomerase 1 |
| 1.552958 | 1.55 | PGAM1 | phosphoglycerate mutase 1 (brain) |
| 1.448117 | 1.45 | PDHA1 | pyruvate dehydrogenase (lipoamide) alpha 1 |
| 1.424174 | 1.42 | PGK1 | phosphoglycerate kinase 1 |
| 1.421996 | 1.42 | OLD | dihydrolipoamide dehydrogenase (E3 component of pyruvate dehydrogenase complex, 2-oxo-glutarate complex, branched chain keto acid dehydrogenase complex) |
| 1.371788 | 1.37 | PCK2 | phosphoenolpyruvate carboxykinase 2 (mitochondria°) |
| 1.262148 | 1.26 | SLC2A4 | solute carrier family 2 (facilitated glucose transporter), member 4 |
| 1.182199 | 1.18 | G6PD | glucose-8-phosphate dehydrogenase |
| 1.179759 | 1.18 | UGP2 | UDP-glucose pyrophosphorylase 2 |
| 1.176488 | 1.18 | PC | pyruvate carboxylase |
| 1.171328 | 1.17 | PFKP | phosphofructokinase, platelet |
| 1.127554 | 1.13 | ALDOA | aldolase A, fructose-bisphosphate |
| 1.11909 | 1.12 | GRP58 | glucose regulated protein. 58 kD |
| 1.113097 | 1.11 | UGCG | UDP-glucose ceramide glucosyl-transferase |
| 0.975606 | -1.03 | PGAM2 | phosphoglycerate mutase 2 (muscle) |
| 0.968111 | -1.03 | SLC2A1 | solute carrier family 2 (facilitated glucose transporter), member 1 |
| 0.966833 | -1.03 | GPD1 | glycerol-3-phosphate dehydrogenase 1 (soluble) |
| 0.935412 | -1.07 | KHK | ketohexokinase (fructokinase) |
| 0.929888 | -1.08 | G8PC | glucose-6-phosphatase, catalytic (glycogen storage disease type I, von Gierke disease) |
| 0.927444 | -1.08 | | Human glucose transporter pseudogene |
| 0.923213 | -1.08 | GPD2 | glycerol-3-phosphate dehydrogenase 2 (mitochondria( ) |
| 0.90049 | -1.11 | PFKM | phosphofructokinase, muscle |
| 0.89909 | -1.11 | PKLR | pyruvate kinase, liver and RBC |
| 0.878268 | -1.14 | PDK2 | pyruvate dehydrogenase kinase, isoenzyme 2 |
| 0.851829 | -1.17 | PCK1 | phosphoenolpyruvate carboxykinase 1 (soluble) |
| 0.848316 | -1.18 | ALDOC | aldolase C, fructose-bisphosphate |
| 0.825748 | -1.21 | HK1 | hexokinase 1 |

TABLE 15-continued

| Ratio | Expression | Gene | Title |
|---|---|---|---|
| 0.810006 | −1.23 | SLC2A5 | solute carrier family 2 (facilitated glucose transporter), member 5 |
| 0.800583 | −1.25 | PFKL | phosphofructokinase, liver |
| 0.785187 | −1.27 | G6PD | glucose-6-phosphate dehydrogenase |
| 0.774527 | −1.29 | G6PT1 | glucose-6-phosphatase, transport (glucose-6-phosphate) protein 1 |
| 0.763362 | −1.31 | ALDOB | aldolase B, fructose-bisphosphate |
| 0.741454 | −1.35 | BPGM | 2.3-bisphosphoglycerate mutase |
| 0.741454 | −1.35 | BPGM | 2,3-bisphosphoglycerate mutase |
| 0.729919 | −1.37 | GFPT1 | glutamine-fructose-6-phosphate transaminase 1 |
| 0.69455 | −1.44 | AGXT | alanine-glyoxylate aminotransferase (oxalosis I; hyperoxaluria I; glycolicaciduria; serine-pyruvate aminotransferase) |
| 0.65802 | −1.52 | SLC2A2 | solute carrier family 2 (facilitated glucose transporter), member 2 |
| 0.854048 | −1.53 | PDK4 | pyruvate dehydrogenase kinase, isoenzyme 4 |
| 0.646769 | −1.55 | | *H. spaiens* 3' mRNA for neurone-specific enolase (EC 4.2.1.11) |
| 0.621536 | −1.61 | FBP1 | fructose-bisphosphatase 1 |
| 0.592292 | −1.69 | ALDOB | aldolase B, fructose-bisphosphate |

Glycolysis Pathway Genes 590/810 nm LED(DD)@4 hrs:

TABLE 16

| Ratio | Expression | Gene | Title |
|---|---|---|---|
| 2.276179 | 2.28 | GPD1 | glycerol-3-phosphate dehydrogenase 1 (soluble) |
| 1.750555 | 1.75 | PFKL | phosphofructokinase, liver |
| 1.698153 | 1.70 | ALDOB | aldolase B, fructose-bisphosphate |
| 1.690101 | 1.69 | PFKM | phosphofructokinase, muscle |
| 1.590717 | 1.59 | PFKP | phosphofructokinase, platelet |
| 1.418758 | 1.42 | FBP1 | fructose-bisphosphatase 1 |
| 1.219502 | 1.22 | G6PC | glucose-6-phosphatase, catalytic (glycogen storage disease type 1, von Gierke disease) |
| 1.19087 | 1.19 | UGCG | UDP-glucose ceramide glucosyltransferase |
| 1.189572 | 1.19 | PCK1 | phosphoenolpyruvate carboxyldnase 1 (soluble) |
| 1.188725 | 1.19 | HK1 | hexokinase 1 |
| 1.167392 | 1.17 | ALDOC | aldolase C, fructose-bisphosphate |
| 1.117239 | 1.12 | ALDOA | aldolase A, fructose-bisphosphate |
| 1.09276 | 1.09 | SLC2A2 | solute carrier family 2 (facilitated glucose transporter), member 2 |
| 1.081626 | 1.08 | SLC2A4 | solute carrier family 2 (facilitated glucose transporter), member 4 |
| 1.03385 | 1.03 | PKLR | pyruvate kinase, liver and RBC |
| 1.024675 | 1.02 | UGP2 | UDP-glucose pyrophosphorytase 2 |
| 1.010242 | 1.01 | G6PD | glucose-6-phosphate dehydrogenase |
| 1.001788 | 1.00 | | *H. spaiens* 3' mRNA for neurone-specific enolase (EC 4.2.1.11) |
| 0.999114 | −1.00 | PDK2 | pyruvate dehydrogenase kinase, isoenzyme 2 |
| 0.97332- | 1.03 | TPI1 | triosephosphate isomerase 1 |
| 0.97298 | −1.03 | | PDK4 pyruvate dehydrogenase kinase, isoenzyme 4 |
| 0.97083 | −1.03 | PDHA1 | pyruvate dehydrogenase (lipoamide) alpha 1 |
| 0.9635- | −1.04 | GFPT1 | glutamine-fructose-6-phosphate transaminase 1 |
| 0.934905 | −1.07 | KHK | ketohexokinase (fructokinase) |
| 0.922737 | −1.08 | GPD2 | glycerol-3-phosphate dehydrogenase 2 (mitochondrial) |
| 0.918168 | −1.09 | PCK2 | phosphoenolpyruvate carboxykinase 2 (mitochondrial) |

TABLE 16-continued

| Ratio | Expression | Gene | Title |
|---|---|---|---|
| 0.913855 | −1.09 | | Human glucose transporter pseudogene |
| 0.897852 | −1.11 | G6PD | glucose-6-phosphate dehydrogenase |
| 0.896324 | −1.12 | G6PT1 | glucose-6-phosphatase, transport (glucose-13-phosphate) protein 1 |
| 0.87878 | −1.14 | PC | pyruvate carboxylase |
| 0.874379 | −1.14 | BPGM | 2,3-bisphosphoglycerate mutase |
| 0.864752 | −1.16 | AGXT | alanine-glyoxylate aminotransferase (oxalosis I; hyperoxaluria I; glycolicaciduria; serine-pymvate aminotransferase) |
| 0.839583 | −1.19 | SLC2A1 | solute carrier family 2 (facilitated glucose transporter), member 1 |
| 0.831274 | −1.20 | SLC2A5 | solute carrier family 2 (facilitated glucose transporter), member 5 |
| 0.819752 | −1.22 | PGAM1 | phosphoglycerate mutase 1 (brain) |
| 0.819711 | −1.22 | PGK1 | phosphoglycerate kinase 1 |
| 0.748782 | −1.34 | ALDOB | aldolase B, fructose-bisphosphate |
| 0.722365 | −1.38 | PGAM2 | phosphoglycerate mutase 2 (muscle) |
| 0.570885 | −1.75 | GRP58 | glucose regulated protein, 58 kD |
| 0.385975 | −2.59 | DLD | dihydrolipoamide dehydrogenase (E3 component of pyruvate dehydrogenase complex, 2-oxo-glutarate complex, branched chain keto acid dehydrogenase complex) |

All Results from exposure to 590/810 nm LED(ZZ) or (DD) 250 ms on/100 ms off/100 pulse:

Interlukin 24 hr Microarray results in Human Fibroblasts 590/810 n LED(DD)

TABLE 17

| Ratio | Gene | Description |
|---|---|---|
| 1.0 | IL1RN | interleukin 1 receptor antagonist |
| −1.1 | IL1RN | interleukin 1 receptor antagonist |
| 1.0 | IL1RN | interleukin 1 receptor antagonist |
| 1.1 | IL1R2 | interleukin 1 receptor, type II |
| 1.2 | IL1R2 | interleukin 1 receptor, type II |
| −1.3 | IL1R2 | interleukin 1 receptor, type II |
| −1.1 | IL1B | interleukin 1, beta |
| −1.1 | IL1B | interleukin 1, beta |
| −2.5 | IL1B | interleukin 1, beta |
| −2.0 | IL1RL1 | interleukin 1 receptor-like 1 |
| −1.3 | IL1RAP | interleukin 1 receptor accessory protein |
| 1.0 | IL1RAP | interleukin 1 receptor accessory protein |
| −1.3 | IL1RAP | interleukin 1 receptor accessory protein |
| 1.5 | ILIA | interleukin 1, alpha |
| 1.0 | IL1A | interleukin 1, alpha |
| 1.1 | IL1A | interleukin 1, alpha |
| −2.0 | IL6 | interleukin 6 (interferon, beta 2) |
| 1.5 | IL6 | interleukin 6 (interferon, beta 2) |
| −1.7 | IL6 | interleukin 6 (interferon, beta 2) |

Interlukin 4 hr Microarray results in Human Fibroblasts 590/810n LED(DD)

TABLE 18

| Ratio | Gene | Description |
|---|---|---|
| −1.1 | IL1RN | interleukin 1 receptor antagonist |
| −1.4 | IL1RN | interleukin 1 receptor antagonist |
| −1.3 | IL1RN | interleukin 1 receptor antagonist |
| −1.1 | IL1R2 | interleukin 1 receptor, type II |
| 1.0 | IL1R2 | interleukin 1 receptor, type II |
| −1.1 | ILIR2 | interleukin 1 receptor, type II |
| 1.1 | IL1RL1 | interleukin 1 receptor-like 1 |
| 1.1 | IL1RAP | interleukin 1 receptor accessory protein |
| 1.0 | IL1RAP | interleukin 1 receptor accessory protein |
| −1.1 | IL1RAP | interleukin 1 receptor accessory protein |
| 1.0 | IL1A | interleukin 1, alpha |

TABLE 18-continued

| Ratio | Gene | Description |
|---|---|---|
| 1.0 | IL1A | interleukin 1, alpha |
| -1.1 | IL1A | interleukin 1, alpha |
| 1.8 | IL6 | interleukin 6 (interferon, beta 2) |
| 1.7 | IL6 | interleukin 6 (interferon, beta 2) |
| -1.1 | IL6 | interleukin 6 (interferon, beta 2) |

All Results from exposure to 590/810 nm LED(ZZ) or (DD) 250 ms on/100 ms off/100 pulses@3.6 mW/cm$^2$:

JJ=623 nm LED Array 250 ms on/100 ms off/100 pulses@3.6 mW/cm$^2$

Microarray Results for Keratinocyte Markers (on Human Fibroblast Samples) 24 hrs Post Exposure LEDs

TABLE 19

| 590/810 nm (DD) | 590/810 nm (ZZ) | 623 nm LED (JJ) | Gene | Title |
|---|---|---|---|---|
| 2.1 | 1.7 | -1.3 | | Human beta-1D integrin mRNA, cytoplasmic domain, partial cds |
| 1.6 | 1.4 | -1.3 | | Human beta-1D integrin mRNA, cytoplasmic domain, partial cds |
| 1.5 | 1.6 | -1.1 | | Human beta-1D integrin mRNA, cytoplasmic domain, partial cds |
| 1.3 | -1.1 | -1.4 | ICAM1 | intercellular adhesion molecule 1 (CD54), human rhinovirus receptor |
| 1.3 | 1.0 | -1.1 | ICAM1 | intercellular adhesion molecule 1 (CD54), human rhinovirus receptor |
| -1.1 | -1.3 | 1.2 | ICAM1 | intercellular adhesion molecule 1 (CD54), human rhinovirus receptor |
| 3.0 | 2.3 | -1.7 | KRT1 | keratin 1 (epidermolytic hyperkeratosis) |
| 1.9 | 1.1 | -3.3 | KRT1 | keratin 1 (epidermolytic hyperkeratosis) |
| 1.1 | 1.5 | 1.8 | KRT1 | keratin 1 (epidermolytic hyperkeratosis) |
| 2.2 | 1.5 | -1.4 | KRT10 | keratin 10 (epidermolytic hyperkeratosis; keratosis palmaris et plantaris) |
| 1.2 | -1.3 | -1.3 | KRT10 | keratin 10 (epidermolytic hyperkeratosis; keratosis palmaris et plantaris) |
| 1.3 | 1.0 | -1.3 | KRT10 | keratin 10 (epidermolytic hyperkeratosis; keratosis palmaris et plantaris) |
| 1.0 | -1.3 | 1.1 | IVL | Involucrin |
| -1.1 | -1.7 | 1.1 | IVL | Involucrin |
| -1.3 | -1.1 | 1.5 | IVL | Involucrin |
| 1.0 | -1.1 | -1.1 | M60502 | Profilaggrin - determined by alignment by Integriderm with gene M60502 |
| 1.1 | -1.1 | 1.3 | M60502 | Profilaggrin - determined by alignment by Integriderm with gene M60502 |
| 1.1 | 1.2 | 1.3 | M60502 | Profilaggrin - determined by alignment by Integriderm with gene M60502 |
| 1.0 | 1.1 | 1.0 | FGF7 | fibroblast growth factor 7 (keratinocyte growth factor) |
| -1.7 | -1.3 | 1.5 | PAI2 | plasminogen activator inhibitor, type II (arginine-serpin) |
| 1.2 | -1.1 | -1.1 | PA/1 | plasminogen activator inhibitor, type I |
| 1.5 | 1.0 | -1.1 | PA/1 | plasminogen activator inhibitor, type I |
| 1.4 | 1.1 | 1.0 | PA/1 | plasminogen activator inhibitor, type I |
| -1.4 | -1.3 | 1.4 | ITGB4 | integrin, beta 4 |
| 1.0 | -1.1 | 1.4 | ITGB4 | integrin, beta 4 |
| -1.7 | -1.1 | 1.6 | ITGB4 | integrin, beta 4 |

Microarray Results for Keratinocyte Markers (on Human Fibroblast Samples) 4 hrs Post Exposure LEDs

TABLE 20

| 590/810 nm (DD) | | |
|---|---|---|
| 1.0 | ITGB4 | integrin, beta 4 |
| -1.3 | ITGB4 | integrin, beta 4 |
| 1.0 | ITGB4 | integrin, beta 4 |
| -2.0 | | Human beta-1D integrin mRNA, cytoplasmic domain, partial cds |
| -2.5 | | Human beta-1D integrin mRNA, cytoplasmic domain, partial cds |
| -1.3 | | Human beta-1D integrin mRNA, cytoplasmic domain, partial cds |
| -1.3 | ICAM1 | intercellular adhesion molecule 1 (CD54), human rhinovirus receptor |
| -1.3 | ICAM1 | intercellular adhesion molecule 1 (CD54), human rhinovirus receptor |
| 1.0 | ICAM1 | Intercellular adhesion molecule 1 (CD54), human rhinovirus receptor |
| -1.7 | KRT1 | keratin 1 (epidermolytic hyperkeratosis) |
| -1.3 | KRT1 | keratin 1 (epidermolytic hyperkeratosis) |
| -1.3 | KRT1 | keratin 1 (epidermolytic hyperkeratosis) |

TABLE 20-continued

590/810 nm (DD)

| | | |
|---|---|---|
| −1.3 | KRT10 | keratin 10 (epidermolytic hyperkeratosis; keratosis palmaris et plantaris) |
| −1.4 | KRT10 | keratin 10 (epidermolytic hyperkeratosis; keratosis palmaris et plantaris) |
| 1.2 | KRT10 | keratin 10 (epidermolytic hyperkeratosis; keratosis palmaris et plantaris) |
| 1.1 | IVL | Involucrin |
| 1.1 | IVL | Involucrin |
| 1.2 | IVL | Involucrin |
| −1.7 | M60502 | Profilaggrin - determined by alignment by Integriderm with gene M60502 |
| −1.7 | M60502 | Profilaggrin - determined by alignment by Integriderm with gene M60502 |
| 1.1 | M60502 | Profilaggrin - determined by alignment by Integriderm with gene M60502 |
| −1.3 | FGF7 | fibroblast growth factor 7 (keratinocyte growth factor) |
| −1.3 | PAI2 | plasminogen activator inhibitor, type II (arginine-serpin) |
| −1.1 | PAI1 | plasminogen activator inhibitor, type I |
| −1.1 | PAI1 | plasminogen activator inhibitor, type I |
| 1.0 | PAI1 | plasminogen activator inhibitor, type I |

All Results from exposure to 590/810 nm LED(ZZ) or (DD)+IR Filter 250 ms on/100 ms off/100 pulses@3.6 mW/cm$^2$:

590/810 nm(DD)+IR Filter Panel 24 hr

TABLE 21

| Ratio | Expression | Gene | Title |
|---|---|---|---|
| 0.755466 | −1.32 | BNIP3 | BCL2/adenovirus EI B 19 kD-interacting protein 3 |
| 2.019761 | 2.02 | PRKDC | protein kinase, DNA-activated, catalytic polypeptide |

4 hr Human Fibroblast Expression post Exposure 590/810 nm(DD)

TABLE 22

| Ratio | Expression | Gene | Title |
|---|---|---|---|
| 1.049853 | 1.05 | BNIP3 | BCL2/adenovirus EI B 19 kD-interacting protein 3 |
| 0.949196 | −1.05 | PRKDC | protein kinase, DNA-activated, catalytic polypeptide |
| 0.71181 | −1.40 | BNIP3 | BCL2/adenovirus EIS 19 kD-interacting protein 3 |
| 1.268956 | 1.27 | BCL2A1 | BCL2-related protein Al |
| 0.678271 | −1.47 | BCL2L1 | BCL2-like 1 |
| 1.067873 | 1.07 | HSPA4 | heat shock 70 kD protein 4 |
| 0.587835 | −1.70 | SOD1 | superoxide dismutase 1, soluble (amyotrophic lateral sclerosis 1 (adult)) |
| 0.860347 | −1.16 | SOD1 | superoxide dismutase 1, soluble (amyotrophic lateral sclerosis 1 (adult)) |
| 0.522557 | −1.91 | SOD1 | superoxide dismutase 1, soluble (amyotrophic lateral sclerosis 1 (adult)) |
| 0.975844 | −1.02 | SOD2 | superoxide dismutase 2, mitochondrial |

All Results from exposure to 590/810 nm LED(ZZ) or (DD) 250 ms on/1100 ms off/100 pulses@3.6 mW/cm$^2$:

Interlukin 24 hr Microarray results in Human Fibroblasts 590/810 n LED(DD)

TABLE 23

| Ratio | Gene | Description |
|---|---|---|
| 1.0 | IL1RN | interleukin 1 receptor antagonist |
| −1.1 | ILIRN | interleukin 1 receptor antagonist |
| 1.0 | IL1RN | interleukin 1 receptor antagonist |
| 1.1 | IL1R2 | interleukin 1 receptor, type II |
| 1.2 | IL1R2 | interleukin 1 receptor, type II |
| −1.3 | 1L1R2 | interleukin 1 receptor, type II |
| −1.1 | IL1B | interleukin 1, beta |
| −1.1 | ILIB | interleukin 1, beta |
| −2.5 | 1L1B | interleukin 1, beta |
| −2.0 | IL1RL1 | interleukin 1 receptor-like 1 |
| −1.3 | IL1RAP | interleukin 1 receptor accessory protein |
| 1.0 | IL1RAP | interleukin 1 receptor accessory protein |
| −1.3 | IL1RAP | interleukin 1 receptor accessory protein |
| 1.5 | ILIA | interleukin 1, alpha |
| 1.0 | ILIA | interleukin 1, alpha |
| 1.1 | ILIA | interleukin 1, alpha |
| −2.0 | IL6 | interleukin 6 (interferon, beta 2) |
| 1.5 | IL6 | interleukin 6 (interferon, beta 2) |
| −1.7 | 1L6 | interleukin 6 (interferon, beta 2) |

Interleukin 4 hr Microarray results in Human Fibroblasts 590/810 n LED(DD)

TABLE 24

| Ratio | Gene | Description |
|---|---|---|
| −1.1 | ILIRN | interleukin 1 receptor antagonist |
| −1.4 | IL1RN | interleukin 1 receptor antagonist |
| −1.3 | IL1RN | interleukin 1 receptor antagonist |
| −1.1 | IL1R2 | interleukin 1 receptor, type II |
| 1.0 | 1L1R2 | interleukin 1 receptor, type II |
| −1.1 | IL1R2 | interleukin 1 receptor, type II |
| 1.1 | IL1RL1 | interleukin 1 receptor-like I |
| 1.1 | IL1RAP | interleukin 1 receptor accessory protein |
| 1.0 | IL1RAP | interleukin 1 receptor accessory protein |
| −1.1 | IL1RAP | interleukin 1 receptor accessory protein |
| 1.0 | IL1A | interleukin 1, alpha |
| 1.0 | IL1A | interleukin 1, alpha |
| −1.1 | IL1A | interleukin 1, alpha |
| 1.8 | IL6 | interleukin 6 (interferon, beta 2) |
| −1.7 | IL6 | interleukin 6 (interferon, beta 2) |
| −1.1 | IL6 | interleukin 6 (interferon, beta 2) |

All Results from exposure to 590/810 nm LED(ZZ) or (DD) 250 ms on/100 ms off/100 pulses@3.6 mW/cm$^2$:

24 hr Microarray
590/810 nm LED (DD)

TABLE 25

| Ratio | Gene | Description |
|---|---|---|
| 1.0 | TGFBI | transforming growth factor, beta 1 |
| −2.0 | TGFB3 | transforming growth factor, beta 3 |
| −1.1 | TGFB1/1 | transforming growth factor beta 1 induced transcript 1 |
| −1.7 | TGFA | transforming growth factor, alpha |

590/810 nm LED(ZZ)

TABLE 26

| Ratio | Gene | Description |
|---|---|---|
| −1.1 | TGFB1 | transforming growth factor, beta 1 |
| −2.0 | TGFB3 | transforming growth factor, beta 3 |
| −1.4 | TGFB1/1 | transforming growth factor beta 1 induced transcript 1 |
| −1.1 | TGFA | transforming growth factor, alpha |

623 nm LED(JJ)

TABLE 27

| Ratio | Gene | Description |
|---|---|---|
| 1.2 | TGFB1 | transforming growth factor, beta 1 |
| 2.0 | TGFB3 | transforming growth factor, beta 3 |
| −1.4 | TGFB1/1 | transforming growth factor beta 1 induced transcript 1 |
| 1.7 | TGFA | transforming growth factor, alpha |

4 hr Microarray
590/810 nm LED(DD)

TABLE 28

| Ratio | Gene | Description |
|---|---|---|
| −1.4 | TGFB1 | transforming growth factor, beta 1 |
| 1.1 | TGFB3 | transforming growth factor, beta 3 |
| −1.1 | TGFB1/1 | transforming growth factor beta 1 induced transcript 1 |
| 1 | TGFA | transforming growth factor, alpha |

All Results from exposure to 590/810 nm LED(ZZ) or (DD) 25 ms on/100 ms off/100 pulses@3.6 mW/cm$^2$
590/810 nm LED(DD) 24 hrs
Proliferation:
(stimulatory roles)

TABLE 29

| | | |
|---|---|---|
| −1.1 | CDK5 | cyclin-dependent kinase 5 |
| −1.4 | PDGFA | platelet-derived growth factor alpha polypeptide |
| 1.9 | BCRP1 | breakpoint cluster region protein, uterine leiomyoma, 1; barrier to autointegration factor |
| 1.1 | MAPK1 | mitogen-activated protein kinase 1 |
| −1.3 | MAPK9 | mitogen-activated protein kinase 9 |
| −1.9 | MAPK4 | mitogen-activated protein kinase 4 |
| 1.2 | MAPK14 | mitogen-activated protein kinase 14 |
| −1.3 | MAPK10 | mitogen-activated protein kinase 10 |
| 1 | MAPK6 | mitogen-activated protein kinase 6 |
| −1.1 | CCNE1 | cyclin E1 |
| 1.5 | CCNI | cyclin I |
| −1.2 | KNSL1 | kinesin-like 1 |

TABLE 30

| | | |
|---|---|---|
| −1.4 | SEPW1 | selenoprotein W, 1 |
| −1.5 | ATOX1 | ATX1 (antioxidant protein 1, yeast) homolog 1 |

Apoptosis and stress proteins:
(enhancing apoptosis and stress)

TABLE 31

| | | |
|---|---|---|
| −1.8 | CRADD | CASP2 and RIPK1 domain containing adaptor with death domain |
| −1.2 | HSPA9B | heat shock 70 kD protein 9B (mortalln-2) |
| 2.1 | HSPB1 | heat shock 27 kD protein 1 |
| 1.6 | HSPB2 | heat shock 27 kD protein 2 |
| 1.1 | HSPF2 | heat shock 40 kD protein 2 |
| 0 | CASP6 | caspase 6, apoptosis-related cysteine protease |

(Suppressing Apoptosis and Stress)

TABLE 32

| | | |
|---|---|---|
| −1.2 | SSI-1 | JAK binding protein |

Metabolism:

TABLE 33

(protein and amino acid)

| | | |
|---|---|---|
| 1.3 | CANK | calnexin |
| 1.2 | BCAT2 | branched chain aminotransferase 2, mitochondrial |
| 1.7 | PSMB3 | proteasome (prosome, macropain) subunit, beta type, 3 |
| 1.3 | PPIF | peptidylprolyl isomerase F (cyclophilin F) |
| 1.6 | USA-CYP | cyclophilin |
| 1.2 | PPIC | peptidyiprolyl isomerase C (cyclophilin C) |
| 1.4 | PPID | peptidylprolyl isomerase D (cyclophilin D) |
| −1.4 | | Human RNA polymerese II elongation factor ELL2, complete cds |
| 1.8 | CCT2 | chaperonin containing TCP1, subunit 2 (beta) |
| 1.1 | HDLBP | high density lipoprotein binding protein |

(sugar)

| | | |
|---|---|---|
| −1.5 | | H. sapaiens 3' mRNA for neurons-specific endue (EC 4.2.1.11) |
| −1.1 | ALDOA | aldolase A, fructose-bisphosphate |

(lipids)

| | | |
|---|---|---|
| 1.4 | APOC3 | apolipoprotein C-111 |

(energy metabolism and respiratory chain)

| | | |
|---|---|---|
| −1 | NDUFB4 | NADH dehydrogenase (ubiquinone) 1 beta subcomplex, 4 (15 kD, B15) |
| 1.2 | NDUFB7 | NADH dehydrogenase (ubiquinone) 1 beta subcomplex, 7 (18 kD, B18) |
| 1.6 | NDUFB1 | NADH dehydrogenase (ubiquinone) 1 beta subcomplex, 1 (7 kD, MNLL) |
| 1 | ETFA | electron-transfer-flavoprotein, alpha polypeptide (glutaric aciduria II) |
| −1.1 | ATP5D | ATP synthase, H+ transporting, mitochondrial F1 complex, delta subunit |
| 1.7 | ATP5O | ATP synthase, H+ transporting, mitochondrial F1 complex, O subunit (oligomycln sensitivity conferring protein) |
| 1.3 | ATP5G2 | ATP synthase, H+ transporting, mitochondrial F0 complex, subunit c (subunit 9), isoform 2 |
| 1.7 | ATP5F1 | ATP synthase, H+ transporting. mitochondrial F0 complex, subunit b, isoform 1 |
| 1.9 | ATP5C1 | ATP synthase, H+ transporting, mitochondrial F1 complex, gamma polypeptide 1 |

Ion Channel, transport proteins and membrane potential:

TABLE 34

| | | |
|---|---|---|
| 1.5 | TAP1 | transporter 1, ABC (ATP binding cassette) |
| −1.9 | ABC3 | ATP-binding cassette 3 |
| 1.8 | ABC5O | ATP-binding cassette 50 (TNF-alpha stimulated) |
| −1.5 | KCNJ13 | potassium inwardly-rectifying channel, subfamily J, member 13 |
| −1.1 | KCNK1 | potassium channel, subfamily K member 1 (TWIK-1) |
| −1.1 | KCNQ1 | potassium voltage-gated channel, KQT-like subfamily, member 1 |
| 1.1 | KCNAB1 | potassium voltage-gated channel, shaker-related subfamily, beta member 1, |
| −1 | KCNA1 | potassium voltage-gated channel, shaker-related subfamily, member 1 (pisodic ataxia with myokymia) |
| 1.2 | KCNB1 | potassium voltage-gated channel, Shab-related subfamily, member 1 |
| 1.8 | KCNMB1 | potassium large conductance calcium-activated channel, subfamily M, beta member 1 |
| −1.8 | KCNJ8 | potassium inwardly-rectifying channel, subfamily J, member 8 |

TABLE 34-continued

| | | |
|---|---|---|
| −1.1 | KCNN4 | potassium intermediate/small conductance calcium-activated channel, subfamily N, member 4 |
| −1.4 | KCNAB2 | potassium voltage-gated channel, shaker-related subfamily, beta member 2 |
| 1.7 | KCNK3 | potassium channel, subfamily K, member 3 (TASK) |
| −1.3 | KCNJ15 | potassium inwardly-rectifying channel, subfamily J, member 15 |
| 1 | KCNQ2 | potassium voltage-gated channel, KQT-like subfamily, member 2 |
| 1.6 | CLIC1 | chloride intracellular channel 1 |
| 1.3 | ASNA1 | arsA (bacterial) arsenate transporter, ATP-binding, homolog 1 |

Cytoskeleton, cell motility and extracellular matrix proteins:
(Cytoskeleton and Motility)

TABLE 35

| | | | |
|---|---|---|---|
| −2.2 | MYH11 | myosin, heavy polypeptide 11, smooth muscle | |
| 1.9 | RANBP7 | RAN binding protein 7 | |
| −1.6 | ARPC2 | actin related protein 2/3 complex, subunit 2 (34 kD) | |
| −1.2 | LRRFIP1 | leucine rich repeat (in FLII) interacting protein 1 | |
| −0.2 | TPM1 | | tropomyosin 1 (alpha) |
| 1.5 | TPM2 | | tropomyosin 2 (beta) |

(Extracelluler Matrix)

TABLE 36

| | | | |
|---|---|---|---|
| 1 | FMOD | fibromodulin | |
| 1.4 | FBN1 | | fibrillin 1 (Marfan syndrome) |
| −1.4 | MMP10 | matrix metalloproteinase 10 (stromelysin 2) | |

(Migration, Aggregation, and Adhesion)

TABLE 37

| | | | |
|---|---|---|---|
| 1 | CDH13 | cadherin 13, H-cadherin (heart) | |
| 1.5 | CDH11 | cadherin 11 (OB-cadherin, osteoblast) | |
| 1.9 | CDH2 | | cadherin 2, N-cadherin (neuronal) |
| 1.3 | CDH17 | cadherin 17, LI cadherin (liver-intestine) | |
| 1.1 | CDH6 | | cadherin 6, K-cadherin (fetal kidney) |
| −1.3 | CDH3 | | cadherin 3, P-cadherin (placental) |
| 1 | CDH13 | cadherin 13, H-cadherin (heart) | |

DNA Synthesis and repair:

TABLE 38

| | | | |
|---|---|---|---|
| −1.4 | MPG | | N-methylpurine-DNA glycosylase |
| 1 | APRT | | adenine phosphoribosyltransferase |
| −1 | NUDT1 | nudix (nucleoside diphosphate linked moiety X)-type motif 1 | |

Transcription Factors:

TABLE 39

| | | |
|---|---|---|
| −1.4 | GCN5L2 | GCN5 (general control of amino-acid synthesis, yeast, homolog)-like 2 |
| −1.2 | ZNF75 | zinc finger protein 75 (D8C6) |

Immune/Inflammation and Cytokines:

TABLE 40

| | | |
|---|---|---|
| −1.1 | TSN | translin |
| −1.4 | ELF3 | E74-like factor 3 (ets domain transcription factor) |
| −1.2 | ELF4 | E74-like factor 4 (ets domain transcription factor) |

Others:
(Known Function)

TABLE 41

| | | |
|---|---|---|
| −1.3 | PDE6G | phosphodiesterase 6G, cGMP-specific, rod, gamma |
| −1.1 | PDE6H | phosphodiesterese 6H, cGMP-specific, cone, gamma |
| −1.1 | DSCR1 | Down syndrome candidate region 1 |
| −1.4 | DUSP5 | dual specificity phosphatase 5 |
| −1.4 | LPP | LIM domain-containing preferred translocation partner in lipoma |
| 1 | YWHAB | tyrosine 3-monooxygenase/tryptophan 5-monooxygenase activation |
| −1.3 | RBMS2 | RNA binding motif, single stranded interacting protein 2 |
| −1.2 | PPP4C | protein phosphatase 4 (formerly X), catalytic subunit |
| 1.5 | PTMS | parathymosin |
| 1.1 | RES4-22 | gene with multiple splice variants near HD locus on 4p16.3 |
| −1.1 | TRIP10 | thyroid receptor interacting protein 10 (CDC42-Interacting protein) |
| 1.2 | SAP145 | spliceosome associated protein 145, SF3b subunit |

All Results from exposure to 590/810 nm LED(ZZ) or (DD) 250 ms on/100 ms off/100 pulses@3.8 mW/cm$^2$:
Mitochondrial Genes in Human Fibroblasts
590/810 nm LED(DD) 24 hrs

TABLE 42

| Ratio | Expression | Gene | Title |
|---|---|---|---|
| 0.672453 | −1.5 | APAF1 | apoptotic protease activating factor |
| 1.095028 | 1.1 | CASP3 | caspase 3, apoptosis-related cysteine protease |
| 0.752999 | −1.3 | CASP1 | caspase 1, apoptosis-related cysteine protease (interleukin 1, beta, convertase) |
| 0.871186 | −1.1 | CASP1 | caspase 1, apoptosis-related cysteine protease (interleukin 1, beta, convertase) |
| 0.766852 | −1.3 | CASP1 | caspase 1, apoptosis-related cysteine protease (interleukin 1, beta, convertase) |
| 1.611147 | 1.6 | CASP10 | caspase 10, apoptosis-related cysteine protease |
| 1.103637 | 1.1 | CASP6 | caspase 6, apoptosis-related cysteine protease |
| 0.882781 | −1.2 | CASP9 | caspase 9, apoptosis-related cysteine protease |
| 0.907027 | −1.1 | CASP6 | caspase 6, apoptosis-related cysteine protease |
| 0.732617 | −1.4 | CASP8 | caspase 8, apoptosis-related cysteine protease |
| 1.380348 | 1.4 | PPID | peptidylprolyl isomerase D (cydophilin D) |
| 0.74417 | −1.3 | FADD | Fes (TNFRSF6)-associated via death domain |
| 0.983478 | −1.0 | CFLAR | CASP8 and FADD-like apoptosis regulator |

TABLE 42-continued

| Ratio | Expression | Gene | Title |
|---|---|---|---|
| 0.613083 | −1.6 | BAK1 | BCL2-antagonist/killer 1 |
| 0.550838 | −1.8 | BNIP2 | BCL2/adenovirus E1B 19 kD-interacting protein 2 |
| 0.755466 | −1.3 | BNIP3 | BCL2/adenovirus E1B 19 kD-interacting protein 3 |
| 0.993124 | −1.0 | BECN1 | beclin 1 (coiled-coil, myosin-like BCL2-interacting protein) |
| 0.818417 | −1.2 | MCL1 | myeloid cell leukemia sequence 1 (BCL2-related) |
| 1.220192 | 1.2 | BAG1 | BCL2-associated athanogene |
| 1.422012 | 1.4 | ANT1 | adenine nucleotide translocator 1 (skeletal muscle) |
| 1.411959 | 1.4 | ANT2 | adenine nucleotide translocator 2 (fibroblast) |
| 1.239011 | 1.2 | ANT3 | adenine nucleotide translocator 3 (liver) |
| 0.988656 | −1.0 | AK2 | adenylate kinase 2 |
| 1.042014 | 1.0 | AK1 | adenylate kinase 1 |
| 0.683023 | −1.7 | PPP3CA | protein phosphatase 3 (formerly 2B), catalytic subunit, alpha isoform (calcineurin A alpha) |
| 122735 | 1.2 | PPP3CA | protein phosphatase 3 (formerly 2B), catalytic subunit, alpha isoform (calcineurin A alpha) |
| 1.518863 | 1.5 |  | Human calcineurin B mRNA, complete cds |
| 1.063044 | 1.1 | CAPN1 | calpain, large polypeptide L1 |
| 1.317045 | 1.3 | CAPN2 | calpain, large polypeptide L2 |
| 1.622338 | 1.6 | CAPN4 | calpain, small polypeptide |
| 0.861747 | −1.2 | RAF1 | v-raf-1 murine leukemia viral oncogene homolog 1 |
| 0.484376 | −2.2 | BRAF | v-raf murine sarcoma viral oncogene homolog B1 |
| 0.737887 | −1.4 | FKBP5 | FK506-binding protein 5 |
| 2.18475 | 2.2 |  | Human FKBP mRNA for FK-506 binding protein |
| 1.107759 | 1.1 | FKBP1B | FK506-binding protein 1B (12.6 kD) |
| 0.926774 | −1.1 | FKBP2 | FK506-binding protein 2 (13 kD) |
| 0.774274 | −1.3 | AKT1 | v-akt murine thymoma viral oncogene homolog 1 |
| 1.612154 | 1.8 | ANXA5 | annexin A5 |
| 1.710519 | 1.7 | ANXA5 | annexin A5 |
| 1.440048 | 1.4 | ANXA5 | annexin A5 |
| 0.907384 | −1.1 | ANXA7 | annexin A7 |
| 1.383435 | 1.4 | ANXA7 | annexin A7 |
| 1.61359 | 1.6 | ANXA7 | annexin A7 |
| 2.760601 | 2.8 | ANXA1 | annexin A1 |
| 1.668865 | 1.7 | ANXA1 | annexin A1 |
| 1.832097 | 1.8 | ANXA1 | annexin A1 |
| 1.214869 | 1.2 | ANXA6 | annexin A6 |
| 0.833622 | −1.2 | ANXA8 | annexin A8 |
| 0.94813 | −1.1 | ANXA8 | annexin A8 |
| 0.588338 | −1.7 | ANXA8 | annexin A8 |
| 1.670277 | 1.7 | ANXA4 | annexin A4 |
| 1.528849 | 1.5 | ANXA4 | annexin A4 |
| 1.729019 | 1.7 | ANXA4 | annexin A4 |
| 1.861111 | 1.9 | S100A10 | S100 calcium-binding protein A10 (annexin II ligand, calpactin I, light polypeptide (p11)) |
| 1.83305 | 1.8 | S100A10 | S100 calcium-binding protein A10 (annexin II ligand, calpactin I, light polypeptide (p11)) |
| 1.477795 | 1.5 | S100A10 | S100 calcium-binding protein A10 (annexin II ligand, calpactin I, light polypeptide (p11)) |
| 1.438005 | 1.4 | ANXA11 | annexin A11 |
| 1.698309 | 1.7 | ANXA11 | annexin A11 |
| 1.672616 | 1.7 | ANXA11 | annexin A11 |
| 1.021433 | 1.0 | ANXA13 | annexin A13 |
| 1.024994 | 1.0 | ANXA13 | annexin A13 |
| 0.669451 | −1.5 | ANXA13 | annexin A13 |
| 1.328973 | 1.3 | ANXA6 | annexin A6 |
| 1.240924 | 1.2 | ANXA6 | annexin A6 |
| 0.894772 | −1.1 | ANXA6 | annexin A6 |
| 1.538057 | 1.5 | SOD3 | superoxide dismutase 3, extracellular |
| 0.987425 | −1.0 | CCS | copper chaperone for superoxide dismutase |

TABLE 42-continued

| Ratio | Expression | Gene | Title |
|---|---|---|---|
| 1.002773 | 1.0 | TP53 | tumor protein p53 (Li-Fraumeni syndrome) |
| 0.944431 | −1.1 | PIG11 | p53-induced protein |
| 0.735969 | −1.4 | TP53BP1 | tumor protein 53-binding protein, 1 |
| 1.009404 | 1.0 | TP53BPL | tumor protein p53-binding protein |
| 0.63884 | −1.6 | TP53BP2 | tumor protein p53-binding protein, 2 |
| 0.912983 | −1.1 | IRLB | c-myc promoter-binding protein |
| 1.069829 | 1.1 | PTEN | phosphatase and tensin homolog (mutated in multiple advanced cancers 1) |
| 0.821975 | −1.2 | NOS2A | nitric oxide synthase 2A (inducible, hepatocytes) |
| 0.959432 | −1.0 | NOS3 | nitric oxide synthase 3 (endothelial cell) |
| 1.472414 | 1.5 | NOS3 | nitric oxide synthase 3 (endothelial cell) |

590/810 nm LED(DD)@4 hrs

TABLE 43

| Ratio | Expression | Gene | Title |
|---|---|---|---|
| 0.708927 | −1.4 | APAF1 | apoptotic protease activating factor |
| 1.032817 | 1.0 | CASP3 | caspase 3, apoptosis-related cysteine protease |
| 0.762964 | −1.3 | CASP1 | caspase 1, apoptosis-related cysteine protease (interleukin 1, beta, convertase) |
| 0.6853 | −1.5 | CASP1 | caspase 1, apoptosis-related cysteine protease (interleukin 1, beta, convertase) |
| 1.189727 | 1.2 | CASP1 | caspase 1, apoptosis-related cysteine protease (interleukin 1, beta, convertase) |
| 1.003431 | 1.0 | CASP10 | caspase 10, apoptosis-related cysteine protease |
| 1.511354 | 1.5 | CASP6 | caspase 6, apoptosis-related cysteine protease |
| 1.047359 | 1.0 | CASP9 | caspase 9, apoptosis-related cysteine protease |
| 1.009142 | 1.0 | CASP6 | caspase 6, apoptosis-related cysteine protease |
| 1.267594 | 1.3 | GASPS | caspase 8, apoptosis-related cysteine protease |
| 0.758725 | −1.3 | CFLAR | CASP8 and FADD-like apoptosis regulator |
| 1.459427 | 1.5 | PPID | pepfidylprolylisomerase D (cydophilin D) |
| 0.707391 | −1.4 | FADO | Fas (TNFRSF6)-associated via death domain |
| 1.060392 | 1.1 | BAK1 | BCL2-antagonist/killer 1 |
| 1.056214 | 1.1 | BNIP2 | BCL2/adenovirus EI B 19 kD-interacting protein 2 |
| 1.049853 | 1.0 | BNIP3 | BCL2/adenovirus EI B 19 kD-interacting protein 3 |
| 0.922743 | −1.1 | BECN1 | bedin 1 (coiled-coil, myosin-like BCL2-interacting protein) |
| 0.692976 | −1.4 | MCL1 | myeloid cell leukemia sequence 1 (BCL2-related) |
| 0.751831 | −1.3 | BAG1 | BCL2-associated athanogene |
| 0.800641 | −1.2 | ANT1 | adenine nucleotide translocator 1 (skeletal muscle) |
| 0.938585 | −1.1 | ANT2 | adenine nucleotide translocator 2 (fibroblast) |
| 0.668039 | −1.5 | ANT3 | adenine nucleotide translocator 3 (liver) |
| 0.538932 | −1.9 | AK1 | adenylate kinase 1 |
| 1.459483 | 1.5 | AK2 | adenylate kinase 2 |
| 1.204731 | 1.2 | PPP3CA | protein phosphatase 3 (formerly 2B), catalytic subunit, alpha isoform (calcineurin A alpha) |
| 0.97708 | −1.0 | PPP3CA | protein phosphatase 3 (formerly 2B), catalytic subunit, alpha isoform (calcineurin A alpha) |
| 0.928503 | −1.1 | — | ESTs, Moderately similar to calcin urin B beta-2 [M. musculus] |

TABLE 43-continued

| Ratio | Expression | Gene | Title |
|---|---|---|---|
| 0.809383 | −1.6 | CAPN4 | calpain, small polypeptide |
| 1.088519 | 1.1 | CAPN1 | calpain, large polypeptide L1 |
| 0.864897 | −1.2 | CAPN2 | calpain, large polypeptide L2 |
| 0.828817 | −1.2 | RAF1 | v-raf-1 murine leukemia viral oncogene homolog 1 |
| 0.998575 | −1.0 | BRAF | v-raf murine sarcoma viral oncogene homolog B1 |
| 0.816404 | −1.2 | FKBP5 | FK506-binding protein 5 |
| 0.864482 | −1.2 | — | Human FKBP mRNA for FK-506 binding protein |
| 1.232883 | 1.2 | FKBPIB | FK506-binding protein 1B (12.6 kD) |
| 1293683 | 1.3 | FKBP2 | FK506-binding protein 2 (13 kD) |
| 0.832658 | −1.2 | AKT1 | v-akt murine thymoma viral oncogene homolog 1 |
| 0.724822 | −1.4 | ANXA5 | annexin A5 |
| 0.724822 | −1.4 | ANXA5 | annexin A5 |
| 1.28223 | 1.3 | ANXA5 | annexin A5 |
| 1.172376 | 1.2 | ANXA7 | annexin A7 |
| 0.815715 | −1.2 | ANXA7 | annexin A7 |
| 0.859959 | −1.2 | ANXA7 | annexin A7 |
| 0.671086 | −1.5 | ANXA1 | annexin A1 |
| 0.741183 | −1.3 | ANXA1 | annexin A1 |
| 1.2303 | 1.2 | ANXA1 | annexin A1 |
| 0.959943 | −1.0 | ANXA6 | annexin A6 |
| 0.969168 | −1.0 | ANXA8 | annexin A8 |
| 0.85047 | −1.2 | ANXA8 | annexin A8 |
| 0.78908 | −1.3 | ANXA8 | annexin A8 |
| 0.613521 | −1.6 | ANXA4 | annexin A4 |
| 0.500984 | −2.0 | ANXA4 | annexin A4 |
| 1.185163 | 1.2 | ANXA4 | annexin A4 |
| 0.650599 | −1.5 | S100A10 | S100 calcium-binding protein A10 (annexin II ligand, calpactin I, light polypeptide (p11)) |
| 0.597934 | −1.7 | S100A10 | S100 calcium-binding protein A10 (annexin II ligand, calpactin I, light polypeptide (p11)) |
| 0.801246 | −1.2 | S100A10 | S100 calcium-binding protein A10 (annexin II ligand, calpactin I, light polypeptide (p11)) |
| 0.537825 | −1.9 | ANXA11 | annexin A11 |
| 0.70757 | −1.4 | ANXA11 | annexin A11 |
| 1.169766 | 1.2 | ANXA11 | annexin A11 |
| 1.332475 | 1.3 | ANXA13 | annexin A13 |
| 1.126206 | 1.1 | ANXA13 | annexin A13 |
| 1.365489 | 1.4 | ANXA13 | annexin A13 |
| 1.020112 | 1.0 | ANXA6 | annexin A6 |
| 0.95119 | −1.1 | ANXA6 | annexin A6 |
| 1.283909 | 1.3 | ANXA6 | annexin A6 |
| 0.693786 | −1.4 | SOD3 | superoxide dismutase 3, extracellular |
| 0.958899 | −1.0 | CCS | copper chaperone for superoxide dismutase |
| 1.146757 | 1.1 | TP53 | tumor protein p53 (U-Fraumeni syndrome) |
| 0.724835 | −1.4 | PIG11 | p53-induced protein |
| 0.79645 | −1.3 | TP53BP1 | tumor protein 53-binding protein, 1 |
| 0.9907 | −1.0 | TP53BPL | tumor protein p53-binding protein |
| 0.969112 | −1.0 | TP53BP2 | tumor protein p53-binding protein, 2 |
| 0.865631 | −1.2 | IRLB | c-myc promoter-binding protein |
| 1.031368 | 1.0 | PTEN | phosphatase and tensin homolog (mutated in multiple advanced cancers 1) |
| 0.91541 | −1.1 | NOS2A | nitric oxide synthase 2A (inducible, hepatocytes) |
| 0.801248 | −1.2 | NOS3 | nitric oxide synthase 3 (endothelial cell) |
| 1.081913 | 1.1 | NOS3 | nitric oxide synthase 3 (endothelial cell) |

All Results from exposure to 590/810 nm LED(ZZ) or (DD) 250 ms on/100 ms off/100 pulses@3.5 mW/cm$^2$ MAPK Related Genes 890/910 nm LED(DD)@24 hrs

TABLE 44

| Ratio | Expression | Gene | Title |
|---|---|---|---|
| 2.151532 | 2.15 | ITGB5 | integrin, beta 5 |
| 2.137362 | 2.14 | PRKCI | protein kinase C, iota |
| 2.113886 | 2.11 | | Human bets-10 integrin MRNA, cytoplasmic domain. partial cds |
| 1.622733 | 1.62 | FOS | v-fos FBJ murine osteosarcoma viral oncogene homolog |
| 1.597241 | 1.60 | | Human beta-1D integrin mRNA, cytoplasmic domain, partial cds |
| 1.582695 | 1.58 | PRKCI | protein kinase C, iota |
| 1.563014 | 1.58 | PLCE | Phospholipase C, epsilon |
| 1.560155 | 1.56 | DGKA | diacylglycerol kinase, alpha (80 kD) |
| 1.53918 | 1.54 | | Human beta-1D integrin mRNA, cytoplasmic domain, partial cds |
| 1.526946 | 1.53 | PRKCM | protein kinase C, mu |
| 1.512534 | 1.51 | RHEB2 | Ras homolog enriched in brain 2 |
| 1.486994 | 1.49 | RAC1 | ras-related C3 botullnum toxin substrate 1 (rho family, small GTP binding protein Rac1) |
| 1.456415 | 1.48 | PRKCM | protein kinase C, mu |
| 1.350993 | 1.35 | PRKCH | protein kinase C, eta |
| 1.343276 | 1.34 | RAB9 | RAB9, member RAS oncogene family |
| 1.341059 | 1.34 | ITGAL | Integrin, alpha L (antigen CD11A (p180), lymphocyte function-associated antigen 1; alpha polypeptide) |
| 1.338949 | 1.34 | RAB2L | RAB2, member RAS oncogene family-like |
| 1.338766 | 1.34 | MAP4K5 | mitogen-activated protein kinase kinase kinase kinase 5 |
| 1.283072 | 1.28 | ITGAL | integrin, alpha L (antigen CD11A (p180), lymphocyte function-associated antigen 1; alpha polypeptide) |
| 1.280278 | 1.28 | PRKCH | protein kinase C, eta |
| 1.249952 | 1.25 | ITGAL | integrin, alpha L (antigen CD11A (p180), lymphocyte function-associated antigen 1; alpha polypeptide) |
| 1.240077 | 1.24 | PLCB3 | phospholipase C, beta 3 (phosphatidylinositol-specific) |
| 1.230521 | 1.23 | ITGA7 | Integrin, alpha 7 |
| 1.221321 | 1.22 | RAC3 | ras-related C3 botulinum toxin substrate 3 (rho family, small GTP binding protein Rac3) |
| 1.213243 | 1.21 | MAPK14 | mitogen-activated protein kinase 14 |
| 1.211197 | 1.21 | ARHB | ras homolog gene family, member B |
| 1.207135 | 1.21 | | ESTs, Weakly similar to phospholipase c delta 1 [H.sapiens] |
| 1.201018 | 1.20 | ITGB8 | integrin, beta 8 |
| 1.189308 | 1.19 | PRKCI | protein kinase C, iota |
| 1.148141 | 1.15 | ITGA4 | integrin, alpha 4 (antigen CD49D, alpha 4 subunit of VLA-4 receptor) |
| 1.138195 | 1.14 | ICAP-1A | integrin cytoplasmic domain-associated protein 1 |
| 1.133706 | 1.13 | RAB7 | RAB7, member RAS oncogene family |
| 1.128942 | 1.13 | ARHE | ras homolog gene family, member E |
| 1.126723 | 1.13 | CD47 | CD47 antigen (Rh-related antigen, integrin-associated signal transducer) |
| 1.12348 | 1.12 | RABL | RAB, member of RAS oncogene family-like |
| 1.109055 | 1.11 | RAB1 | RAB1, member RAS oncogene family |
| 1.101203 | 1.10 | MAPK1 | mitogen-activated protein kinase 1 |
| 1.095657 | 1.10 | RAB7 | RAB7, member RAS oncogene family |
| 1.090654 | 1.09 | ARHH | ras homolog gene family, member H |
| 1.074483 | 1.07 | ARAF1 | v-raf murine sarcoma 3611 viral oncogene homolog 1 |
| 1.061058 | 1.08 | RAB11A | RAB11A, member RAS oncogene family |
| 1.05968 | 1.06 | ITGA3 | integrin, alpha 3 (antigen CD49C, alpha 3 subunit of VLA-3 receptor) |
| 1.056695 | 1.06 | RAB6 | RAB6, member RAS oncogene family |
| 1.056435 | 1.06 | ITGA7 | integrin, alpha 7 |
| 1.046506 | 1.05 | PRKCD | protein kinase C, delta |
| 1.044537 | 1.04 | UTGB4 | integrin, beta 4 |
| 1.043696 | 1.04 | PLCE | phospholipase C, epsilon |
| 1.030882 | 1.03 | ITGA8 | integrin, alpha 8 |
| 1.023886 | 1.02 | ITGB5 | integrin, beta 5 |
| 1.023219 | 1.02 | DGKZ | diacylglycerol kinase, zeta (104 kD) |
| 1.019702 | 1.02 | ITGA4 | integrin, alpha 4 (antigen CD49D, alpha 4 subunit of VLA-4 receptor) |

TABLE 44-continued

| Ratio | Expression | Gene | Title |
|---|---|---|---|
| 1.018855 | 1.02 | MAP2K3 | mitogen-activated protein kinase kinase 3 |
| 1.009852 | 1.01 | ICAP-1A | integrin cytoplasmic domain-associated protein 1 |
| 1.005006 | 1.01 | ITGA2 | integrin, alpha 2 (CD49B, alpha 2 subunit of VLA-2 receptor) |
| 1.000542 | 1.00 | MAPK6 | mitogen-activated protein kinase 6 |
| 0.998091 | −1.00 | ITGA7 | integrin, alpha 7 |
| 0.988265 | −1.01 | RREB1 | ras responsive element binding protein 1 |
| 0.985568 | −1.01 | ITGA3 | integrin, alpha 3 (antigen CD49C, alpha 3 subunit of VLA-3 receptor) |
| 0.977811 | −1.02 | PRKCB1 | protein kinase C, beta 1 |
| 0.971294 | −1.03 | ITGA4 | integrin, alpha 4 (antigen CD49D, alpha 4 subunit of VLA-4 receptor) |
| 0.970334 | −1.03 | MKNK1 | MAP kinase-interacting serine/threonine kinase 1 |
| 0.969316 | −1.03 | ITGAX | integrin, alpha X (antigen CD11C (p150), alpha polypeptide) |
| 0.98829 | −1.03 | ITGA3 | integrin, alpha 3 (antigen CD49C, alpha 3 subunit of VLA-3 receptor) |
| 0.965269 | −1.04 | PRKCH | protein kinase C, eta |
| 0.964851 | −1.04 | TGFB1 | transforming growth factor, beta 1 |
| 0.960995 | −1.04 | JUN | Jun activation domain binding protein |
| 0.954348 | −1.05 | ITGAX | integrin, alpha X (antigen CD11C (p150), alpha polypeptide) |
| 0.949425 | −1.05 | RAC1 | ras-related C3 botulinum toxin substrate 1 (rho family, small GTP binding protein Rac1) |
| 0.948566 | −1.05 | ITGA1 | integrin, alpha 1 |
| 0.948908 | −1.06 | | integrin beta 3 (alternatively spliced, clone beta 3C) (human, erythroleukemia cell HEL, mRNA Partial, 409 nt) |
| 0.946033 | −1.06 | PRKCD | protein kinase C, delta |
| 0.945957 | −1.06 | PRKCD | protein kinase C, delta |
| 0.944384 | −1.06 | MADD | MAP-kinase activating death domain |
| 0.936588 | −1.07 | GADD45A | growth arrest and DNA-damage-inducible, alpha |
| 0.935858 | −1.07 | NRAS | neuroblastoma RAS viral (v-ras) oncogene homolog |
| 0.932328 | −1.07 | CD47 | CD47 antigen (Rh-related antigen, integrin-associated signal transducer) |
| 0.929638 | −1.08 | ICAP-1A | integrin cytoplasmic domain-associated protein 1 |
| 0.920586 | −1.09 | PLCG2 | phospholipase C, gamma 2 (phosphatidylinositol-specific) |
| 0.917784 | −1.09 | EGF | epidermal growth factor |
| 0.916995 | −1.09 | RAB7 | RAB7, member RAS oncogene family |
| 0.916945 | −1.09 | USF2 | upstream transcription factor 2, c-fos interacting |
| 0.91587 | −1.09 | ARHA | ras homolog gene family, member A |
| 0.909302 | −1.10 | | integrin beta 3 (alternatively spliced, clone beta 3C) (human, erythroleukemia cell HEL, mRNA Partial, 409 nt) |
| 0.898683 | −1.11 | JUN | Jun activation domain binding protein |
| 0.891325 | −1.12 | TGFB1I1 | transforming growth factor beta 1, induced transcript 1 |
| 0.889904 | −1.12 | RAB6 | RAB6, member RAS oncogene family |
| 0.887989 | −1.13 | USF2 | upstream transcription factor 2, c-fos interacting |
| 0.886187 | −1.13 | ITGA1 | integrin, alpha 1 |
| 0.881957 | −1.13 | PLCD1 | phospholipase C, delta 1 |
| 0.881842 | −1.13 | PRKCM | protein kinase C, mu |
| 0.881063 | −1.13 | PRKCB1 | protein kinase C, beta 1 |
| 0.880197 | −1.14 | | ESTs, Moderately similar to RAS-LIKE PROTEIN TC10 [*H. sapiens*] |
| 0.889822 | −1.16 | ILK | integrin linked kinase |
| 0.861747 | −1.18 | RAF1 | v-raf-1 murine leukemia viral oncogene homolog 1 |
| 0.860204 | −1.16 | ITGA8 | integrin, alpha 8 |
| 0.858078 | −1.17 | ITGA6 | integrin, alpha 6 |
| 0.656894 | −1.17 | ITGAX | integrin, alpha X (antigen CD11C (p150), alpha polypeptide) |
| 0.849359 | −1.18 | RIN1 | ras inhibitor |
| 0.840918 | −1.19 | MAP2K2 | mitogen-activated protein kinase kinase 2 |
| 0.839859 | −1.19 | ITGA8 | integrin, alpha 8 |
| 0.835849 | −1.20 | ITGB5 | integrin. beta 5 |
| 0.833758 | −1.20 | RAB32t | RAB32, member RAS oncogene family |
| 0.829937 | −1.20 | MAP2K6 | mitogen-activated protein kinase kinase 6 |
| 0.818112 | −1.22 | PLCB2 | phospholipase C, beta 2 |
| 0.816701 | −1.22 | PRKCB1 | protein kinase C, beta 1 |
| 0.808515 | −1.24 | ITGAV | integrin, alpha V (vitronectin receptor, alpha polypeptide, antigen CD51) |
| 0.795285 | −1.26 | MAP3K10 | mitogen-activated protein kinase kinase kinase 10 |
| 0.787248 | −1.27 | MAPK9 | mitogen-activated protein kinase 9 |
| 0.784515 | −1.27 | JUN | Jun activation domain binding protein |
| 0.773271 | −1.29 | | Human ras inhibitor mRNA, 3' end |
| 0.772018 | −1.30 | | ELK1, member of ETS oncogene family |
| 0.767083 | −1.30 | MAPK10 | mitogen-activated protein kinase 10 |
| 0.767129 | −1.30 | EGF | epidermal growth factor |
| 0.783073 | −1.31 | RAB5A | RAB5A, member RAS oncogene family |
| 0.757051 | −1.32 | EGF | epidermal growth factor |
| 0.744829 | −1.34 | MAP3K5 | mitogen-activated protein kinase kinase kinase 5 |
| 0.743093 | −1.36 | MAP3K5 | mitogen-activated protein kinase kinase kinase 5 |
| 0.741843 | −1.35 | | Human DNA sequence from cosmid U237H1 contains Ras like GTPase and ESTs |
| 0.738327 | −1.35 | | Integrin beta 3 (alternatively spliced, clone beta 3C) (human, erythroleukemia cell HEL, mRNA Partial, 409 nt) |
| 0.723984 | −1.38 | PLCG1 | phospholipase C, gamma 1 (formerly subtype 148) |
| 0.723884 | −1.38 | ITGA2 | integrin, alpha 2 (CD49B, alpha 2 subunit of VLA-2 receptor) |
| 0.715877 | −1.40 | ITGB8 | integrin, beta 8 |
| 0.713303 | −1.40 | RAB2 | RAB2, member RAS oncogene family |
| 0.709355 | −1.41 | PRKCA | protein kinase C, alpha |
| 0.699671 | −1.43 | USF2 | upstream transcription factor 2, c-fos interacting |
| 0.69357 | −1.44 | ITGAV | integrin, alpha V (vitronectin receptor, alpha polypeptide, antigen CD51) |
| 0.689672 | −1.45 | ITGA1 | Integrin, alpha 1 |
| 0.684061 | −1.48 | | Human transcription fact r NFATX mRNA, complete cds |
| 0.683894 | −1.46 | PLCE | phospholipase C, epsilon |
| 0.67941 | −1.47 | ITGB4 | integrin, beta 4 |
| 0.654839 | −1.53 | CD47 | CD47 antigen (Rh-related antigen, integrin-associated signal transducer) |
| 0.645803 | −1.55 | PRKCA | protein kinase C, alpha |
| 0.64153 | −1.56 | 1TGB4 | integrin, beta 4 |
| 0.641138 | −1.58 | ITGA8 | integrin, alpha 6 |
| 0.833577 | −1.58 | | Homo sapiens protein kinase C-binding protein RACK7 mRNA, partial cds |
| 0.632221 | −1.58 | MAP2K3 | mitogen-activated protein kinase kinase 3 |
| 0.824919 | −1.80 | RASA1 | RAS p21 protein activator (GTPase activating protein) 1 |
| 0.809886 | −1.64 | MAP3K5 | mitogen-activated protein kinase kinase kinase 5 |
| 0.805607 | −1.85 | FOSB | FBJ murine osteosarcoma viral oncogene homolog B |
| 0.60518 | −1.65 | NRGN | neurogranin (protein kinase C substrate, RC3) |
| 0.598192 | −1.87 | ATF3 | activating transcription factor 3 |
| 0.561799 | −1.78 | ARHE | ras homolog gene family, member E |
| 0.56023 | −1.76 | RACK17 | protein kinase C-binding protein |
| 0.554447 | −1.80 | TGFA | transforming growth factor, alpha |
| 0.536929 | −1.86 | PIP5K1A | phosphatidylinositol-4-phosphate 5-kinase, type I, alpha |
| 0.525542 | −1.90 | MAPK4 | mitogen-activated protein kinase 4 |
| 0.524533 | −1.91 | ITGA2 | integrin, alpha 2 (CD49B, alpha 2 subunit of VLA-2 receptor) |
| 0.523448 | −1.91 | ITGB8 | integrin, beta 8 |
| 0.518371 | −1.93 | PRKCA | protein kinase C, alpha |
| 0.510159 | −1.96 | ARHG | ras homolog gene family, member G (rho G) |

TABLE 44-continued

| Ratio | Expression | Gene | Title |
|---|---|---|---|
| 0.506256 | −1.98 | MAP2K7 | mitogen-activated protein kinase kinase 7 |
| 0.492448 | −2.03 | ITGA6 | integrin, alpha 6 |
| 0.487227 | −2.05 | PIP5K1B | phosphatidyinositol-4-phosphate 5-kinase, type I, beta |
| 0.475903 | −2.10 | TGFB3 | transforming growth factor, beta 3 |
| 0.464378 | −2.15 | BRAF | v-raf murine sarcoma viral oncogene homolog B1 |
| 0.444169 | −2.25 | ITGAV | integrin, alpha V (vitronectin receptor, alpha polypeptide, antigen CD51) |
| 0.442003 | −2.26 | | Human transcription factor junB (junB) gene, 5' region and complete cds |

590/810 mn LED(DD)@4 hrs

TABLE 45

| Ratio | Expression | Gene | Title |
|---|---|---|---|
| 1.845274 | 1.85 | RAB2 | RAB2, member RAS oncogene family |
| 1.754999 | 1.75 | NRAS | neuroblastoma RAS viral (v-ras) oncogene homolog |
| 1.854462 | 1.65 | ITGB8 | Integrin, beta 8 |
| 1.58747 | 1.57 | PLCE | phospholipase C, epsilon |
| 1.511982 | 1.51 | NRGN | neurogranin (protein kinase C substrate, RC3) |
| 1.473993 | 1.47 | PRKCZ | Protein Idnase C. zeta |
| 1.454388 | 1.45 | ARHE | ras homolog gene family, member E |
| 1.422816 | 1.42 | ARHH | ras homolog gene family, member H |
| 1.418485 | 1.42 | | Integrin, alpha M |
| 1.404744 | 1.40 | | Human transaiption factor junB (junB) gene, 5' region and complete cds |
| 1.391358 | 1.39 | ITGAV | integrin, alpha V (vitronectin receptor, alpha polypeptide, antigen CD51) |
| 1.377873 | 1.38- | | integrin beta 3 {alternatively spliced, clone beta 3C}(human, arythroleukernis cell HEL, mRNA Partial, 409 n) |
| 1.373878 | 1.37 | ITGA2 | integrin, alpha 2 (CD496, alpha 2 subunit of VLA-2 receptor) |
| 1.342823 | 1.34 | EGF | epidermal growth factor |
| 1.34281 | 1.34 | MAP2K3 | mitogen-activated protein kinase kinase 3 |
| 1.332214 | 1.33 | DGKA | diacylglycerol kinase, alpha (80 kD) |
| 1.312835 | 1.31 | ATF3 | activating transcription factor 3 |
| 1.306887 | 1.31 | RAC1 | ras-related C3 botulinum toxin substrate 1 (rho family, small GTP binding protein Rac1) |
| 1.288695 | 1.29 | MAPK14 | mitogen-activated protein kinase 14 |
| 1.283108 | 1.28 | ITGA1 | integrin, alpha 1 |
| 1.287243 | 1.27 | PRKCB1 | protein kinase C, beta 1 |
| 1.248459 | 1.25 | PRKCG | Protein kinase C, gamma |
| 1.237471 | 1.24 | RAB2L | RAB2, member RAS oncogene family-like |
| 1.233967 | 1.23 | MAPK4 | mitogen-activated protein kinase 4 |
| 1.230417 | 1.23 | USF2 | upstream transcription factor 2, c-fos interacting |
| 1.223974 | 1.22 | MAP3K5 | mitogen-activated protein kinase kinase 5 |
| 1.218357 | 1.22 | CD47 | CD47 antigen (Rh-related antigen, integrin-associated signal transducer) |
| 1.209669 | 1.21 | MAP3K5 | mitogen-activated protein kinase kinase 5 |
| 1.208324 | 1.21 | ICAP-1A | integrin cytoplasmic domain-associated protein 1 |
| 1.205916 | 1.21 | PLCD4 | ESTs, Weakly similar to phospholipase c delta 1 [*H. sapiens*] |
| 1.199329 | 1.20 | PRKCB1 | protein kinase C. beta 1 |
| 1.185533 | 1.19 | RAB1 | RAB1, member RAS oncogene family |

TABLE 45-continued

| Ratio | Expression | Gene | Title |
|---|---|---|---|
| 1.181919 | 1.18 | EGF | epidermal growth factor |
| 1.158032 | 1.16 | MAP2K2 | mitogen-activated protein kinase kinase 2 |
| 1.149777 | 1.15 | PLCE | phospholipase C, epsilon |
| 1.142878 | 1.14 | RAB32 | RAB32, m mbar RAS oncogene family |
| 1.139165 | 1.14 | PLCB3 | phospholipase C, beta 3 (phosphatidylinositol-specific) |
| 1.134717 | 1.13 | MAP3K5 | mitogen-activated protein kinase kinase 5 |
| 1.134033 | 1.13 | RAB7 | RAB7, member RAS oncogene family |
| 1.120759 | 1.12 | PRKCA | protein kinase C, alpha |
| 1.119516 | 1.12 | RAB6 | RAB6, member RAS oncogene family |
| 1.113802 | 1.11 | PRKCQ | PROTEIN KINASE C, THETA TYPE |
| 1.105556 | 1.11 | EGF | epidermal growth factor |
| 1.103501 | 1.10 | ITGA1 | integrin alpha 1 |
| 1.100796 | 1.10 | | integrin alpha E precursor |
| 1.100552 | 1.10 | RAB7 | RAB7, member RAS oncogene family |
| 1.099328 | 1.10 | RACK17 | protein kinase C-binding protein |
| 1.095719 | 1.10 | PRKCG | Protein kinase C, gamma |
| 1.089447 | 1.09 | ITGB5 | integrin, beta 5 |
| 1.088832 | 1.09 | ITGA1 | integrin, alpha 1 |
| 1.082187 | 1.08 | MAPK9 | mitogen-activated protein kinase 9 |
| 1.077731 | 1.08 | CD47 | CD47 antigen (Rh-related antigen, integrin-associated signal transducer) |
| 1.073758 | 1.07 | ITGA2 | integrin, alpha 2 (CD49B, alpha 2 subunit of VLA-2 receptor) |
| 1.071914 | 1.07 | | integrin beta 3 (alternatively spliced, clone beta 3C) (human, erythroleukemia cell HEL, mRNA Partial, 409 nt) |
| 1.065532 | 1.07 | | PRKCQ PROTEIN KINASE C. THETA TYPE |
| 1.062551 | 1.08 | ITGAX | integrin, alpha X (antigen CD11C (p150), alpha potypeptlde) |
| 1.061789 | 1.06 | ITGB8 | integrin, beta 8 |
| 1.059067 | 1.08 | PRKCQ | PROTEIN KINASE C. THETA TYPE |
| 1.057581 | 1.06 | PRKCB1 | protein kinase C, beta 1 |
| 1.054268 | 1.05 | TGFB3 | transforming growth factor, beta 3 |
| 1.036853 | 1.04- | | Human ras inhibitor mRNA, 3' end |
| 1.03848 | 1.04 | RAC3 | ras-related C3 botulinum toxin substrate 3 (rho family, small GTP binding protein Rac3) |
| 1.032728 | 1.03 | JUN | Jun activation domain binding protein |
| 1.028984 | 1.03 | USF2 | upstream transcription factor 2, c-fos interacting |
| 1.028428 | 1.03 | JUN | Jun activation domain binding protein |
| 1.020173 | 1.02 | ILK | Integrin-linked kinase |
| 1.015136 | 1.02 | MAP2K7 | mitogen-activated protein kinase kinase 7 |
| 1.013153 | 1.01 | | integrin beta 3 (alternatively spliced, clone beta 3C) [human, erythroleukemia cell HEL, mRNA Partial, 409 nt] |
| 1.008267 | 1.01 | PLCG1 | phospholipase C, gamma 1 (formerly subtype 148) |
| 0.998575 | −1.00 | BRAF | v-ref murine sarcoma viral oncogene homolog B1 |
| 0.998967 | −1.00 | ITGA4 | integrin, alpha 4 (antigen CD49D, alpha 4 subunit of VLA-4 receptor) |
| 0.993575 | −1.01 | ITGB4 | integrin, beta 4 |
| 0.992709 | −1.01 | ITGA8 | integrin, alpha 6 |
| 0.985833 | −1.01 | MAPK6 | mitogen-activated protein kinase 8 |
| 0.985323 | −1.01 | ITGAX | integrin, alpha X (antigen CD11C (p150), alpha polypeptide) |
| 0.984502 | −1.02 | ITGA3 | integrin, alpha 3 (antigen CD49C, alpha 3 subunit of VLA-3 receptor) |
| 0.983398 | −1.02 | RAB11 | RAB11A, member RAS oncogene family |
| 0.982142 | −1.02 | — | Integrin, alpha M |
| 0.977853 | −1.02 | ARHA | ras homolog gene family, member A |

TABLE 45-continued

| Ratio | Expression | Gene | Title |
|---|---|---|---|
| 0.973833 | −1.03 | TGFA | transforming growth factor, alpha |
| 0.964758 | −1.04 | JUN | Jun activation domain binding protein |
| 0.964305 | −1.04 | ITGAV | integrin, alpha V (vitronectin receptor, alpha polypep6de, antigen CD51) |
| 0.983123 | −1.04 | ITGAV | integrin, alpha V (vitronectin receptor, alpha polypeptide, antigen CD51) |
| 0.960907 | −1.04 | PLCB2 | phosphoilpase C, beta 2 |
| 0.959247 | −1.04 | PRKCG | Protein kinase C, gamma |
| 0.958255 | −1.04 | ITGB4 | Nevin, beta 4 |
| 0.967821 | −1.04 | ARHE | ras homolog gene family, member E |
| 0.955071 | −1.05 | PRKCH | protein kinase C, eta 2 |
| 0.953312 | −1.05 | PRKCD | protein kinase C, delta |
| 0.953116 | −1.05 | MAPKAPK | Human MAPKAP kinase (3pK) mRNA, complete cds |
| 0.945431 | −1.06 | MADD | MAP-kinase activating death domain |
| 0.936479 | −1.07 | PRKCA | protein kinase C, alpha |
| 0.933294 | −1.07 | ITGA8 | integrin, alpha 8 |
| 0.93031 | −1.07 | RIN1 | ras inhibitor |
| 0.928811 | −1.08 | MAP2K3 | mitogen-activated protein kinase kinase 3 |
| 0.923683 | −1.08 | FOS8 | FBJ minim osteosarcoma viral oncogene homolog B |
| 0.920474 | −1.09 | ARAF1 | v-raf murine sarcoma 3611 viral oncogene homolog 1 |
| 0.920277 | −1.09 | ITGA4 | integrin, alpha 4 (antigen CD49D, alpha 4 subunit of VLA-4 receptor) |
| 0.916472 | −1.09 | RAB8 | RAB6, member RAS oncogene family |
| 0.918115 | −1.09 | PLCG2 | phospholipase C, gamma 2 (phosphatidlinositol-specific) |
| 0.915938 | −1.09 | PRKCZ | Protein kinase C, zeta |
| 0.914158 | −1.09 | KSR | kinase suppressor of ras |
| 0.90698 | −1.10 | ICAP-1A | integrin cytoplasmic domain-associated protein 1 |
| 0.905881 | −1.10 | | integrin, alpha M |
| 0.900885 | −1.11 | ITGA6 | integrin, alpha 6 |
| 0.899308 | −1.11 | TGFB1/1 | transforming growth factor beta 1 induced transcript |
| 0.896301 | −1.12 | MAPK1 | mitogen-activated protein kinase 1 |
| 0.893002 | −1.12 | MAPK10 | mitogen-activated protein kinase 10 |
| 0.890498 | −1.12 | ELK1 | ELK1, member of ETS oncogene family |
| 0.882835 | −1.13 | ITGA6 | integrin, alpha 6 |
| 0.881247 | −1.13 | ITGAX | integrin, alpha X (antigen CD11C (p150), alpha polypeptide) |
| 0.86945 | −1.15 | ITGA7 | integrin, alpha 7 |
| 0.886344 | −1.15 | PRKCA | protein kinase C, alpha |
| 0.886155 | −1.15 | RAB5A | RAB5A, member RAS oncogene family |
| 0.860798 | −1.16 | PLCD1 | phospholipase C, delta 1 |
| 0.85798 | −1.17 | RHEB2 | Ras homolog enriched in brain 2 |
| 0.852815 | −1.17 | ITGA2 | integrin, alpha 2 (CD49B, alpha 2 subunit of VLA-2 receptor) |
| 0.850758 | −1.18 | ICAP-1A | integrin cytoplasmic domain-associated protein 1 |
| 0.84591 | −1.18 | FOS | v-fos FBJ marine osteosarcoma viral oncogene homolog |
| 0.838538 | −1.19 | ITGA8 | Nevin, alpha 8 |
| 0.832112 | −1.20 | ITGAL | Integrin, alpha L (antigen CD11A (p180), lymphocyte function-associated antigen 1; alpha polypeptide) |
| 0.829872 | −1.21 | ITGB4 | integrin, beta 4 |
| 0.828817 | −1.21 | RAF1 | v-raf-1 murine leukemia viral oncogene homolog 1 |
| 0.827565 | −1.21 | ITGA3 | integrin, alpha 3 (antigen CD49C, alpha 3 subunit of VLA-3 receptor) |
| 0.827109 | −1.21 | USF2 | upstream transcription factor 2, c-fos interacting |
| 0.822547 | −1.22 | CD47 | CD47 antigen (Rh-related antigen, integrin-associated signal transducer) |
| 0.822527 | −1.22 | | Human beta-1D integrin mRNA, cytoplasmic domain, partial cds |
| 0.81771 | −1.22 | RAC2 | ras-related C3 botullnum toxin substrate 2 (rho family, small GTP binding protein Rac2) |
| 0.814813 | −1.23 | EGF | epidermal growth factor |
| 0.814168 | −1.23 | MAPKAPK | Human MAPKAP kinase (3pK) mRNA, complete cds |
| 0.812273 | −1.23 | RREB1 | ras responsive element binding protein 1 |
| 0.811226 | −1.23 | ITGAL | integrin, alpha L (antigen CD11A (p180), lymphocyte function-associated antigen 1; alpha polypeptide) |
| 0.804076 | −1.24 | TGA8 | integrin, alpha 8 |
| 0.802546 | −1.25 | DGKZ | diacylglycerol kinase, zeta (104 kD) |
| 0.802242 | −1.25 | ITGA7 | integrin, alpha 7 |
| 0.796441 | −1.26 | MKNK1 | MAP kinase-interacting serine/threonine kinase 1 |
| 0.789261 | −1.27 | GADD45A | growth arrest and DNA-damage-inducible, alpha |
| 0.78846 | −1.27 | MAP2K8 | mitogen-activated protein kinase kinase 6 |
| 0.774047 | −1.29 | MAPKAPK | Human MAPKAP kinase (3pK) mRNA, complete cds |
| 0.77403 | −1.29 | PRKCH | protein kinase C, eta |
| 0.770607 | −1.30 | PRKCM | protein kinase C. mu |
| 0.750544 | −1.33 | ITGA7 | integrin, alpha 7 |
| 0.748912 | −1.34 | — | integrin alpha E precursor |
| 0.741196 | −1.35 | PRKCM | protein kinase C, mu |
| 0.73962 | −1.35 | PRKCM | protein kinase C, mu |
| 0.738806 | −1.36 | PRKCH | protein kinase C, eta |
| 0.732714 | −1.38 | — | integrin alpha E precursor |
| 0.732887 | −1.38 | PRKCD | protein kinase C, delta |
| 0.723635 | −1.38 | — | Human transcription factor junB (junB) gene, 5' region and complete cds |
| 0.722338 | −1.38 | RAC1 | ras-related C3 botulinum toxin substrate 1 (rho family, small GTP binding protein Rac1) |
| 0.720813 | −1.39 | RAB9 | RAB9, member RAS oncogene family |
| 0.718392 | −1.39 | ITGAL | integrin, alpha L (antigen CD11A (p180), lymphocyte function-associated antigen 1; alpha polypeptide) |
| 0.714437 | −1.40 | TGFB1 | transforming growth factor, beta 1 |
| 0.712175 | −1.40 | RACK7 | Homo sapiens protein kinase C-binding protein RACK7 mRNA, partial cds |
| 0.710224 | −1.41 | ITGB5 | integrin, beta 5 |
| 0.706845 | −1.41 | PLCE | phospholipase C, epsilon |
| 0.70524 | −1.42 | PRKCD | protein kinase C, delta |
| 0.699349 | −1.43 | MAP4K5 | mitogen-activated protein kinase kinase kinase kinase 5 |
| 0.67212 | −1.49 | RASA1 | RAS p21 protein activator (GTPase activating protein) 1 |
| 0.852848 | −1.53 | MAP3K10 | mitogen-activated protein kinase kinase 10 |
| 0.842873 | −1.58 | PRKCZ | Protein kinase C, zeta |
| 0.631817 | −1.58 | EGF | epidermal growth factor |
| 0.630705 | −1.59 | PRKCI | protein kinase C, iota |
| 0.62479 | −1.60 | ITGB8 | integrin, beta 8 |
| 0.614378 | −1.63 | ITGA3 | integrin, alpha 3 (antigen CD49C, alpha 3 subunit of VLA-3 receptor) |
| 0.813984 | −1.63 | ITGB5 | integrin, beta 5 |
| 0.613313 | −1.63 | PRKC1 | protein kinase C, iota |
| 0.610598 | −1.64 | RAB7 | RAB7, member RAS oncogene family |
| 0.605906 | −1.65 | ARHB | ras homolog gene family, member B |
| 0.575371 | −1.74 | RABL | RAB, member of RAS oncogene family-like |
| 0.544902 | −1.84- | — | Human beta-1D Integrin mRNA, cytoplasmic domain, partial cds |
| 0.5388 | −1.86 | EGF | epidermal growth factor |

TABLE 45-continued

| Ratio | Expression | Gene | Title |
|---|---|---|---|
| 0.524865 | −1.91 | ITGA4 | integrin, alpha 4 (antigen CD49D, alpha 4 subunit of VLA-4 receptor) |
| 0.420798 | −2.38 | — | Human beta-1D integrin mRNA, cytoplasmic domain, partial cds |
| 0.348998 | −2.88 | PRKC1 | protein kinase C, iota |

All Results from exposure to 590/810 nm LED(ZZ) or (DD) 250 ms on/100 ms off/100 pulses@3.6 mW/cm$^2$ 590/810 nm LED (DD) Human Fibroblast Microarray @24 hrs UPREGULATED

TABLE 46

| Ratio | Expression | Gene | Title |
|---|---|---|---|
| 4.37788 | 4.38 | | ESTs |
| 3.555185 | 3.56 | PAAT-BET | lysophosphatidic acid acyltransferase beta |
| 3.3171 | 3.32 | KRT15 | keratin 15 |
| 3.22777 | 3.23 | MLLT7 | myeloid/lymphoid or mixed-lineage leukemia (trithorax (Drosophila) homolog); translocated to, 7 |
| 3.017619 | 3.02 | KRT1 | keratin 1 (epidermolytic hyperkeratosis) |
| 3.001495 | 3.00 | CAV1 | caveolin 1, caveolae protein, 22 kD |
| 2.996355 | 3.00 | FNI | fibronectin 1 |
| 2.912214 | 2.91 | TMSB4X | thymosin, beta 4, X chromosome |
| 2.760801 | 2.76 | ANXA1 | annexin A1 |
| 2.636828 | 2.84 | TMSB4X | thymosin, beta 4, X chromosome |
| 2.584688 | 2.58 | SULT2B1 | sulfotransferase family 2B, member 1 |
| 2.531689 | 2.53 | COL6A3 | collagen, type VI, alpha 3 |
| 2.494702 | 2.49 | SEC23B | SEC23-like protein B |
| 2.375721 | 2.38 | GDN | CAG repeat containing (glia-derived nexin I alpha) |
| 2.363677 | 2.38 | MYO7A | myosin VIIA (Usher syndrome 18 (autosomal recessive, severe)) |
| 2.349795 | 2.35 | ARHGDIA | Rho GDP dissociation Inhibitor (GDI) alpha |
| 2.333071 | 2.33 | | ESTs, Moderately similar to III ALU SUBFAMILY SO WARNING ENTRY IIII [H. sapiens] |
| 2.310794 | 2.31 | MUC1 | mucin 1, transmembrane |
| 2.250399 | 2.25 | ADRBKI | adrenergic, beta, receptor kinase 1 |
| 2.240638 | 2.24 | SNRPF | small nuclear ribonucleoprotein polypeptide F |
| 2204388 | 2.20 | KRT10 | keratin 10 (epidermolytic hyperkeratosis; keratosis palmaris at plantaris) |
| 2.201947 | 2.20 | AHR | aryl hydrocarbon receptor |
| 2.18475 | 2.18 | | Human FKBP mRNA for FK-506 binding protein |
| 2.184285 | 2.18 | MMP1 | matrix metalloproteinese 1 (interstitial collagenase) |
| 2.183862 | 2.18 | | Homo sapiens chromosome 19, cosmid F22329 |
| 2.182361 | 2.18 | TPi1 | triosephosphate isomerase 1 |
| 2.174421 | 2.17 | CYP2B6 | cytochrome P450, subfamily IIB (phenobarbital-inducible), polypeptide 6 |
| 2.167876 | 2.17 | UQCRB | ubiquinol-cytochrome c reductase binding protein |
| 2.186883 | 2.17 | RPS16 | ribosomal protein S16 |
| 2.151532 | 2.15 | ITGB5 | integrin, beta 5 |
| 2.137382 | 2.14 | PRKCI | protein kinase C, iota |
| 2.136893 | 2.14 | RPL31 | ribosomal protein L31 |
| 2.135801 | 2.14 | LAMR1 | laminin receptor 1 (67 kD, ribosomal protein SA) |
| 2.132298 | 2.13 | PSMB9 | proteasome (prosome, macropain) subunit, beta type, 9 (large multifunctional protease 2) |
| 2.117549 | 2.12 | HSPB1 | heat shock 27 kD protein 1 |
| 2.113886 | 2.11 | | Human beta-1D integrin mRNA, cytoplasmic domain, partial cds |
| 2.1039 | 2.10 | MMP2 | matrix metalloproteinase 2 (gelatinase A, 72 kD gelitinase, 72 kD type IV collagenase) |
| 2.103515 | 2.10 | MMP2 | matrix metalloproteinase 2 (gelatinase A, 72 kD gelatinase, 72 kD type IV collagenase) |
| 2.092089 | 2.09 | KRT7 | keratin 7 |
| 2.090792 | 2.09 | NACA | nascent-polypeptide-associated complex alpha polypeptide |
| 2.080719 | 2.08 | PTMA | prothymosin, alpha (gene sequence 28) |
| 2.078029 | 2.08 | PA2G4 | proliferation-associated 2G4, 38 kD |
| 2.083182 | 2.08 | RPL27A | ribosomal protein L27a |
| 2.081387 | 2.06 | | ESTs |
| 2.060074 | 2.06 | RNASELI | ribonuclease L (2',5'-origoisoadenylate synthetase-dependent) inhibitor |
| 2.05182 | 2.05 | COL6A2 | collagen, type VI, alpha 2 |
| 2.05139 | 2.05 | | Human mRNA for ornithine decarboxylase antizyme, ORF 1 and ORF 2 |
| 2.04409 | 2.04 | RPL11 | ribosomal protein L11 |
| 2.039738 | 2.04 | CDH2 | cadherin 2, N-cadherin (neuronal) |
| 2.039518 | 2.04 | PMS2L12 | postmeiotic segregation increased 2-like 12 |
| 2.02107 | 2.02 | POLR2L | polymerase (RNA) II (DNA directed) polypeptide L (7.6 kD) |
| 2.020879 | 2.02 | | ESTs, Highly similar to 606 RIBOSOMAL PROTEIN L28 [H. sapiens] |
| 2.019761 | 2.02 | PRKDC | protein kinase, DNA-activated, catalytic polypeptide |
| 2.014017 | 2.01 | SEC61B | protein translocation complex beta |
| 2.0054 | 2.01 | GRO1 | GRO1 oncogene (melanoma growth stimulating activity, alpha) |
| 2.004741 | 2.00 | | ESTs, Moderately similar to cadherin [H. sapiens] |
| 1.991037 | 1.99 | TFCOUP2 | transcription factor COUP 2 (chicken ovalbumin upstream promoter 2, apolipoprotein regulatory protein) |
| 1.990129 | 1.99 | LGALS3 | lectin, galactoside-binding, soluble, 3 (galectin 3) |
| 1.985069 | 1.97 | | ESTs |
| 1.96 | 1.98 | CDH11 | cadherin 11 (OB-cadherin, osteoblast) |
| 1.959463 | 1.96 | RPS28 | ribosomal protein S28 |
| 1.958978 | 1.98 | | ESTs |
| 1.947297 | 1.95 | | Homo sapiens mRNA for K1AA0788 protein, partial cds |
| 1.94351 | 1.94 | MYL1 | myosin, light polypeptide 1, alkali; skeletal, fast |
| 1.927321 | 1.93 | CBP2 | collagen-binding protein 2 (colligen 2) |
| 1.926284 | 1.93 | CAV1 | caveolin 1, caveolae protein, 22 kD |
| 1.925577 | 1.93 | CBP2 | collagen-binding protein 2 (collagen 2) |
| 1.924493 | 1.92 | | Homo sapiens mRNA; cDNA DKFZp588L2123 (from clone DKFZp588L2123) |
| 1.924285 | 1.92 | COX8B | cytochrome c oxidase subunit VIb |
| 1.920658 | 1.92 | KPNB1 | karyopherin (importin) beta 1 |
| 1.906771 | 1.91 | MNPEP | methionine aminopeptidase; .eIF-2-associated p67 |
| 1.906318 | 1.91 | PI6 | protease inhibitor 6 (placental thrombin inhibitor) |
| 1.905516 | 1.91 | HMG17 | high-mobility group (nonhistone chromosomal) protein 17 |
| 1.904415 | 1.90 | CBP2 | collagen-binding protein 2 (colligen 2) |
| 1.886166 | 1.89 | RANBP7 | RAN binding protein 7 |
| 1.885023 | 1.89 | PABPL1 | poly(A)-binding protein-like 1 |
| 1.874848 | 1.87 | KRT1 | keratin 1 (epidermolytic hyperkeratosis) |
| 1.871322 | 1.87 | MMP2 | matrix metalloproteinase 2 (gelatinase A, 72 kD gelatinase, 72 kD type IV collagenase) |
| 1.870603 | 1.87 | VIM | vimentin |
| 1.870045 | 1.87 | ATP5C1 | ATP synthase, H+ transporting, |

TABLE 46-continued

| Ratio | Expression | Gene | Title |
|---|---|---|---|
| 1.865942 | 1.87 | OSF-2 | mitochondrial F1 complex, gamma polypepilde 1 osteoblast specific factor 2 (fasciclin I-like) |
| 1.863348 | 1.88 | | Homo sapiens chromosome 19, cosmid F22329 |
| 1.861111 | 1.88 | S100A10 | S100 calcium-binding protein A10 (annexin II ligand, calpactin I, light polypeptide (p11)) |
| 1.860058 | 1.86 | CST3 | cystatin C (amyloid angiopathy and cerebral hemorrhage) |
| 1.858106 | 1.88 | CD81 | CD81 antigen (target of antiproliferative antibody 1) |
| 1.858004 | 1.86 | RPL6 | ribosomal protein L6 |
| 1.856855 | 1.86 | COL2A1 | collagen, type II, alpha 1 (primary osteoarthritis, spondyloepiphyseal dysplasia, congenital) |
| 1.855778 | 1.88 | BCRP1 | breakpoint cluster region protein, uterine leiomyoma, 1; barrier to autointegration factor |
| 1.853552 | 1.85 | | ESTs |
| 1.852019 | 1.85 | HXB | hexabrachion (tenascin C, cytotactin) |
| 1.850728 | 1.85 | HLA-DNA | major histocompatibility complex, class II, DN alpha |
| 1.849278 | 1.85 | KRT7 | keratin 7 |
| 1.848257 | 1.85 | RPL7A | ribosomal protein L7a |
| 1.84526 | 1.85 | LAMR1 | laminin receptor 1 (87 kD, ribosomal protein SA) |
| 1.84325 | 1.84 | HMG1 | high-mobility group (nonhistone chromosomal) protein 1 |
| 1.842043 | 1.84 | | EST |
| 1.839891 | 1.84 | CCND1 | cyclin D1 (PRAD1: parathyroid adenomatosis 1) |
| 1.836536 | 1.84 | GDN | CAG repeat containing (glia-derived nexin I alpha) |
| 1.835849 | 1.84 | | ESTs, Moderately similar to IIII ALU SUBFAMILY SQ WARNING ENTRY IIII [*H. sapiens*] |
| 1.833092 | 1.83 | RPL18 | ribosomal protein L18 |
| 1.83305 | 1.83 | S100A10 | S100 calcium-binding protein A10 (annexin II ligand, calpactin I, light polypeptide (p11)) |
| 1.832272 | 1.83 | MLCB | myosin, light polypeptide, regulatory, non-sarcomeric (20 kD) |
| 1.832255 | 1.83 | SAP18 | sin3-associated polypeptide, 18 kD |
| 1.832097 | 1.83 | ANXA1 | annexin AI |
| 1.831283 | 1.83 | HOX11 | homeo box 11 (T-cell lymphoma 3-associated breakpoint) |
| 1.830147 | 1.83 | FH | fumarate hydratase |
| 1.827878 | 1.83 | YB1 | Major histocompatibility complex, class II, Y box-binding protein I; DNA-binding protein B |
| 1.827431 | 1.83 | PSEN1 | presenilin 1 (Alzheimer disease 3) |
| 1.828973 | 1.83 | PTP4A2 | protein tyrosine phosphatase type IVA member 2 |
| 1.825279 | 1.83 | CDH2 | cadherin 2, N-cadherin (neuronal) |
| 1.825232 | 1.83 | GDN | CAG repeat containing (glia-derived nexin I alpha) |
| 1.823895 | 1.82 | DGUOK | deoxyguanosine kinase |
| 1.822602 | 1.82 | CDH11 | cadherin 11 (OB-cadherin, osteoblast) |
| 1.821921 | 1.82 | | Human metallothinoein (MT)I-F gene |
| 1.820694 | 1.82 | SRD5A2 | steroid-5-alpha-reductase, alpha polypeptide 2 (3-oxo-5 alpha-steroid delta 4-dehydrogenase alpha 2) |
| 1.819337 | 1.82 | RPS4X | ribosomal protein S4, X-linked |
| 1.812413 | 1.81 | NNAT | neuronatin |
| 1.808221 | 1.81 | RPL28 | ribosomal protein L28 |
| 1.806496 | 1.81 | SPARC | secreted protein, acidic, cysteine-rich (osteonectin) |
| 1.804253 | 1.80 | | ESTs |

590/810 nm LED (DD) Human Fibroblast Microarray @24 hrs

DOWNREGULATED

TABLE 47

| Ratio | Expression | Gene | Title |
|---|---|---|---|
| 0.505996 | −1.98 | JAK1 | Janus kinase 1 (a protein tyrosine kinase) |
| 0.50599 | −1.98 | TPM1 | tropomyosin 1 (alpha) |
| 0.50578 | −1.98 | C3F | putative protein similar to nessy (Drosophila) |
| 0.505811 | −1.98 | KIAA0042 | KIAA0042 gene product |
| 0.505338 | −1.98 | | ESTs |
| 0.505251 | −1.98 | | EST |
| 0.504824 | −1.98 | RGS6 | regulator of G protein signalling 6 |
| 0.502908 | −1.99 | IL1RL1 | int rleulkin 1 receptor-lik 1 |
| 0.502703 | −1.99 | | ESTs |
| 0.502123 | −1.99 | | ESTs |
| 0.501903 | −1.99 | EPS15 | epidermal growth factor receptor pathway substrate 15 |
| 0.501849 | −1.99 | AQP7 | aquaporin 7 |
| 0.501728 | −1.99 | NVL | nuclear VCP-like |
| 0.501417 | −1.99 | APOB | apolipoprotein B (including Ag(x) antigen) |
| 0.501383 | −1.99 | RHD | Rhesus blood group, D antigen |
| 0.501024 | −2.00 | | ESTs |
| 0.499388 | −2.00 | ADCYAP1 | adenylate cyclase activating polypeptide 1 (pituitary) |
| 0.499379 | −2.00 | | ESTs |
| 0.497612 | −2.01 | RNPS1 | RNA-binding protein |
| 0.497308 | −2.01 | EGR3 | early growth response 3 |
| 0.496852 | −2.01 | | ESTs, Highly similar to NEUROLYSIN PRECURSOR [*R. norvegicus*] |
| 0.495827 | −2.02 | COL9A3 | collagen, type IX, alpha 3 |
| 0.495781 | −2.02 | EDNRB | endothelin receptor type B |
| 0.495697 | −2.02 | | ESTs |
| 0.495379 | −2.02 | | ESTs, Highly similar to CARBONIC ANHYDRASE III [*h. sapiens*] |
| 0.49513 | −2.02 | | ESTs |
| 0.494838 | −2.02 | | ESTs |
| 0.494834 | −2.02 | CYP2E | cytochrome P450, subfamily IIE (ethanol-inducible) |
| 0.493342 | −2.03 | | Human zinc-finger protein C2H2-150 mRNA, complete cds |
| 0.492507 | −2.03 | | Homo sapiens mRNA for leucocyte vacuolar protein sorting |
| 0.492448 | −2.03 | ITGA6 | Integrin, alpha 6 |
| 0.491538 | −2.03 | HM74 | putative chemokine receptor; GTP-binding protein |
| 0.491512 | −2.03 | | ESTs |
| 0.49102 | −2.04 | CYP2J2 | cytochrome P450, subfamily IIJ (arachidonic acid epoxygenase) polypeptide 2 |
| 0.490859 | −2.04 | DNASE1L3 | deoxyribonuclease I-like 3 |
| 0.490338 | −2.04 | IL6 | interleukin 6 (Interferon, beta 2) |
| 0.488881 | −2.05 | | EST |
| 0.487732 | −2.05 | KCNJ13 | potassium inwardly-rectifying channel, subfamily J, member 13 |
| 0.487612 | −2.05 | HSD11B1 | hydroxysteroid (11-beta) dehydrogenase 1 |
| 0.487227 | −2.05 | PIP5K1B | phosphatidylinositol-4-phosphate 5-kinase, type 1, beta |

TABLE 47-continued

| Ratio | Expression | Gene | Title |
|---|---|---|---|
| 0.488057 | −2.06 | | ESTs |
| 0.484803 | −2.06 | DSC2 | desmocolin 2 |
| 0.484767 | −2.08 | | ESTs |
| 0.484476 | −2.08 | — | EST |
| 0.484148 | −2.07 | HEC | highly expressed in cancer, rich in leucine heptad repeats |
| 0.483241 | −2.07 | SALL2 | sal (Drosophila)-like 2 |
| 0.482959 | −2.07 | BR140 | bromodomain-containing protein, 140 kD (peregrin) |
| 0.482408 | −2.07 | | EST |
| 0.481448 | −2.08 | | ESTs |
| 0.480445 | −2.08 | CD22 | CD22 antigen |
| 0.478784 | −2.09 | | ESTs |
| 0.478612 | −2.09 | PRPH | peripherin |
| 0.477533 | −2.09 | | ESTs |
| 0.477408 | −2.09 | | ESTs |
| 0.477231 | −2.10 | VRK2 | vaccinia related kinase 2 |
| 0.476812 | −2.10 | | ESTs, Moderately similar to poly(ADP-ribose) polymerase [*H. sapiens*] |
| 0.476372 | −2.10 | | ESTs |
| 0.475903 | −2.10 | TGFB3 | transforming growth factor, beta 3 |
| 0.475219 | −2.10 | | Homo sapiens (PWD) gene mRNA, 3' end |
| 0.474813 | −2.11 | | ESTs |
| 0.473687 | −2.11 | CYP1A1 | cytochrome P450, subfamily I (aromatic compound-inducible), polypeptide 1 |
| 0.472832 | −2.11 | GAC1 | gnome amplified on chromosome 1 protein (leucine-rich) |
| 0.471048 | −2.12 | SAA1 | serum amyloid A1 |
| 0.470787 | −2.12 | TMEM1 | transmembrane protein 1 |
| 0.488068 | −2.14 | UBD | diubiquitin |
| 0.467735 | −2.14 | GYPA | glycophorin A (includes MN blood group) |
| 0.488793 | −2.14 | FGB | fibrinogen, B beta polypeptide |
| 0.488138 | −2.15 | | Human heterochromatin protein HP1Hs-gamma mRNA, complete cds |
| 0.484548 | −2.15 | | ESTs |
| 0.484524 | −2.15 | CDC7L1 | CDC7 (cell division cycle 7, S. cerevisiae, homolog)-like 1 |
| 0.464376 | −2.15 | BRAF | v-raf murine sarcoma viral oncogene homolog B1 |
| 0.461843 | −2.17 | OSMR | oncostatin M receptor |
| 0.461711 | −2.17 | GAK | cyclin G associated kinase |
| 0.481285 | −2.17 | PRL | prolactin |
| 0.481174 | −2.17 | RODH | oxidative 3 alpha hydroxysteroid dehydrogenase; retinol dehydrogenase |
| 0.480889 | −2.17 | | ESTs |
| 0.457589 | −2.19 | XRCC4 | X-ray repair complementing defective repair in Chinese hamster cells 4 |
| 0.457432 | −2.19 | | Human heterochromatin protein HP1He-gamma mRNA, complete cds |
| 0.456747 | −2.19 | MYH11 | myosin, heavy polypeptide 11, smooth muscle |
| 0.455606 | −2.19 | | ESTs |
| 0.453198 | −2.21 | | ESTs, Highly similar to keratin K5, 58K type II, epidermal [*H. sapiens*] |
| 0.452355 | −2.21 | | EST |
| 0.451604 | −2.21 | MSE55 | serum constituent protein |
| 0.45109 | −2.22 | KIAA0427 | KIAA0427 gene product |
| 0.450427 | −2.22 | | ESTs |
| 0.448814 | −2.23 | HRG | histidine-rich glycoprotein |
| 0.448084 | −2.24 | | ESTs, Highly similar to calcium-activated potassium channel [*H. sapiens*] |
| 0.444169 | −2.25 | ITGAV | integrin, alpha V (vitronectin receptor, alpha polypeptide, antigen CD51) |
| 0.443218 | −2.28 | | ESTs |
| 0.442987 | −2.28 | | ESTs |
| 0.442003 | −2.26 | | Human transcription factor junB (junB) gene, 5' region and complete cds |
| 0.441276 | −2.27 | WHITE1 | ATP-binding cassette 8 (homolog of Drosophila white) |
| 0.440934 | −2.27 | KIAA0311 | A kinase (PRKA) anchor protein 6 |
| 0.438989 | −2.28 | ESM1 | endothelial cell-specific |
| 0.438627 | −2.28 | LTA4H | leukotriene A4 hydrolase |
| 0.435728 | −2.30 | IL1B | interleukin 1, beta |
| 0.435105 | −2.30 | BDH | 3-hydroxybutyrate dehydrogenase (heart, mitochondrial) |
| 0.432874 | −2.31 | | ESTs, Highly similar to ARYLSULFATASE D PRECURSOR [*H. sapiens*] |
| 0.429736 | −2.33 | PSCDBP | pleckstrin homology, Sec7 and coiled/coil domains, binding protein |
| 0.428978 | −2.33 | MYBPC1 | myosin-binding protein C, slow-type |
| 0.427744 | −2.34 | | ESTs, Weakly similar to hypothetical protein [*H. sapiens*] |
| 0.427136 | −2.34 | | EST |
| 0.426459 | −2.34 | | ESTs, Highly similar to LECT2 precursor [*H. sapiens*] |
| 0.423683 | −2.38 | PRH2 | proline-rich protein HaeIII subfamily 2 |
| 0.42099 | −2.38 | | ESTs |
| 0.418102 | −2.39 | PTCH | patched (Drosophila) homolog |
| 0.412483 | −2.42 | | ESTs |
| 0.411249 | −2.43 | | ESTs, Highly similar to keratin K5, 58K type II, epidermal [*H. sapiens*] |
| 0.408283 | −2.45 | | ESTs |
| 0.407869 | −2.45 | | ESTs |
| 0.408033 | −2.46 | | ESTs |
| 0.401289 | −2.49 | WAVE3 | WASP family Verprolin-homologous protein 3 |
| 0.391109 | −2.56 | | Human putative astrocytic NOVA-like RNA-binding protein (ANOVA) mRNA, partial oils |
| 0.387487 | −2.58 | | ESTs |
| 0.385543 | −2.59 | | ESTs, Weakly similar to (define not available 4102188) [*H. sapiens*] |
| 0.383043 | −2.81 | | ESTs |
| 0.383009 | −2.61 | | ESTs |
| 0.382362 | −2.62 | | ESTs, Weakly similar to (define not available 4102188) [*H. sapiens*] |
| 0.375872 | −2.68 | IFNG | interferon, gamma |
| 0.369436 | −2.71 | | ESTs |
| 0.367155 | −2.72 | | ESTs |
| 0.388711 | −2.73 | | ESTs |
| 0.358349 | −2.79 | | ESTs |
| 0.353871 | −2.83 | | ESTs |
| 0.343033 | −2.92 | | Human heterochromatin protein HP1Hs-gamma mRNA, complete cds |
| 0.339846 | −2.94 | | ESTs |
| 0.324327 | −3.08 | | EST |
| 0.307325 | −3.25 | | ESTs |
| 0.298473 | −3.35 | BS69 | adenovirus 5 E1A binding protein |
| 0.251472 | −3.98 | | ESTs |
| 0240206 | −4.16 | SLC16A1 | solute carrier family 16 (monocarboxylic acid transporters), member 1 |

All Results from exposure to 590/810 nm LED(ZZ) r (DD) 250 ms on/100 ms off/100 pulses@3.6 mW/cm²

Gene Expression for 24 hr Protein Kinases 590/810 nm LED(DD)

TABLE 48

| | | |
|---|---|---|
| 1.1 | SRPK2 | SFRS protein kinase 2 |
| −1.3 | MAPK10 | mitogen-activated protein kinase10 |
| −1.8 | RACK17 | protein kinase C-binding protein |
| −1.2 | MAP2K6 | mitogen-activated protein kinase kinase 6 |
| 1 | MAP2K3 | mitogen-activated protein kinase kinase 3 |
| 1 | MAPK6 | mitogen-activated protein kinase 6 |
| 1.2 | CAMK1 | calcium/calmodulin-dependent protein kinase I |
| 1.2 | PRKCI | protein kinase C, iota |

TABLE 48-continued

| | | |
|---|---|---|
| 1.6 | PRKCI | protein kinase C, iota |
| 2.1 | PRKCI | protein kinase C, iota |
| 1.3 | ROCK1 | Rho-associated, coiled-coil containing protein kinase 1 |
| 2 | PRKDC | protein kinase, DNA-activated, catalytic polypeptide |
| −1.3 | MAP3K10 | mitogen-activated protein kinase kinase kinase 10 |
| −1.7 | NRGN | neurogranin (protein kinase C substrate, RC3) |
| −2 | MAP2K7 | mitogen-activated protein kinase kinase 7 |
| −1.1 | ESTs, | Moderately similar to CAMP-DEPENDENT PROTEIN KINASE INHIBITOR. TESTIS ISOFORMS 1 AND 2 [*M. musculus*] |
| 1.2 | PDPK1 | 3-phosphoinositide dependent protein kinase-1 |
| 1.1 | PK428 | ser-Thr protein kinase related to the myotonic dystrophy protein kinase |
| 1.5 | PRKCM | protein kinase C, mu |
| 1.5 | PRKCM | protein kinase C, mu |
| −1.1 | PRKCM | protein kinase C, mu |
| −1.5 | PRKY | protein kinase, Y-linked |
| 1.1 | MAPK1 | mitogen-activated protein kinase 1 |
| −1.3 | PRKACA | protein kinase, cAMP-dependent, catalytic, alpha |
| −1.1 | | ESTs, Weakly similar to microtubule-associated serine/threonine protein kinase MAST205 [*M. musculus*] |
| −1.6 | PRKACB | protein kinase, cAMP-dependent, catalytic, beta |
| 1.4 | PRKCH | protein kinase C, eta |
| 1.3 | PRKCH | protein kinase C, eta |
| −1.1 | PRKCH | protein kinase C, eta |
| −1.4 | PRKCA | protein kinase C, alpha |
| −1.5 | PRKCA | protein kinase C, alpha |
| −1.9 | PRKCA | protein kinase C, alpha |
| −1.3 | MAP3K5 | mitogen-activated protein kinase kinase kinase 5 |
| −1.6 | MAP3K5 | mitogen-activated protein kinase kinase kinase 5 |
| −1.4 | MAP3K5 | mitogen-activated protein kinase kinase kinase 5 |
| 1.4 | KIAA0137 | serine threonine protein kinase |
| −1.3 | MAPK9 | mitogen-activated protein kinase 9 |
| 1.3 | MAP4K5 | mitogen-activated protein kinase kinase kinase kinase 5 |
| −1.3 | PKIA | protein kinase (cAMP-dependent, catalytic) inhibitor alpha |
| −1.2 | PCTK1 | PCTAIRE protein kinase 1 |
| −1.2 | PCTK3 | PCTAIRE protein kinase 3 |
| −1.9 | MAPK4 | mitogen-activated protein kinase 4 |
| 1 | PRKCB1 | protein kinase C, beta 1 |
| 1.2 | PRKCB1 | protein kinase C, beta 1 |
| −1 | PRKCB1 | protein kinase C, beta 1 |
| 1 | PRKCD | protein kinase C, delta |
| −1.1 | PRKCD | protein kinase C, delta |
| −1.1 | PRKCD | protein kinase C, delta |
| −1.2 | MAP2K2 | mitogen-activated protein kinase kinase 2 |
| 1.2 | MAPK14 | mitogen-activated protein kinase 14 |
| −1.1 | PRKAB1 | protein kinase, AMP-activated, beta 1 non-catalytic subunit |
| 1.2 | PRKAR1B | protein kinase, cAMP-dependent, regulatory, type I, beta |
| −1.1 | ESTs, | Highly similar to TYROSINE-PROTEIN KINASE RECEPTOR HEK-2 PRECURSOR [*H. sapiens*] |
| −1.2 | ESTs, | Highly similar to TYROSINE-PROTEIN KINASE RECEPTOR HEK-2 PRECURSOR [*H. sapiens*] |
| 1.1 | ESTs, | Highly similar to TYROSINE-PROTEIN KINASE RECEPTOR HEK-2 PRECURSOR [*H. sapiens*] |
| −1.6 | | Homo sapiens protein kinase C-binding protein RACK7 mRNA, partial cds |
| −1.2 | PRKG1 | protein kinase, cGMP-dependent, type I |
| 1.8 | PRKAR1A | protein kinase, cAMP-dependent, regulatory, type 1, alpha (tissue specific extinguisher 1) |
| −1.1 | PKIG | protein kinase (cAMP-dependent, catalytic) inhibitor gamma |
| 1.2 | ESTs, | Highly similar to CAMP-DEPENDENT PROTEIN KINASE TYPE II-ALPHA REGULATORY CHAIN [*H. sapiens*] |
| −1 | SRPK1 | SFRS protein kinase 1 |
| 1.3 | ESTs, | Weakly similar to serine/threonine protein kinase 51PK(S) [*M. musculus*] |
| −1 | ZAP70 | zeta-chain (TCR) associated protein kinase (70 kD) |
| 1.1 | ZAP70 | zeta-chain (TCR) associated protein kinase (70 kD) |
| 1.1 | ZAP70 | zeta-chain (TCR) associated protein kinase (70 kD) |
| −1 | | ESTs, Highly similar to serine/threonine protein kinase [*H. sapiens*] |
| −1.6 | MAP2K3 | mitogen-activated protein kinase kinase 3 |
| 1.2 | DAPK3 | death-associated protein kinase 3 |
| −1.2 | PRKX | protein kinase, X-linked |
| −1.5 | PRKG2 | protein kinase, cGMP-dependent, type II |

Other embodiments and uses of the invention will be apparent to those skilled in the art from consideration of the specification and practice of the invention disclosed herein. All references cited herein, including all publications, U.S. and foreign patents and patent applications, are specifically and entirely incorporated by reference. It is intended that the specification and examples be considered exemplary only.

I claim:

1. A method, comprising:
   photomodulating mammalian tissue with more than one light source of narrowband, multi chromatic electromagnetic radiation,
   wherein at least one light source emits radiation at a wavelength corresponding to yellow light and at least one light source emits radiation corresponding to infra-red light, and the yellow light is emitted at a greater intensity than the infra-red light, and
   wherein the tissue is exposed to an energy fluence of less than 4 J/cm$^2$.

2. The method of claim 1, wherein at least one light source emits radiation having a dominant emissive wavelength of 580 nm to 600 nm and at least one light source emits radiation having a dominant emissive wavelength of 850 nm to 950 nm.

3. The method of claim 2, wherein the at least one light source emits radiation having a dominant emissive wavelength of 590 nm at an energy output of 4 mW/cm$^2$ and at least one light source emits radiation having a dominant emissive wavelength of 850 nm at an energy output of 1 mW/cm$^2$.

4. The method of claim 1, comprising varying the ratio of infra-red light intensity with respect to yellow light intensity with at least one optical, mechanical, or electrical filter.

5. The method of claim 1, wherein the ratio of the intensity of yellow light to infra-red light is 4:1.

6. The method of claim 1, wherein the yellow light is emitted simultaneously with the infra-red light.

* * * * *